US007365166B2

(12) United States Patent
Baca et al.

(10) Patent No.: US 7,365,166 B2
(45) Date of Patent: *Apr. 29, 2008

(54) ANTI-VEGF ANTIBODIES

(75) Inventors: Manuel Baca, Black Rock (AU);
James A. Wells, Burlingame, CA (US);
Leonard G. Presta, San Francisco, CA (US); Henry B. Lowman, El Granada, CA (US); Yvonne Man-Yee Chen, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 11/536,603

(22) Filed: Sep. 28, 2006

(65) Prior Publication Data

US 2007/0059312 A1 Mar. 15, 2007

Related U.S. Application Data

(60) Continuation of application No. 10/974,591, filed on Oct. 26, 2004, which is a continuation of application No. 09/723,752, filed on Nov. 27, 2000, now Pat. No. 7,060,269, which is a division of application No. 08/908,469, filed on Aug. 6, 1997, now Pat. No. 6,884,879.

(60) Provisional application No. 60/126,446, filed on Apr. 7, 1997, now abandoned.

(51) Int. Cl.
*C07K 16/00* (2006.01)
(52) U.S. Cl. ............... 530/387.1; 530/387.3; 536/23.53; 435/320.1; 424/130.1
(58) Field of Classification Search .......... 530/387.1, 530/387.3; 536/23.53; 435/320.1; 424/130.1
See application file for complete search history.

(56) References Cited

U.S. PATENT DOCUMENTS

| | | | |
|---|---|---|---|
| 4,816,567 | A | 3/1989 | Cabilly et al. |
| 5,530,101 | A | 6/1996 | Queen et al. |
| 5,580,723 | A | 12/1996 | Wells et al. |
| 6,037,454 | A | 3/2000 | Jardieu et al. |
| 6,054,297 | A | 4/2000 | Carter et al. |
| 6,472,585 | B1 * | 10/2002 | Botstein et al. ............... 800/18 |
| 6,884,879 | B1 | 4/2005 | Baca et al. |
| 7,060,269 | B1 | 6/2006 | Baca et al. |
| 7,169,901 | B2 * | 1/2007 | Baca et al. ............... 530/387.1 |
| 2002/0032315 | A1 | 3/2002 | Baca et al. |

FOREIGN PATENT DOCUMENTS

| | | |
|---|---|---|
| EP | 0239400 | 8/1994 |
| EP | 0451216 | 1/1996 |
| EP | 451216 B1 | 1/1996 |
| EP | 1 325 932 B1 | 4/2005 |
| GB | 2188638 | 10/1987 |
| GB | 2268744 | 12/1994 |
| WO | 91/00996 | 1/1991 |
| WO | WO 91/09967 | 7/1991 |
| WO | WO 92/18619 | 10/1992 |
| WO | WO 92/22653 | 12/1992 |
| WO | WO 94/04679 | 3/1994 |
| WO | WO 94/10202 | 5/1994 |
| WO | WO 96/30046 | 10/1996 |
| WO | WO 98/45331 | 10/1998 |
| WO | WO 98/45332 | 10/1998 |

OTHER PUBLICATIONS

Brown et al., "Expression of vascular permeability factor (vascular endothelial growth factor) and its receptors in adenocarcinomas of the gastrointestinal tract" *Cancer Research* 53(19):4727-4735 (1993).
Brown et al., "Expression of vascular permeability factor (vascular endothelial growth factor) and its receptors in breast cancer" *Human Pathology* 26(1):86-91 (1995).
Carter et al., "Humanization of an Anti-p185$^{HER2}$ Antibody For Human Cancer Therapy" *Proc. Natl. Acad. Sci. USA* 89(10):4285-4289 (May 1992).
Chang et al., "High-Level Secretion of Human Growth Hormone by *Escherichia coli* " *Gene* 55:189-196 (1987).
Chisholm, "High Efficiency Gene Transfer into Mammaliam Cells" *DNA Cloning 4. Mammaliam Systems* pp. 1-41 (1995).
Chothia et al., "Domain Association in Immunoglobulin Molecules. The Packing of Variable Domains" *Journal of Molecular Biology* 186:651-663 (1985).
Clapp et al., "The 16-kilodalton N-terminal fragment of human prolactin is a potent inhibitor of angiogenesis" *Endocrinology* 133(3):1292-1299 (1993).
Cunningham et al., "Production of an Atrial Natriuretic Peptide Variant that is Specific for Type A Receptor" *EMBO Journal* 13(11):2508-2515 (1994).
de Vries et al., "The fms-like tyrosine kinase, a receptor for vascular endothelial growth factor" *Science* 255:989-991 (1992).
Dvorak et al., "Vascular permeability factor/vascular endothelial growth factor, microvascular hyperpermeability, and angiogenesis" *American Journal of Pathology* 146(5):1029-1039 (1995).
Eaton et al., "Construction and characterization of an active factor VIII variant lacking the central one-third of the molecule" *Biochemistry* 25:8343-8347 (1986).
Eigenbrot et al., "X-Ray Structures of Fragments From Binding and Nonbinding Versions of a Humanized Anti-CD18 Antibody: Structural Indications of the Key Role of $V_H$ Residues 59 to 65" *Proteins: Structure, Function, and Genetics* 18:49-62 (1994).
Eigenbrot et al., "X-Ray Structures of the Antigen-Binding Domains From Three Variants of Humanized Anti-p185$^{HER2}$ Antibody 4D5 and Comparison with Molecular Modeling" *J. Mol. Biol.* 229:969-995 (1993).
Ferrara and Davis-Smyth, "The Biology of Vascular Endothelial Growth Factor" *Endocrine Reviews* 18(1) :4-25 (1997).

(Continued)

*Primary Examiner*—David J. Blanchard
*Assistant Examiner*—Parithosh K. Tungaturthi
(74) *Attorney, Agent, or Firm*—Grant Kalinowski

(57) ABSTRACT

Humanized and variant anti-VEGF antibodies and various uses therefor are disclosed. The anti-VEGF antibodies have strong binding affinities for VEGF; inhibit VEGF-induced proliferation of endothelial cells in vitro; and inhibit tumor growth in vivo.

7 Claims, 16 Drawing Sheets

OTHER PUBLICATIONS

Folkman and Shing, "Angiogenesis" *Journal of Biological Chemistry* 267:10931-10934 (1992).

Foote et al., "Antibody Framework Residues Affecting the Conformation of the Hypervariable Loops" *J. Mol. Biol.* 224:487-499 (1992).

Garner, A., "Vascular Diseases" *Pathobiology of Ocular Disease. A Dynamic Approach*, Garner, A., Klintworth GK Eds., 2nd edition, NY:Marcel Dekker pp. 1625-1710 (1994).

Garrard et al., "Fab assembly and enrichment in a monovalent phage display system" *Bio/technology* 9:1373-1377 (1991).

Good et al., "A tumor suppressor-dependent inhibitor of angiogenesis is immunologically and functionally indistinguishable from a fragment of thrombospondin" *Proc. Natl. Acad. Sci. USA* 87(17):6624-6628 (1990).

Gorman et al., "Transient Production of Proteins Using an Adenovirus Transformed Cell Line" *DNA Prot. Eng. Tech.* 2(1):3-10 (1990).

Graham et al., "Characteristics of a Human Cell Line Transformed by DNA from Human Adenovirus Type 5" *J. Gen. Virol.* 36:59-72 (1977).

Hawkins et al., "Selection of Phage Antibodies by Binding Affinity Mimicking Affinity Maturation" *J. Mol. Biol.* 226:889-896 (1992).

Horak et al., "Angiogenesis, assessed by platelet/endothelial cell adhesion molecule antibodies, as indicator of node metastases and survival in breast cancer" *Lancet* 340(8828):1120-1124 (1992).

Kabat et al. *Sequences of Proteins of Immunological Interest*, U.S. Dept. of Health and Human Services, NIH, 5th edition vol. 1:103-108, 324-331 (1991).

Karlsson et al., "Kinetic analysis of monoclonal antibody-antigen interactions with a new biosensor based analytical system" *J. Immun. Methods* 145:229-240 (1991).

Karlsson et al., "Kinetic and Concentration Analysis Using BIA Technology" *Methods: A Comparison to Methods in Enzymology* 6:99-110 (1994).

Kettleborough et al., "Humanization of a Mouse Monoclonal Antibody by CDR-grafting: the Importance of Framework Residues on Loop Conformation" *Protein Engineering* 4(7):773-783 (1991).

Kim et al., "Inhibition of Vascular Endothelial Growth Factor-Induced Angiogenesis Suppresses Tumour Growth in vivo" *Nature* 362:841-844 (Apr. 29, 1993).

Kim et al., "The Vascular Endothelial Growth Factor Proteins: Identification of Biologically Relevant Regions by Neutralizing Monoclonal Antibodies" *Growth Factors* 7(1):53-64 (1992).

Klagebrun and D'Amore, "Regulators of angiogenesis" *Ann. Rev. Physiol.* 53:217-239 (1991).

Kunkel et al., "Efficient site-directed mutagenesis using uracil-containing DNA" *Methods in Enzymology* 204:125-139 (1991).

Kunkel, T., "Rapid and Efficient Site-Specific Mutagenesis Without Phenotypic Selection" *Proc. Natl. Acad. Sci.* 82:488-492 (1985).

Leung et al., "Vascular Endothelial Growth Factor is a Secreted Angiogenic Mitogen" *Science* 246:1306-1309 (Dec. 1989).

Lopez et al., "Transdifferentiated retinal pigment epithelial cells are immunoreactive for vascular endothelial growth factor in surgically excised age-related macular degeneration-related choroidal neovascular membranes" *Invest. Ophthalmol. Vis. Sci.* 37(5):855-868 (1996).

Lowman et al., "Selecting High-Affinity Binding Proteins by Monovalent Phage Display" *Biochemistry* 30(45):10832-10838 (1991).

Lucas, et al., "High-Level Production of Recombinant Proteins in CHO Cells Using a Dicistronic DHFR Intron Expression Vector" *Nucleic Acids Research* 24(9):1774-1779 (1996).

Macchiarini et al., "Relation of neovascularisation to metastasis of non-small-cell lung cancer" *Lancet* 340(8812):145-146 (1992).

Mattern et al., "Association of vascular endothelial growth factor expression with intratumoral microvessel density and tumour cell proliferation in human epidermoid lung carcinoma" *Brit. J. Cancer* 73(7):931-934 (1996).

Melnyk et al., "Vascular endothelial growth factor promotes tumor dissemination by a mechanism distinct from its effect on primary tumor growth" *Cancer Research* 56(4):921-924 (Feb. 15, 1996).

Novotny et al., "Structural invariants of antigen binding: comparison of immunoglobulin $V_L$-$V_H$ and $V_L$-$V_L$ domain dimers" *Proc. Natl. Acad. Sci. USA* 82(14):4592-4596 (Jul. 1985).

O'Reilly et al., "Angiostatin: a novel angiogenesis inhibitor that mediates the suppression of metastases by a Lewis lung carcinoma" *Cell* 79(2):315-328 (1994).

O'Reilly et al., "Endostatin: an endogenous inhibitor of angiogenesis and tumor growth" *Cell* 88(2):277-285 (1997).

Padlan, E., "A Possible Procedure for Reducing the Immunogenicity of Antibody Variable Domains While Preserving Their Ligand-Binding Properties" *Molecular Immunology* 28(4/4):489-498 (1991).

Park et al., "Placenta growth factor. Potentiation of vascular endothelial growth factor bioactivity, in vitro and in vivo, and high affinity binding to Flt-1 but not to Flk-1/KDR" *Journal of Biological Chemistry* 269(41):25646-25654 (1994).

Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).

Presta et al., "Humanization of an Antibody Directed Against IgE" *J. Immunol.* 151(5):2623-2632 (Sep. 1, 1993).

Queen et al., "A humanized antibody that binds to the interleukin 2 receptor" *Proc. Natl. Acad. Sci. USA* 86(24):10029-10033 (Dec. 1989).

Roguska et al., "Humanization of murine monoclonal antibodies through variable domain resurfacing" *Proc. Natl. Acad. Sci. USA* 91:969-973 (Feb. 1994).

Rosok et al., "A Combinatorial Library Strategy for the Rapid Humanization of Anticarcinoma BR96 Fab" *Journal of Biological Chemistry* 271(37):22611-22618 (Sep. 13, 1996).

Rudikoff et al., "Single amino acid substitution altering antigen-binding specificity" *Proc. Natl. Acad. Sci. USA* 79:1979-1983 (1982).

Sanger et al., "DNA Sequencing with Chain-terminating Inhibitors" *Proc. Natl. Acad. Sci. USA* 74(12):5463-5467 (Dec. 1977).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217-225 (Jan. 1, 1992).

Studnicka et al., "Human-engineered monocolonal antibodies retain full specific binding activity by preserving non-CDR complementarity-modulating residues" *Protein Eng.* 7(6):805-814 (1994).

Tempest et al., "Reshaping a Human Monoclonal Antibody to Inhibit Human Respiratory Syncytial Virus Infection In Vivo" *Bio/Technology* 9:266-271 (Mar. 1991).

Vieira et al., "Production of Single-stranded Plasmid DNA" *Methods in Enzymology* 153:3-11 (1987).

Warren et al., "Regulation by vascular endothelial growth factor of human colon cancer tumorigenesis in a mouse model of experimental liver metastasis" *J. Clin. Invest.* 95(4):1789-1797 (Apr. 1995).

Weidner et al., "Tumor angiogenesis and metastasis—correlation in invasive breast carcinoma" *New England J. of Medicine* 324(1):1-8 (1991).

Werther et al., "Humanization of an Anti-Lymphocyte Function-Associated Antigen (LFA)-1 Monoclonal Antibody and Reengineering of the Humanized Antibody for Binding to Rhesus LFA-1" *J. of Immunology* 157:4986-4995 (1996).

Winter et al., "Making antibodies by phage display technology" *Annual Review of Immunology* 12:433-455 (1994).

Yang et al., "CDR walking mutagenesis for the affinity maturation of a potent human anti-HIV-1 antibody into the picomolar range" *Journal of Molecular Biology* 254(3):392-403 (Dec. 1, 1995).

Yelton et al., "Affinity Maturation of the BR96 Anti-Carcinoma Antibody by Codon-Based Mutagenesis" *The Journal of Immunology* 155:1994-2004 (1995).

Clackson et al., "Making Antibody Fragments Using Phage Display Libraries" *Nature* 352(15):624-628 (Aug. 1991).

Amit et al., "Three-Dimensional Structure of an Antigen-Antibody Complex at 2.8 A Resolution" *Science* 233:747-753 (Aug. 1986).

Chen et al., "Selection and Analysis of an Optimized Anti-VEGF Antibody: Crystal Structure of an Affinity-matured Fab in Complex with Antigen" *Journal of Molecular Biology* 293(4):865-881 (1999).

Coleman, P.M., "Effects of amino acid sequence changes on antibody-antigen interactions" *Research in Immunology* 145:33-36 (1994).

Garrard et al., "Assembly and Enrichment in a Monovalent Phage Display System" *Biotechnology* 9:1373-11377 (1997).

Ibragimova and Wade, "Stability of the β-Sheet of the WW Domain: A Molecular Dynamics Simulation Study" *Biophysical Journal* 77:2191-2198 (Oct. 1999).

Panka et al., "Variable region framework differences result in decreased or increased affinity of variant anti-digoxin antibodies" *Proc. Natl. Acad. Sci. USA* 85:3080-3084 (May 1988).

Paul, William E *Fundamental Immunology*, 3rd edition pp. 292-295 (1993).

Adamis et al., "Inhibition of Vascular Endothelial Growth Factor Prevents Retinal Ischemia-Associated Iris Neovascularization in a Nonhuman Primate" *Arch. Opthalmology* 114(1):66-71 (1996).

Aiello et al., "Vascular endothelial growth factor in ocular fluid of patients with diabetic retinopathy and other retinal disorders" *New England J. of Medicine* 331(22):1480-1487 (1994).

Alberts et al., "Molecular Biology of the Cell", 3rd edition, Garland Publishing pp. 1154 (1994).

Allen et al., "Specificity of the T cell Receptor: Two Different Determinants are Generated by the Same Peptide and the $IA^k$ Molecule" *J. Immunol.* 135(1):368-373 (Jul. 1985).

Baca et al., "Antibody Humanization Using Monovalent Phage Display" *Journal of Biological Chemistry* 272(16):10678-10684 (1997).

Bass et al., "Hormone Phage: An Enrichment Method for Variant Proteins with Altered Binding Properties" *Proteins: Structure, Function, and Genetics* 8(4):309-314 (1990).

Bendig, M. M., "Humanization of Rodent Monoclonal Antibodies" *Methods: A Companion to Methods in Enzymology* 8:83-93 (1994).

Berkman et al., "Expression of the vascular permeability factor/vascular endothelial growth factor gene in central nervous system neoplasms" *J. Clin. Invest.* 91(1):153-159 (1993).

Borgstrom et al., "Complete inhibition of angiogenesis and growth of microtumors by anti-vascular endothelial growth factor neutralizing antibody: novel concepts of angiostatic therapy from intravital videomicroscopy" *Cancer Research* 56(17):4032-4039 (Sep. 1, 1996).

* cited by examiner

```
         1         10        20        30        40
A4.6.1   EIQLVQSGPELKQPGETVRISCKASGYTFTNYGMNWVKQA
         *   *  ** *      *** *     ‾‾‾‾‾‾‾‾‾‾‾ *

F(ab)-12 EVQLVESGGGLVQPGGSLRLSCAASGYTFTNYGMNWVRQA
                                  ‾‾* ** *‾‾ humIII   EVQLVESGGGLVQPGGSLRLSCAASGFTFSSYAMSWVRQA 50      a        60        70        80
A4.6.1   PGKGLKWMGWINTYTGEPTYAADFKRRFTFSLETSASTAYL
              * *‾‾‾‾‾‾‾‾‾‾‾‾‾‾‾‾           *  *

F(ab)-12 PGKGLEWVGWINTYTGEPTYAADFKRRFTFSLDTSKSTAYL
                 * ***  *      *  *    * humIII   PGKGLEWVSVISGDGGSTTYADSVKGRFTISRDNSKNTLYL abc         90                 110
A4.6.1   QISNLKNDDTATYFCAKYPHYYGSSHWYFDVWGAGTTVTVSS   (SEQ. ID NO:9)
          *** ***      *  ‾‾‾‾‾‾‾‾‾‾‾‾   * *

F(ab)-12 QMNSLRAEDTAVYYCAKYPHYYGSSHWYFDVWGQGTLVTVSS   (SEQ. ID NO:7)
                         * ‾‾‾‾‾‾‾‾‾‾‾‾  * humIII   QMNSLRAEDTAVYYCARG----------FDYWGQGTLVTVSS   (SEQ. ID NO:11)
```

FIG._1A

```
         1         10        20        30        40
A4.6.1   DIQMTQTTSSLSASLGDRVIISCSASQDISNYLNWYQQKP
              **      *    * ‾‾‾‾‾‾‾‾‾‾‾‾‾‾‾

F(ab)-12 DIQMTQSPSSLSASVGDRVTITCSASQDISNYLNWYQQKP
                                ‾*‾ ‾*‾ ‾*‾ humKI    DIQMTQSPSSLSASVGDRVTITCRASQSISNYLAWYQQKP 50        60        70        80
A4.6.1   DGTVKVLIYFTSSLHSGVPSRFSGSGSGTDYSLTISNLEP
         ****     ‾‾‾‾‾‾‾‾            **  *  *

F(ab)-12 GKAPKVLIYFTSSLHSGVPSRFSGSGSGTDFTLTISSLQP
              *  ‾*‾*‾‾* humKI    GKAPKLLIYAASSLESGVPSRFSGSGSGTDFTLTISSLQP 90        100
A4.6.1   EDIATYYCQQYSTVPWTFGGGTKLEIKR       (SEQ. ID NO:10)
           *    ‾‾‾‾‾‾‾‾‾‾     *  *

F(ab)-12 EDFATYYCQQYSTVPWTFGQGTKVEIKR       (SEQ. ID NO:8)
                 ‾***‾ humKI    EDFATYYCQQYNSLPWTFGQGTKVEIKR       (SEQ. ID NO:12)
```

FIG._1B

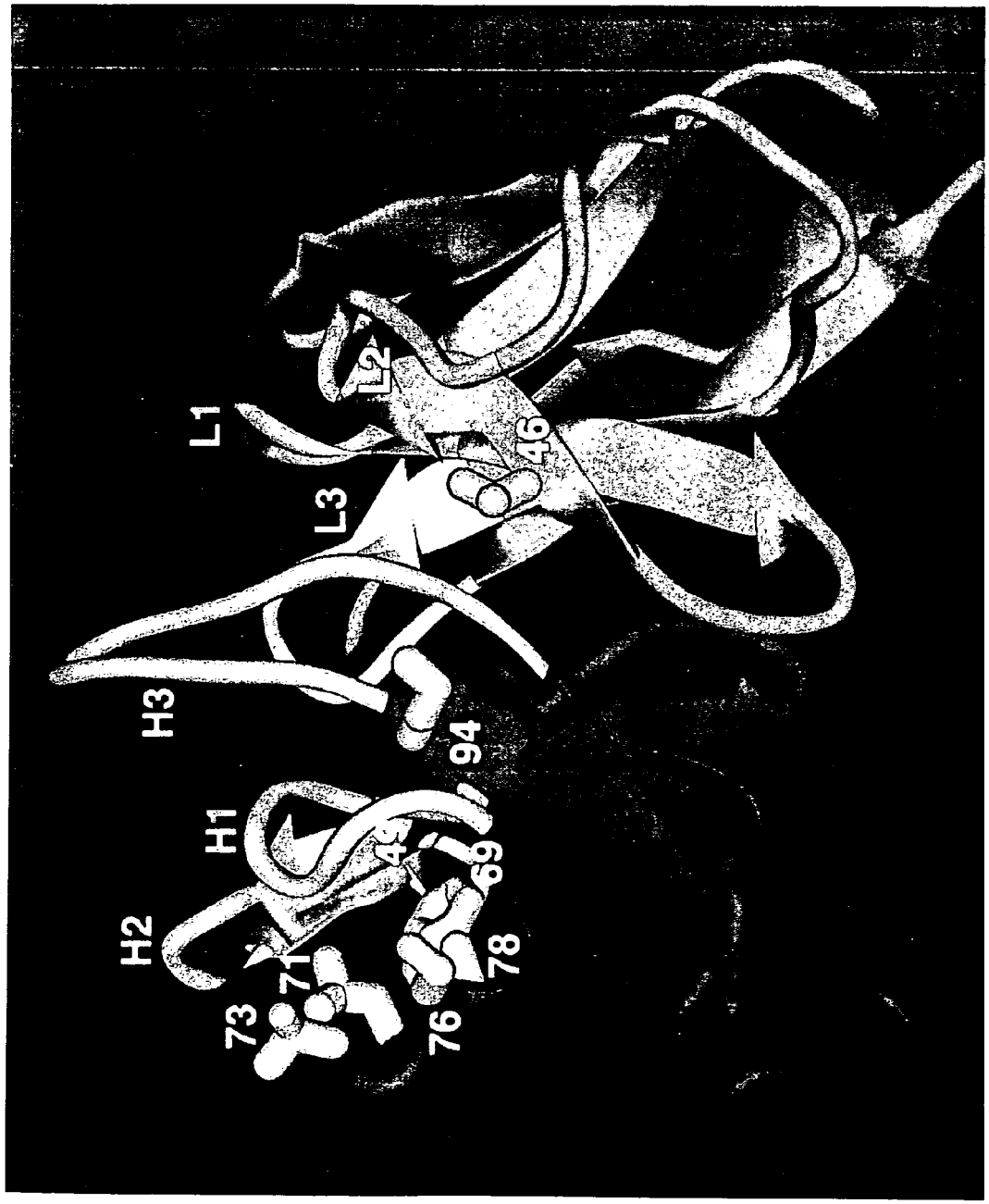
FIG._2

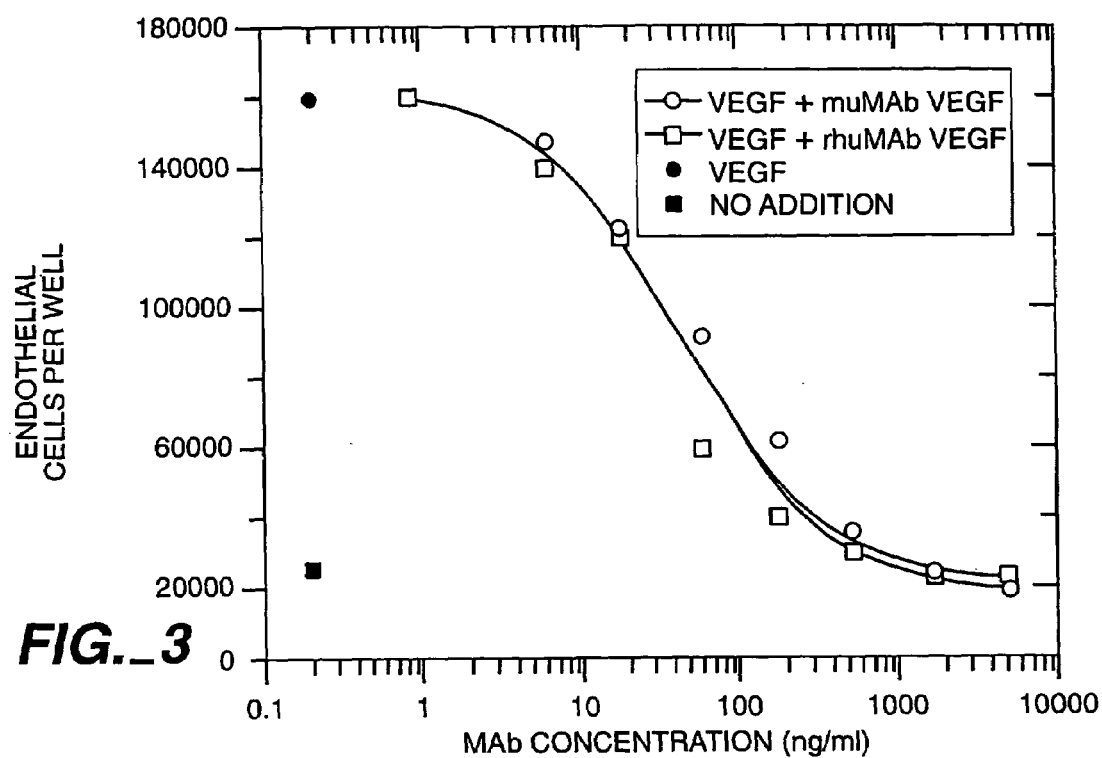
FIG._3
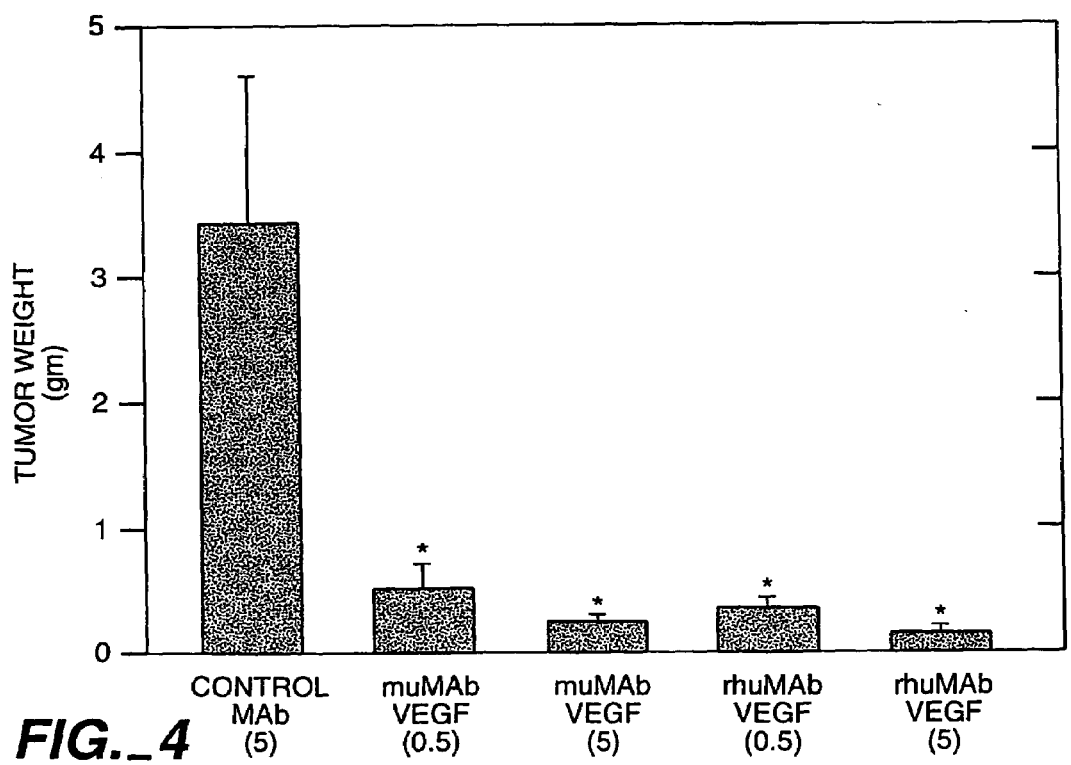
FIG._4

```
              10         20         30         40
A4.6.1  DIQMTQTTSSLSASLGDRVIISCSASQDISNYLNWYQQKP
        **          *      * *
hu2.0   DIQMTQSPSSLSASVGDRVTITCSASQDISNYLNWYQQKP hu2.10  DIQMTQSPSSLSASVGDRVTITCSASQDISNYLNWYQQKP 50         60         70         80
A4.6.1  DGTVKVLIYFTSSLHSGVPSRFSGSGSGTDYSLTISNLEP
        ****  *                      **   *  *
hu2.0   GKAPKLLIYFTSSLHSGVPSRFSGSGSGTDFTLTISSLQP
                                     ·
hu2.10  GKAPKLLIYFTSSLHSGVPSRFSGSGSGTDYTLTISSLQP 90        100
A4.6.1  EDIATYYCQQYSTVPWTFGGGTKLEIK        (SEQ.ID NO:10)
          *                *  *
hu2.0   EDFATYYCQQYSTVPWTFGQGTKVEIK        (SEQ.ID NO:13)

hu2.10  EDFATYYCQQYSTVPWTFGQGTKVEIK        (SEQ.ID NO:15)
```

FIG._5A

```
              10         20         30         40
A4.6.1  EIQLVQSGPELKQPGETVRISCKASGYTFTNYGMNWVKQA
         *  *  ** *   *** *  *                *
hu2.0   EVQLVESGGGLVQPGGSLRLSCAASGYTFTNYGMNWVRQA
                                               ·
hu2.10  EVQLVESGGGLVQPGGSLRLSCAASGYTFTNYGMNWIRQA 50 a       60         70         80
A4.6.1  PGKGLKWMGWINTYTGEPTYAADFKRRFTFSLETSASTAYL
            * *                      * ***  ** *
hu2.0   PGKGLEWVGWINTYTGEPTYAADFKRRFTISRDNSKNTLYL
                                      · · ··  ·
hu2.10  PGKGLEWVGWINTYTGEPTYAADFKRRFTISLDTSASTVYL abc  90        100abcdef     110
A4.6.1  QISNLKNDDTATYFCAKYPHYYGSSHWYFDVWGAGTTVTVSS   (SEQ.ID NO:9)
        *** ***    *  *                   *  *
hu2.0   QMNSLRAEDTAVYYCARYPHYYGSSHWYFDVWGQGTLVTVSS   (SEQ.ID NO:14)
                     ·
hu2.10  QMNSLRAEDTAVYYCAKYPHYYGSSHWYFDVWGQGTLVTVSS   (SEQ.ID NO:16)
```

FIG._5B

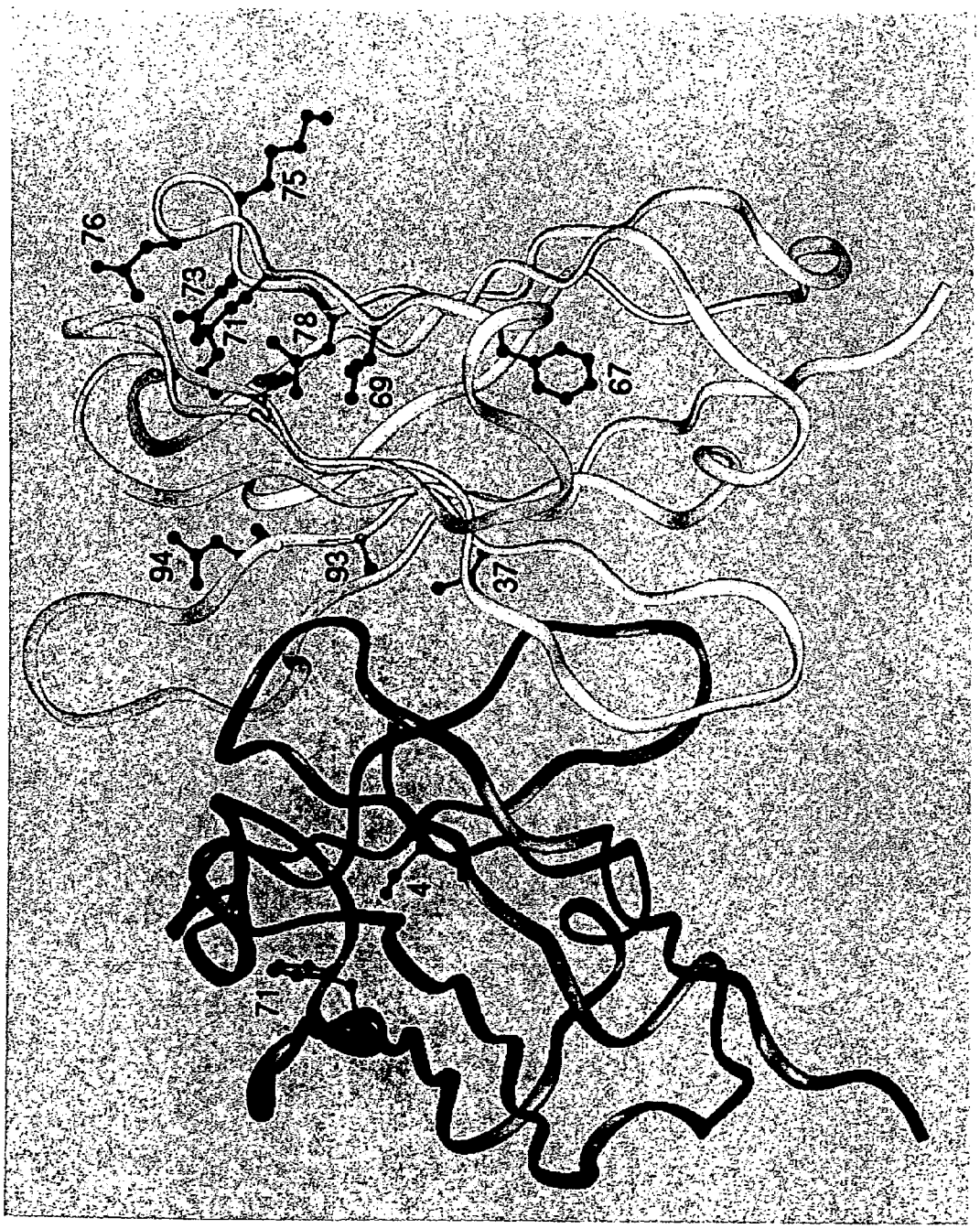
FIG._6

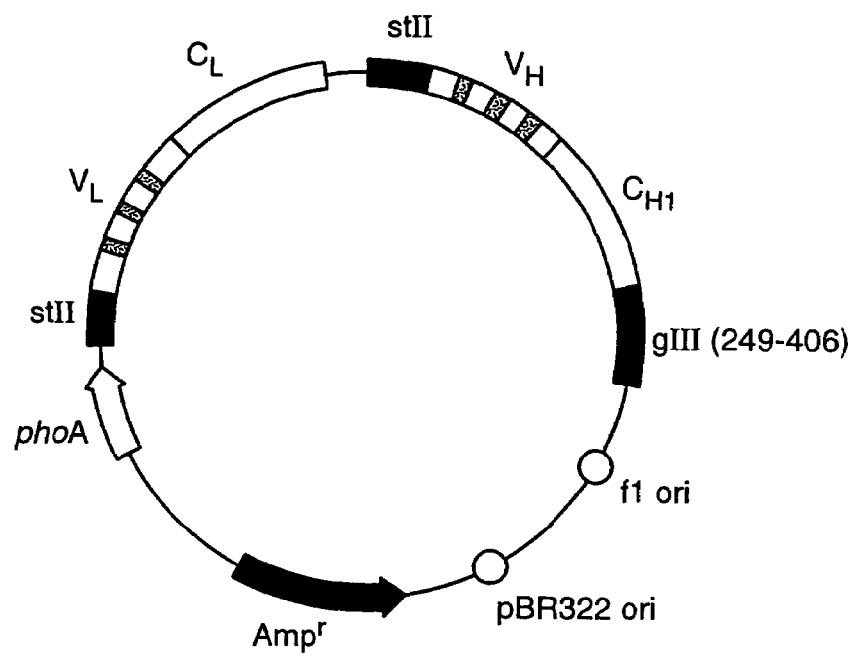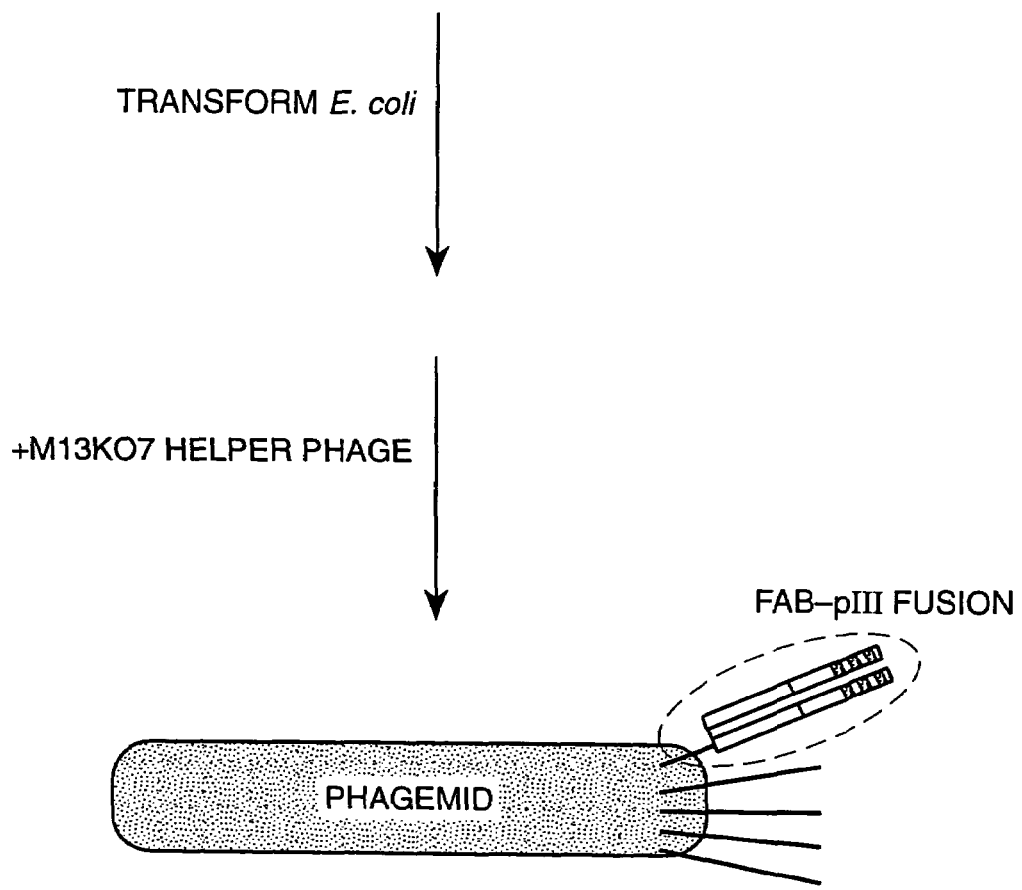
FIG._7

```
GAATTCAACT TCTCCATACT TTGGATAAGG AAATACAGAC ATGAAAAATC TCATTGCTGA        60

GTTGTTATTT AAGCTTTGGA GATTATCGTC ACTGCAATGC TTCGCAATAT GGCGCAAAAT       120

GACCAACAGC GGTTGATTGA TCAGGTAGAG GGGGCGCTGT ACGAGGTAAA GCCCGATGCC       180

AGCATTCCTG ACGACGATAC GGAGCTGCTG CGCGATTACG TAAAGAAGTT ATTGAAGCAT       240

CCTCGTCAGT AAAAAGTTAA TCTTTTCAAC AGCTGTCATA AAGTTGTCAC GGCCGAGACT       300

TATAGTCGCT TTGTTTTTAT TTTTTAATGT ATTTGTAACT AGAATTCGAG CTCGGTACCC       360

GGGGATCCTC TAGAGGTTGA GGTGATTTT ATG AAA AAG AAT ATC GCA TTT CTT        413
                                 Met Lys Lys Asn Ile Ala Phe Leu
                                 -23             -20
```

```
CTT GCA TCT ATG TTC GTT TTT TCT ATT GCT ACA AAC GCG TAC GCT GAT        461
Leu Ala Ser Met Phe Val Phe Ser Ile Ala Thr Asn Ala Tyr Ala Asp
-15             -10             -5                              1
                BEGIN stII SIGNAL SEQUENCE
ATC CAG TTG ACC CAG TCC CCG AGC TCC CTG TCC GCC TCT GTG GGC GAT        509
Ile Gln Leu Thr Gln Ser Pro Ser Ser Leu Ser Ala Ser Val Gly Asp
                5               10              15

AGG GTC ACC ATC ACC TGC AGC GCA AGT CAG GAT ATT AGC AAC TAT TTA        557
Arg Val Thr Ile Thr Cys Ser Ala Ser Gln Asp Ile Ser Asn Tyr Leu
        20              25              30
BEGIN LIGHT CHAIN
AAC TGG TAT CAA CAG AAA CCA GGA AAA GCT CCG AAA CTA CTG ATT TAC        605
Asn Trp Tyr Gln Gln Lys Pro Gly Lys Ala Pro Lys Leu Leu Ile Tyr
    35              40              45

TTC ACC TCC TCT CTC CAC TCT GGA GTC CCT TCT CGC TTC TCT GGA TCC        653
Phe Thr Ser Ser Leu His Ser Gly Val Pro Ser Arg Phe Ser Gly Ser
50              55              60              65

GGT TCT GGG ACG GAT TAC ACT CTG ACC ATC AGC AGT CTG CAG CCA GAA        701
Gly Ser Gly Thr Asp Tyr Thr Leu Thr Ile Ser Ser Leu Gln Pro Glu
        70              75              80

GAC TTC GCA ACT TAT TAC TGT CAA CAG TAT AGC ACC GTG CCG TGG ACG        749
Asp Phe Ala Thr Tyr Tyr Cys Gln Gln Tyr Ser Thr Val Pro Trp Thr
            85              90              95

TTT GGA CAG GGT ACC AAG GTG GAG ATC AAA CGA ACT GTG GCT GCA CCA        797
Phe Gly Gln Gly Thr Lys Val Glu Ile Lys Arg Thr Val Ala Ala Pro
            100             105             110

TCT GTC TTC ATC TTC CCG CCA TCT GAT GAG CAG TTG AAA TCT GGA ACT        845
Ser Val Phe Ile Phe Pro Pro Ser Asp Glu Gln Leu Lys Ser Gly Thr
        115             120             125

GCT TCT GTT GTG TGC CTG CTG AAT AAC TTC TAT CCC AGA GAG GCC AAA        893
Ala Ser Val Val Cys Leu Leu Asn Asn Phe Tyr Pro Arg Glu Ala Lys
130             135             140             145
```

FIG._8A

```
GTA CAG TGG AAG GTG GAT AAC GCC CTC CAA TCG GGT AAC TCC CAG GAG      941
Val Gln Trp Lys Val Asp Asn Ala Leu Gln Ser Gly Asn Ser Gln Glu
            150                 155                 160

AGT GTC ACA GAG CAG GAC AGC AAG GAC AGC ACC TAC AGC CTC AGC AGC      989
Ser Val Thr Glu Gln Asp Ser Lys Asp Ser Thr Tyr Ser Leu Ser Ser
            165                 170                 175

ACC CTG ACG CTG AGC AAA GCA GAC TAC GAG AAA CAC AAA GTC TAC GCC     1037
Thr Leu Thr Leu Ser Lys Ala Asp Tyr Glu Lys His Lys Val Tyr Ala
            180                 185                 190

TGC GAA GTC ACC CAT CAG GGC CTG AGC TCG CCC GTC ACA AAG AGC TTC     1085
Cys Glu Val Thr His Gln Gly Leu Ser Ser Pro Val Thr Lys Ser Phe
            195                 200                 205

AAC AGG GGA GAG TGT T AAGCTGATCC TCTACGCCGG ACGCATCGTG              1131
Asn Arg Gly Glu Cys 0 C* (SEQ.ID NO:130)
210

GCCCTAGTAC GCAACTAGTC GTAAAAAGGG TATCTAGAGG TTGAGGTGAT TTT ATG      1187
                                                           Met
                                                           -23
                        BEGIN stII SIGNAL SEQUENCE
AAA AAG AAT ATC GCA TTT CTT CTT GCA TCT ATG TTC GTT TTT TCT ATT     1235
Lys Lys Asn Ile Ala Phe Leu Leu Ala Ser Met Phe Val Phe Ser Ile
        -20             -15             -10

GCT ACA AAC GCG TAC GCT GAG GTT CAG CTG GTG GAG TCT GGC GGT GGC     1283
Ala Thr Asn Ala Tyr Ala Glu Val Gln Leu Val Glu Ser Gly Gly Gly
        -5              1               5               10

CTG GTG CAG CCA GGG GGC TCA CTC CGT TTG TCC TGT GCA GCT TCT GGC     1331
Leu Val Gln Pro Gly Gly Ser Leu Arg Leu Ser Cys Ala Ala Ser Gly
            15                  20                  25
                        BEGIN HEAVY CHAIN
TAT ACC TTC ACC AAC TAT GGT ATG AAC TGG ATC CGT CAG GCC CCG GGT     1379
Tyr Thr Phe Thr Asn Tyr Gly Met Asn Trp Ile Arg Gln Ala Pro Gly
            30                  35                  40

AAG GGC CTG GAA TGG GTT GGA TGG ATT AAC ACC TAT ACC GGT GAA CCG     1427
Lys Gly Leu Glu Trp Val Gly Trp Ile Asn Thr Tyr Thr Gly Glu Pro
            45                  50                  55

ACC TAT GCT GCG GAT TTC AAA CGT CGT TTT ACT ATA TCT GCA GAC ACC     1475
Thr Tyr Ala Ala Asp Phe Lys Arg Arg Phe Thr Ile Ser Ala Asp Thr
            60                  65                  70

TCC AGC AAC ACA GTT TAC CTG CAG ATG AAC AGC CTG CGC GCT GAG GAC     1523
Ser Ser Asn Thr Val Tyr Leu Gln Met Asn Ser Leu Arg Ala Glu Asp
75                  80                  85                  90

ACT GCC GTC TAT TAC TGT GCA AAG TAC CCG CAC TAT TAT GGG AGC AGC     1571
Thr Ala Val Tyr Tyr Cys Ala Lys Tyr Pro His Tyr Tyr Gly Ser Ser
                95                  100                 105
```

*FIG. 8B*

```
CAC TGG TAT TTC GAC GTC TGG GGT CAA GGA ACC CTG GTC ACC GTC TCC        1619
His Trp Tyr Phe Asp Val Trp Gly Gln Gly Thr Leu Val Thr Val Ser
            110                 115                 120

TCG GCC TCC ACC AAG GGC CCA TCG GTC TTC CCC CTG GCA CCC TCC TCC        1667
Ser Ala Ser Thr Lys Gly Pro Ser Val Phe Pro Leu Ala Pro Ser Ser
        125                 130                 135

AAG AGC ACC TCT GGG GGC ACA GCG GCC CTG GGC TGC CTG GTC AAG GAC        1715
Lys Ser Thr Ser Gly Gly Thr Ala Ala Leu Gly Cys Leu Val Lys Asp
        140                 145                 150

TAC TTC CCC GAA CCG GTG ACG GTG TCG TGG AAC TCA GGC GCC CTG ACC        1763
Tyr Phe Pro Glu Pro Val Thr Val Ser Trp Asn Ser Gly Ala Leu Thr
155                 160                 165                 170

AGC GGC GTG CAC ACC TTC CCG GCT GTC CTA CAG TCC TCA GGA CTC TAC        1811
Ser Gly Val His Thr Phe Pro Ala Val Leu Gln Ser Ser Gly Leu Tyr
                175                 180                 185

TCC CTC AGC AGC GTG GTG ACC GTG CCC TCC AGC AGC TTG GGC ACC CAG        1859
Ser Leu Ser Ser Val Val Thr Val Pro Ser Ser Ser Leu Gly Thr Gln
            190                 195                 200

ACC TAC ATC TGC AAC GTG AAT CAC AAG CCC AGC AAC ACC AAG GTC GAC        1907
Thr Tyr Ile Cys Asn Val Asn His Lys Pro Ser Asn Thr Lys Val Asp
            205                 210                 215

AAG AAA GTT GAG CCC AAA TCT TGT GAC AAA ACT CAC CTC TAG AGT GGC        1955
Lys Lys Val Glu Pro Lys Ser Cys Asp Lys Thr His Leu  *  Ser Gly
        220                 225                 230

GGT GGC TCT GGT TCC GGT GAT TTT GAT TAT GAA AAG ATG GCA AAC GCT        2003
Gly Gly Ser Gly Ser Gly Asp Phe Asp Tyr Glu Lys Met Ala Asn Ala
235                 240                 245                 250
                                    END LIGHT CHAIN              BE
AAT AAG GGG GCT ATG ACC GAA AAT GCC GAT GAA AAC GCG CTA CAG TCT        2051
Asn Lys Gly Ala Met Thr Glu Asn Ala Asp Glu Asn Ala Leu Gln Ser
                255                 260                 265
GIN g3p DOMAIN
GAC GCT AAA GGC AAA CTT GAT TCT GTC GCT ACT GAT TAC GGT GCT GCT        2099
Asp Ala Lys Gly Lys Leu Asp Ser Val Ala Thr Asp Tyr Gly Ala Ala
            270                 275                 280

ATC GAT GGT TTC ATT GGT GAC GTT TCC GGC CTT GCT AAT GGT AAT GGT        2147
Ile Asp Gly Phe Ile Gly Asp Val Ser Gly Leu Ala Asn Gly Asn Gly
        285                 290                 295

GCT ACT GGT GAT TTT GCT GGC TCT AAT TCC CAA ATG GCT CAA GTC GGT        2195
Ala Thr Gly Asp Phe Ala Gly Ser Asn Ser Gln Met Ala Gln Val Gly
        300                 305                 310

GAC GGT GAT AAT TCA CCT TTA ATG AAT AAT TTC CGT CAA TAT TTA CCT        2243
Asp Gly Asp Asn Ser Pro Leu Met Asn Asn Phe Arg Gln Tyr Leu Pro
315                 320                 325                 330
```

FIG._8C

```
TCC CTC CCT CAA TCG GTT GAA TGT CGC CCT TTT GTC TTT AGC GCT GGT    2291
Ser Leu Pro Gln Ser Val Glu Cys Arg Pro Phe Val Phe Ser Ala Gly
            335                 340                 345
AAA CCA TAT GAA TTT TCT ATT GAT TGT GAC AAA ATA AAC TTA TTC CGT    2339
Lys Pro Tyr Glu Phe Ser Ile Asp Cys Asp Lys Ile Asn Leu Phe Arg
            350                 355                 360
GGT GTC TTT GCG TTT CTT TTA TAT GTT GCC ACC TTT ATG TAT GTA TTT    2387
Gly Val Phe Ala Phe Leu Leu Tyr Val Ala Thr Phe Met Tyr Val Phe
            365                 370                 375
TCT ACG TTT GCT AAC ATA CTG CGT AAT AAG GAG TCT TAATCATGCC         2433
Ser Thr Phe Ala Asn Ile Leu Arg Asn Lys Glu Ser OC* (SEQ.ID NO:100)
            380                 385                 390
AGTTCTTTTG GCTAGCGCCG CCCTATACCT TGTCTGCCTC CCCGCGTTGC GTCGCGGTGC  2493
                      END G3 PROTEIN
ATGGAGCCGG GCCACCTCGA CCTGAATGGA AGCCGGCGGC ACCTCGCTAA CGGATTCACC  2553
ACTCCAAGAA TTGGAGCCAA TCAATTCTTG CGGAGAACTG TGAATGCGCA AACCAACCCT  2613
TGGCAGAACA TATCCATCGC GTCCGCCATC TCCAGCAGCC GCACGCGGCG CATCTCGGGC  2673
AGCGTTGGGT CCTGGCCACG GGTGCGCATG ATCGTGCTCC TGTCGTTGAG GACCCGGCTA  2733
GGCTGGCGGG GTTGCCTTAC TGGTTAGCAG AATGAATCAC CGATACGCGA GCGAACGTGA  2793
AGCGACTGCT GCTGCAAAAC GTCTGCGACC TGAGCAACAA CATGAATGGT CTTCGGTTTC  2853
CGTGTTTCGT AAAGTCTGGA AACGCGGAAG TCAGCGCCCT GCACCATTAT GTTCCGGATC  2913
TGCATCGCAG GATGCTGCTG GCTACCCTGT GGAACACCTA CATCTGTATT AACGAAGCGC  2973
TGGCATTGAC CCTGAGTGAT TTTTCTCTGG TCCCGCCGCA TCCATACCGC CAGTTGTTTA  3033
CCCTCACAAC GTTCCAGTAA CCGGGCATGT TCATCATCAG TAACCCGTAT CGTGAGCATC  3093
CTCTCTCGTT TCATCGGTAT CATTACCCCC ATGAACAGAA ATTCCCCCTT ACACGGAGGC  3153
ATCAAGTGAC CAAACAGGAA AAAACCGCCC TTAACATGGC CCGCTTTATC AGAAGCCAGA  3213
CATTAACGCT TCTGGAGAAA CTCAACGAGC TGGACGCGGA TGAACAGGCA GACATCTGTG  3273
AATCGCTTCA CGACCACGCT GATGAGCTTT ACCGCAGGAT CCGGAAATTG TAAACGTTAA  3333
TATTTTGTTA AAATTCGCGT TAAATTTTTG TTAAATCAGC TCATTTTTTA ACCAATAGGC  3393
CGAAATCGGC AAAATCCCTT ATAAATCAAA AGAATAGACC GAGATAGGGT TGAGTGTTGT  3453
TCCAGTTTGG AACAAGAGTC CACTATTAAA GAACGTGGAC TCCAACGTCA AAGGGCGAAA  3513
AACCGTCTAT CAGGGCTATG GCCCACTACG TGAACCATCA CCCTAATCAA GTTTTTTGGG  3573
GTCGAGGTGC CGTAAAGCAC TAAATCGGAA CCCTAAAGGG AGCCCCCGAT TTAGAGCTTG  3633
```

FIG._8D

```
ACGGGGAAAG CCGGCGAACG TGGCGAGAAA GGAAGGGAAG AAAGCGAAAG GAGCGGGCGC    3693
TAGGGCGCTG GCAAGTGTAG CGGTCACGCT GCGCGTAACC ACCACACCCG CCGCGCTTAA    3753
TGCGCCGCTA CAGGGCGCGT CCGGATCCTG CCTCGCGCGT TTCGGTGATG ACGGTGAAAA    3813
CCTCTGACAC ATGCAGCTCC CGGAGACGGT CACAGCTTGT CTGTAAGCGG ATGCCGGGAG    3873
CAGACAAGCC CGTCAGGGCG CGTCAGCGGG TGTTGGCGGG TGTCGGGGCG CAGCCATGAC    3933
CCAGTCACGT AGCGATAGCG GAGTGTATAC TGGCTTAACT ATGCGGCATC AGAGCAGATT    3993
GTACTGAGAG TGCACCATAT GCGGTGTGAA ATACCGCACA GATGCGTAAG GAGAAAATAC    4053
CGCATCAGGC GCTCTTCCGC TTCCTCGCTC ACTGACTCGC TGCGCTCGGT CGTTCGGCTG    4113
CGGCGAGCGG TATCAGCTCA CTCAAAGGCG GTAATACGGT TATCCACAGA ATCAGGGGAT    4173
AACGCAGGAA AGAACATGTG AGCAAAAGGC CAGCAAAAGG CCAGGAACCG TAAAAAGGCC    4233
GCGTTGCTGG CGTTTTTCCA TAGGCTCCGC CCCCCTGACG AGCATCACAA AAATCGACGC    4293
TCAAGTCAGA GGTGGCGAAA CCCGACAGGA CTATAAAGAT ACCAGGCGTT TCCCCCTGGA    4353
AGCTCCCTCG TGCGCTCTCC TGTTCCGACC CTGCCGCTTA CCGGATACCT GTCCGCCTTT    4413
CTCCCTTCGG GAAGCGTGGC GCTTTCTCAT AGCTCACGCT GTAGGTATCT CAGTTCGGTG    4473
TAGGTCGTTC GCTCCAAGCT GGGCTGTGTG CACGAACCCC CCGTTCAGCC CGACCGCTGC    4533
GCCTTATCCG GTAACTATCG TCTTGAGTCC AACCCGGTAA GACACGACTT ATCGCCACTG    4593
GCAGCAGCCA CTGGTAACAG GATTAGCAGA GCGAGGTATG TAGGCGGTGC TACAGAGTTC    4653
TTGAAGTGGT GGCCTAACTA CGGCTACACT AGAAGGACAG TATTTGGTAT CTGCGCTCTG    4713
CTGAAGCCAG TTACCTTCGG AAAAAGAGTT GGTAGCTCTT GATCCGGCAA ACAAACCACC    4773
GCTGGTAGCG GTGGTTTTTT TGTTTGCAAG CAGCAGATTA CGCGCAGAAA AAAAGGATCT    4833
CAAGAAGATC CTTTGATCTT TTCTACGGGG TCTGACGCTC AGTGGAACGA AAACTCACGT    4893
TAAGGGATTT TGGTCATGAG ATTATCAAAA AGGATCTTCA CCTAGATCCT TTTAAATTAA    4953
AAATGAAGTT TTAAATCAAT CTAAAGTATA TATGAGTAAA CTTGGTCTGA CAGTTACCAA    5013
TGCTTAATCA GTGAGGCACC TATCTCAGCG ATCTGTCTAT TTCGTTCATC CATAGTTGCC    5073
TGACTCCCCG TCGTGTAGAT AACTACGATA CGGGAGGGCT TACCATCTGG CCCCAGTGCT    5133
GCAATGATAC CGCGAGACCC ACGCTCACCG GCTCCAGATT TATCAGCAAT AAACCAGCCA    5193
GCCGGAAGGG CCGAGCGCAG AAGTGGTCCT GCAACTTTAT CCGCCTCCAT CCAGTCTATT    5253
```

FIG._8E

```
AATTGTTGCC GGGAAGCTAG AGTAAGTAGT TCGCCAGTTA ATAGTTTGCG CAACGTTGTT    5313
GCCATTGCTG CAGGCATCGT GGTGTCACGC TCGTCGTTTG GTATGGCTTC ATTCAGCTCC    5373
GGTTCCCAAC GATCAAGGCG AGTTACATGA TCCCCCATGT TGTGCAAAAA AGCGGTTAGC    5433
TCCTTCGGTC CTCCGATCGT TGTCAGAAGT AAGTTGGCCG CAGTGTTATC ACTCATGGTT    5493
ATGGCAGCAC TGCATAATTC TCTTACTGTC ATGCCATCCG TAAGATGCTT TTCTGTGACT    5553
GGTGAGTACT CAACCAAGTC ATTCTGAGAA TAGTGTATGC GGCGACCGAG TTGCTCTTGC    5613
CCGGCGTCAA CACGGGATAA TACCGCGCCA CATAGCAGAA CTTTAAAAGT GCTCATCATT    5673
GGAAAACGTT CTTCGGGGCG AAAACTCTCA AGGATCTTAC CGCTGTTGAG ATCCAGTTCG    5733
ATGTAACCCA CTCGTGCACC CAACTGATCT TCAGCATCTT TTACTTTCAC CAGCGTTTCT    5793
GGGTGAGCAA AAACAGGAAG GCAAAATGCC GCAAAAAAGG GAATAAGGGC GACACGGAAA    5853
TGTTGAATAC TCATACTCTT CCTTTTTCAA TATTATTGAA GCATTTATCA GGGTTATTGT    5913
CTCATGAGCG GATACATATT TGAATGTATT TAGAAAAATA AACAAATAGG GGTTCCGCGC    5973
ACATTTCCCC GAAAAGTGCC ACCTGACGTC TAAGAAACCA TTATTATCAT GACATTAACC    6033
TATAAAAATA GGCGTATCAC GAGGCCCTTT CGTCTTCAA                           6072
```

FIG._8F

```
              10          20          30          40
F(ab)-12   DIQMTQSPSS  LSASVGDRVT  ITCSASQDIS  NYLNWYQQKP
MB1.6      DIQLTQSPSS  LSASVGDRVT  ITCSASQDIS  NYLNWYQQKP
H2305.6    DIQLTQSPSS  LSASVGDRVT  ITCSASQDIS  NYLNWYQQKP
Y0101      DIQLTQSPSS  LSASVGDRVT  ITCSASQDIS  NYLNWYQQKP
Y0192      DIQLTQSPSS  LSASVGDRVT  ITCRANEQLS  NYLNWYQQKP
                                      CDR-L1
              50          60          70          80
F(ab)-12   GKAPKVLIYF  TSSLHSGVPS  RFSGSGSGTD  FTLTISSLQP
MB1.6      GKAPKLLIYF  TSSLHSGVPS  RFSGSGSGTD  YTLTISSLQP
H2305.6    GKAPKVLIYF  TSSLHSGVPS  RFSGSGSGTD  YTLTISSLQP
Y0101      GKAPKVLIYF  TSSLHSGVPS  RFSGSGSGTD  FTLTISSLQP
Y0192      GKAPKVLIYF  TSSLHSGVPS  RFSGSGSGTD  FTLTISSLQP
                        CDR-L2
              90         100         110
F(ab)-12   EDFATYYCQQ  YSTVPWTFGQ  GTKVEIKRTV   (SEQ.ID NO:8)
MB1.6      EDFATYYCQQ  YSTVPWTFGQ  GTKVEIKRTV   (SEQ.ID NO:101)
H2305.6    EDFATYYCQQ  YSTVPWTFGQ  GTKVEIKRTV   (SEQ.ID NO:103)
Y0101      EDFATYYCQQ  YSTVPWTFGQ  GTKVEIKRTV   (SEQ.ID NO:105)
Y0192      EDFATYYCQQ  YSTVPWTFGQ  GTKVEIKRTV   (SEQ.ID NO:107)
                 CDR-L3
```

FIG._9A

```
              10          20          30          40
F(ab)-12   EVQLVESGGG  LVQPGGSLRL  SCAASGYTFT  NYGMNWVRQA
MB1.6      EVQLVESGGG  LVQPGGSLRL  SCAASGYTFT  NYGMNWIRQA
H2305.6    EVQLVESGGG  LVQPGGSLRL  SCAASGYTFT  NYGMNWIRQA
Y0101      EVQLVESGGG  LVQPGGSLRL  SCAASGYTFT  NYGMNWVRQA
Y0192      EVQLVESGGG  LVQPGGSLRL  SCAASGYTFT  NYGINWVRQA
                                      CDR-H1
              50          60          70          80
F(ab)-12   PGKGLEWVGW  INTYTGEPTY  AADFKRRFTF  SLDTSKSTAY
MB1.6      PGKGLEWVGW  INTYTGEPTY  AADFKRRFTF  SADTSSNIVY
H2305.6    PGKGLEWVGW  INTYTGEPTY  AADFKRRFTF  SADTSSNIVY
Y0101      PGKGLEWVGW  INTYTGEPTY  AADFKRRFTF  SLDTSKSTAY
Y0192      PGKGLEWVGW  INTYTGEPTY  AADFKRRFTF  SLDTSKSTAY
                        CDR-H2                    CDR-7
              90         100         110
F(ab)-12   LQMNSLRAED  TAVYYCAKYP  HYYGSSHWYF  DVWGQGTL    (SEQ.ID NO:7)
MB1.6      LQMNSLRAED  TAVYYCAKYP  HYYGSSHWYF  DVWGQGTL    (SEQ.ID NO:102)
H2305.6    LQMNSLRAED  TAVYYCAKYP  HYYGSSHWYF  DVWGQGTL    (SEQ.ID NO:104)
Y0101      LQMNSLRAED  TAVYYCAKYP  HYYGSSHWYF  DVWGQGTL    (SEQ.ID NO:106)
Y0192      LQMNSLRAED  TAVYYCAKYP  HYYGSSHWYF  DVWGQGTL    (SEQ.ID NO:108)
                           CDR-H3
```

FIG._9B

```
            10         20         30         40
F(ab)-12  DIQMTQSPSS LSASVGDRVT ITCSASQDIS NYLNWYQQKP
Y0243-1   DIQLTQSPSS LSASVGDRVT ITCRANEQLS NYLNWYQQKP
Y0238-3   DIQLTQSPSS LSASVGDRVT ITCRANEQLS NYLNWYQQKP
Y0313-1   DIQLTQSPSS LSASVGDRVT ITCRANEQLS NYLNWYQQKP
Y0317     DIQLTQSPSS LSASVGDRVT ITCSASQDIS NYLNWYQQKP
                                   CDR-L1
            50         60         70         80
F(ab)-12  GKAPKVLIYF TSSLHSGVPS RFSGSGSGTD FTLTISSLQP
Y0243-1   GKAPKVLIYF TSSLHSGVPS RFSGSGSGTD FTLTISSLQP
Y0238-3   GKAPKVLIYF TSSLHSGVPS RFSGSGSGTD FTLTISSLQP
Y0313-1   GKAPKVLIYF TSSLHSGVPS RFSGSGSGTD FTLTISSLQP
Y0317     GKAPKVLIYF TSSLHSGVPS RFSGSGSGTD FTLTISSLQP
                     CDR-L2
            90        100        110
F(ab)-12  EDFATYYCQQ YSTVPWTFGQ GTKVEIKRTV  (SEQ.ID NO:8)
Y0243-1   EDFATYYCQQ YSTVPWTFGQ GTKVEIKRTV  (SEQ.ID NO:109)
Y0238-3   EDFATYYCQQ YSTVPWTFGQ GTKVEIKRTV  (SEQ.ID NO:111)
Y0313-1   EDFATYYCQQ YSTVPWTFGQ GTKVEIKRTV  (SEQ.ID NO:113)
Y0317     EDFATYYCQQ YSTVPWTFGQ GTKVEIKRTV  (SEQ.ID NO:115)
                 CDR-L3
```

FIG. 10A

```
            10         20         30         40
F(ab)-12  EVQLVESGGG LVQPGGSLRL SCAASGYTFT NYGMNWVRQA
Y0243-1   EVQLVESGGG LVQPGGSLRL SCAASGYDFT HYGMNWVRQA
Y0238-3   EVQLVESGGG LVQPGGSLRL SCAASGYTFT NYGINWVRQA
Y0313-1   EVQLVESGGG LVQPGGSLRL SCAASGYDFT HYGMNWVRQA
Y0317     EVQLVESGGG LVQPGGSLRL SCAASGYDFT HYGMNWVRQA
                                      CDR-H1
            50         60         70         80
F(ab)-12  PGKGLEWVGW INTYTGEPTY AADFKRRFTF SLDTSKSTAY
Y0243-1   PGKGLEWVGW INTYTGEPTY AADFKRRFTF SLDTSKSTAY
Y0238-3   PGKGLEWVGW INTYTGEPTY AADFKRRFTF SLDTSKSTAY
Y0313-1   PGKGLEWVGW INTYTGEPTY AADFKRRFTF SLDTSKSTAY
Y0317     PGKGLEWVGW INTYTGEPTY AADFKRRFTF SLDTSKSTAY
                        CDR-H2              CDR-7
            90        100        110
F(ab)-12  LQMNSLRAED TAVYYCAKYP HYYGSSHWYF DVWGQGTL  (SEQ.ID NO:7)
Y0243-1   LQMNSLRAED TAVYYCAKYP HYYGSSHWYF DVWGQGTL  (SEQ.ID NO:110)
Y0238-3   LQMNSLRAED TAVYYCAKYP YYYGTSHWYF DVWGQGTL  (SEQ.ID NO:112)
Y0313-1   LQMNSLRAED TAVYYCAKYP YYYGTSHWYF DVWGQGTL  (SEQ.ID NO:114)
Y0317     LQMNSLRAED TAVYYCAKYP YYYGTSHWYF DVWGQGTL  (SEQ.ID NO:116)
                                  CDR-H3
```

FIG. 10B

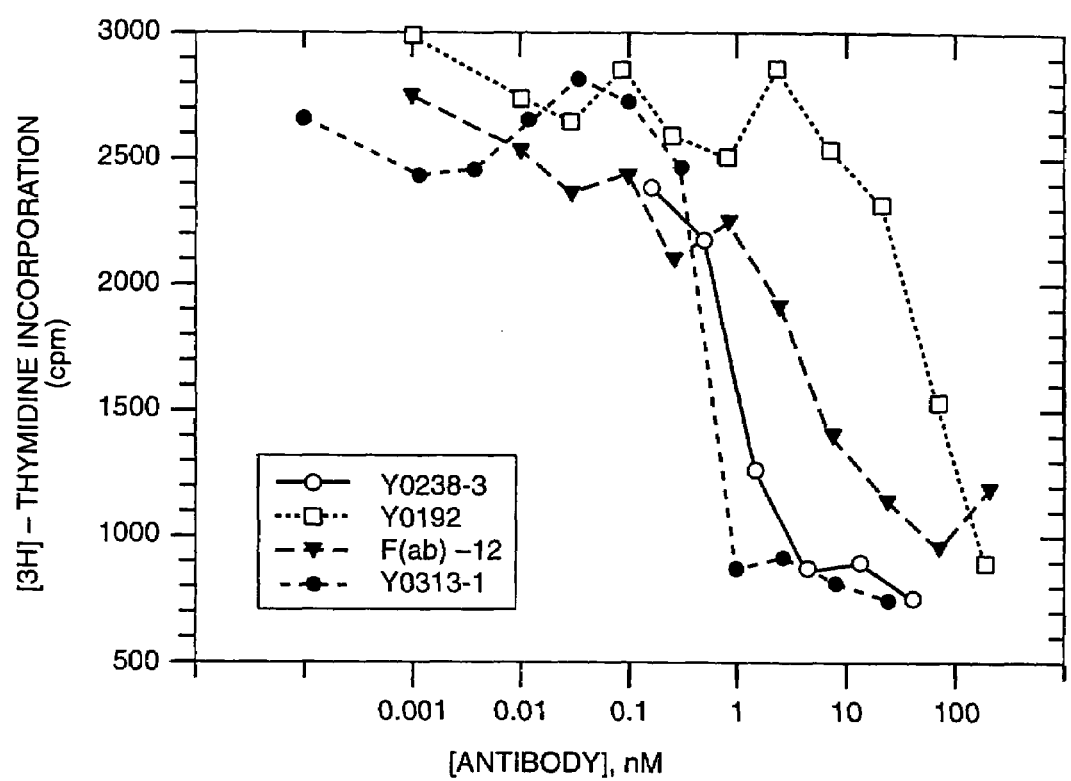
FIG._11

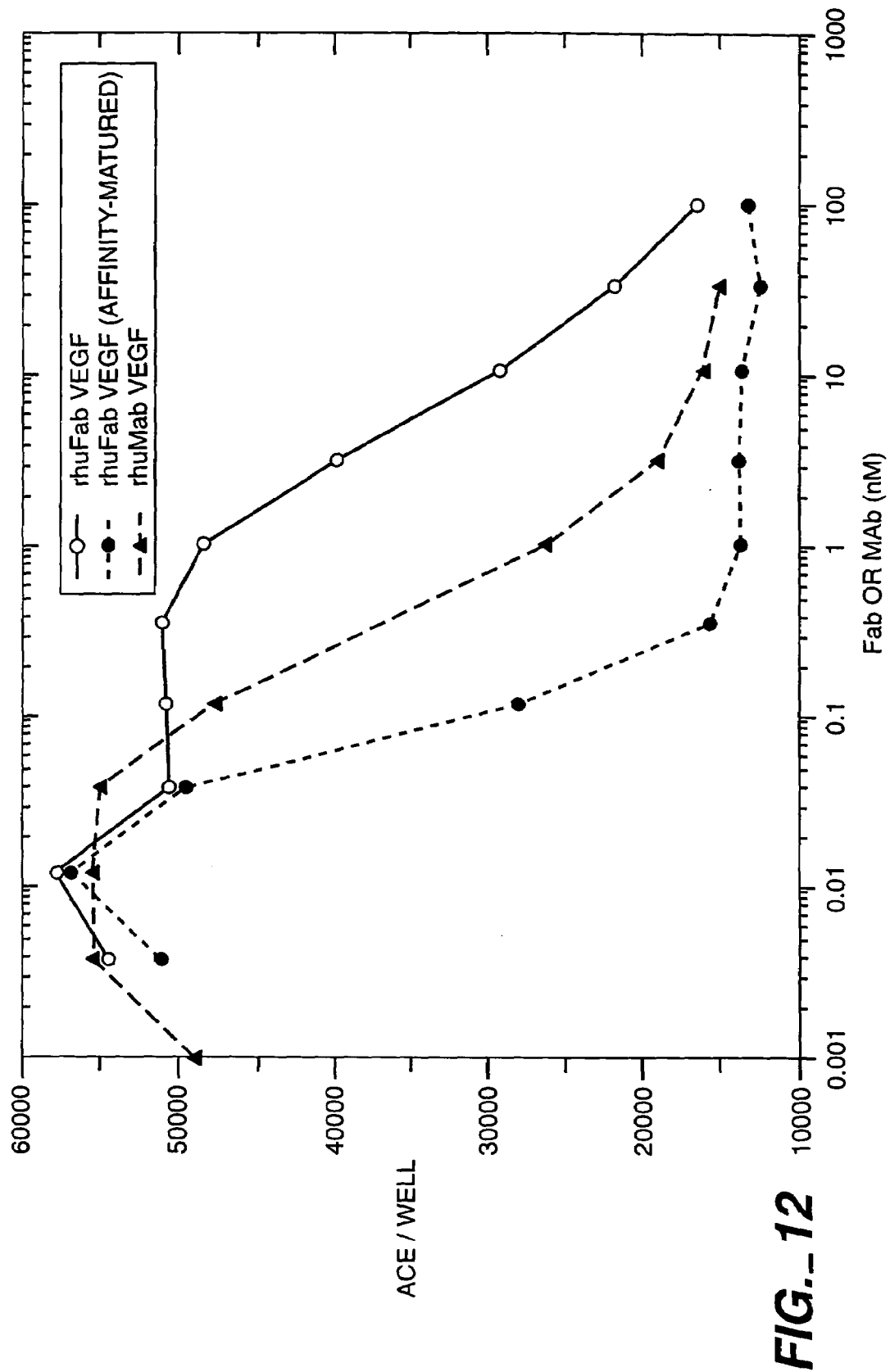
FIG._12

SEQUENCE LISTING (1) GENERAL INFORMATION:

(iii) NUMBER OF SEQUENCES: 131

(2) INFORMATION FOR SEQ ID NO: 1:

(i) SEQUENCE CHARACTERISTICS:
      (A) LENGTH: 10 amino acids (B) TYPE: Amino Acid
        (D) TOPOLOGY: Linear (xi) SEQUENCE DESCRIPTION: SEQ ID NO: 1:

Gly Tyr Thr Phe Thr Asn Tyr Gly Met Asn
 1               5                  10

(2) INFORMATION FOR SEQ ID NO: 2:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 2:

Trp Ile Asn Thr Tyr Thr Gly Glu Pro Thr Tyr Ala Ala Asp Phe
 1               5                  10                  15

Lys Arg (2) INFORMATION FOR SEQ ID NO: 3:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 3:

Tyr Pro His Tyr Tyr Gly Ser Ser His Trp Tyr Phe Asp Val
 1               5                  10

(2) INFORMATION FOR SEQ ID NO: 4:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 4:

Ser Ala Ser Gln Asp Ile Ser Asn Tyr Leu Asn
 1               5                  10

(2) INFORMATION FOR SEQ ID NO: 5:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 5:

Phe Thr Ser Ser Leu His Ser
 1               5

(2) INFORMATION FOR SEQ ID NO: 6:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO: 6:

Gln Gln Tyr Ser Thr Val Pro Trp Thr
 1               5

(2) INFORMATION FOR SEQ ID NO: 7:

(i) SEQUENCE CHARACTERISTICS:

(A) LENGTH: 118 amino acids
        (B) TYPE: Amino Acid
        (D) TOPOLOGY: Linear (xi) SEQUENCE DESCRIPTION: SEQ ID NO: 7:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu
                110                 115

(2) INFORMATION FOR SEQ ID NO: 8:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 8:

Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
                110

(2) INFORMATION FOR SEQ ID NO: 9:

(i) SEQUENCE CHARACTERISTICS:
        (A) LENGTH: 123 amino acids
        (B) TYPE: Amino Acid
        (D) TOPOLOGY: Linear (xi) SEQUENCE DESCRIPTION: SEQ ID NO: 9:

Glu Ile Gln Leu Val Gln Ser Gly Pro Glu Leu Lys Gln Pro Gly
 1               5                  10                  15

Glu Thr Val Arg Ile Ser Cys Lys Ala Ser Gly Tyr Thr Phe Thr
                20                  25                  30

```
Asn Tyr Gly Met Asn Trp Val Lys Gln Ala Pro Gly Lys Gly Leu
                 35                  40                  45

Lys Trp Met Gly Trp Ile Asn Thr Tyr Thr Gly Glu Pro Thr Tyr
         50                  55                  60

Ala Ala Asp Phe Lys Arg Arg Phe Thr Phe Ser Leu Glu Thr Ser
             65                  70                  75

Ala Ser Thr Ala Tyr Leu Gln Ile Ser Asn Leu Lys Asn Asp Asp
             80                  85                  90

Thr Ala Thr Tyr Phe Cys Ala Lys Tyr Pro His Tyr Tyr Gly Ser
             95                 100                 105

Ser His Trp Tyr Phe Asp Val Trp Gly Ala Gly Thr Thr Val Thr
                110                 115                 120

Val Ser Ser (2) INFORMATION FOR SEQ ID NO: 10:

(i) SEQUENCE CHARACTERISTICS:
        (A) LENGTH: 108 amino acids
        (B) TYPE: Amino Acid
        (D) TOPOLOGY: Linear (xi) SEQUENCE DESCRIPTION: SEQ ID NO: 10:

Asp Ile Gln Met Thr Gln Thr Thr Ser Ser Leu Ser Ala Ser Leu
 1               5                  10                  15

Gly Asp Arg Val Ile Ile Ser Cys Ser Ala Ser Gln Asp Ile Ser
                 20                  25                  30

Asn Tyr Leu Asn Trp Tyr Gln Gln Lys Pro Asp Gly Thr Val Lys
                 35                  40                  45

Val Leu Ile Tyr Phe Thr Ser Ser Leu His Ser Gly Val Pro Ser
             50                  55                  60

Arg Phe Ser Gly Ser Gly Ser Gly Thr Asp Tyr Ser Leu Thr Ile
             65                  70                  75

Ser Asn Leu Glu Pro Glu Asp Ile Ala Thr Tyr Tyr Cys Gln Gln
             80                  85                  90

Tyr Ser Thr Val Pro Trp Thr Phe Gly Gly Gly Thr Lys Leu Glu
             95                 100                 105

Ile Lys Arg (2) INFORMATION FOR SEQ ID NO: 11:

(i) SEQUENCE CHARACTERISTICS:
        (A) LENGTH: 113 amino acids
        (B) TYPE: Amino Acid
        (D) TOPOLOGY: Linear (xi) SEQUENCE DESCRIPTION: SEQ ID NO: 11:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                 20                  25                  30

Ser Tyr Ala Met Ser Trp Val Arg Gln Ala Pro Gly Lys Gly Leu
                 35                  40                  45

Glu Trp Val Ser Val Ile Ser Gly Asp Gly Gly Ser Thr Tyr Tyr
             50                  55                  60

Ala Asp Ser Val Lys Gly Arg Phe Thr Ile Ser Arg Asp Asn Ser
             65                  70                  75
```

-continued

```
Lys Asn Thr Leu Tyr Leu Gln Met Asn Ser Leu Arg Ala Glu Asp
            80                  85                  90

Thr Ala Val Tyr Tyr Cys Ala Arg Gly Phe Asp Tyr Trp Gly Gln
            95                 100                 105

Gly Thr Leu Val Thr Val Ser Ser
            110
```

(2) INFORMATION FOR SEQ ID NO: 12:

(i) SEQUENCE CHARACTERISTICS:
        (A) LENGTH: 108 amino acids
        (B) TYPE: Amino Acid
        (D) TOPOLOGY: Linear (xi) SEQUENCE DESCRIPTION: SEQ ID NO: 12:

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
            20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Asn Ser Leu Pro Trp Thr Phe Gly Gln Gly Thr Lys Val Glu
            95                 100                 105

Ile Lys Arg
```

(2) INFORMATION FOR SEQ ID NO: 13:

(i) SEQUENCE CHARACTERISTICS:
        (A) LENGTH: 107 amino acids
        (B) TYPE: Amino Acid
        (D) TOPOLOGY: Linear (xi) SEQUENCE DESCRIPTION: SEQ ID NO: 13:

```
Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
            20                  25                  30

Asn Tyr Leu Asn Trp Tyr Gln Gln Lys Pro Gly Lys Ala Pro Lys
            35                  40                  45

Leu Leu Ile Tyr Phe Thr Ser Ser Leu His Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Ser Thr Val Pro Trp Thr Phe Gly Gln Gly Thr Lys Val Glu
            95                 100                 105

Ile Lys
```

(2) INFORMATION FOR SEQ ID NO: 14:

(i) SEQUENCE CHARACTERISTICS:

(A) LENGTH: 123 amino acids
        (B) TYPE: Amino Acid
        (D) TOPOLOGY: Linear (xi) SEQUENCE DESCRIPTION: SEQ ID NO: 14:

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Asn Tyr Gly Met Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Ile Ser Arg Asp Asn Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Tyr Pro His Tyr Tyr Gly Ser
                 95                 100                 105

Ser His Trp Tyr Phe Asp Val Trp Gly Gln Gly Thr Leu Val Thr
                110                 115                 120

Val Ser Ser (2) INFORMATION FOR SEQ ID NO: 15:

(i) SEQUENCE CHARACTERISTICS:
        (A) LENGTH: 107 amino acids
        (B) TYPE: Amino Acid
        (D) TOPOLOGY: Linear (xi) SEQUENCE DESCRIPTION: SEQ ID NO: 15:

Asp Ile Gln Met Thr Gln Ser Pro Ser Ser Leu Ser Ala Ser Val
  1               5                  10                  15

Gly Asp Arg Val Thr Ile Thr Cys Ser Ala Ser Gln Asp Ile Ser
                 20                  25                  30

Asn Tyr Leu Asn Trp Tyr Gln Gln Lys Pro Gly Lys Ala Pro Lys
                 35                  40                  45

Leu Leu Ile Tyr Phe Thr Ser Ser Leu His Ser Gly Val Pro Ser
                 50                  55                  60

Arg Phe Ser Gly Ser Gly Ser Gly Thr Asp Tyr Thr Leu Thr Ile
                 65                  70                  75

Ser Ser Leu Gln Pro Glu Asp Phe Ala Thr Tyr Tyr Cys Gln Gln
                 80                  85                  90

Tyr Ser Thr Val Pro Trp Thr Phe Gly Gln Gly Thr Lys Val Glu
                 95                 100                 105

Ile Lys (2) INFORMATION FOR SEQ ID NO: 16:

(i) SEQUENCE CHARACTERISTICS:
        (A) LENGTH: 123 amino acids
        (B) TYPE: Amino Acid
        (D) TOPOLOGY: Linear (xi) SEQUENCE DESCRIPTION: SEQ ID NO: 16:

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr

```
                    20                  25                  30
Asn Tyr Gly Met Asn Trp Ile Arg Gln Ala Pro Gly Lys Gly Leu
                35                  40                  45
Glu Trp Val Gly Trp Ile Asn Thr Tyr Thr Gly Glu Pro Thr Tyr
                50                  55                  60
Ala Ala Asp Phe Lys Arg Arg Phe Thr Ile Ser Leu Asp Thr Ser
                65                  70                  75
Ala Ser Thr Val Tyr Leu Gln Met Asn Ser Leu Arg Ala Glu Asp
                80                  85                  90
Thr Ala Val Tyr Tyr Cys Ala Lys Tyr Pro His Tyr Tyr Gly Ser
                95                 100                 105
Ser His Trp Tyr Phe Asp Val Trp Gly Gln Gly Thr Leu Val Thr
               110                 115                 120
Val Ser Ser
```

(2) INFORMATION FOR SEQ ID NO: 17:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 17:

```
Pro Lys Asn Ser Ser Met Ile Ser Asn Thr Pro
 1               5                  10
```

(2) INFORMATION FOR SEQ ID NO: 18:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 18:

```
His Gln Ser Leu Gly Thr Gln
 1               5
```

(2) INFORMATION FOR SEQ ID NO: 19:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 19:

```
His Gln Asn Leu Ser Asp Gly Lys
 1               5
```

(2) INFORMATION FOR SEQ ID NO: 20:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 20:

```
His Gln Asn Ile Ser Asp Gly Lys
 1               5
```

(2) INFORMATION FOR SEQ ID NO: 21:

(i) SEQUENCE CHARACTERISTICS:
        (A) LENGTH: 8 amino acids (B) TYPE: Amino Acid
        (D) TOPOLOGY: Linear (xi) SEQUENCE DESCRIPTION: SEQ ID NO: 21:

Val Ile Ser Ser His Leu Gly Gln
 1               5

(2) INFORMATION FOR SEQ ID NO: 22:

(i) SEQUENCE CHARACTERISTICS:
        (A) LENGTH: 66 base pairs
        (B) TYPE: Nucleic Acid
        (C) STRANDEDNESS: Single
        (D) TOPOLOGY: Linear (xi) SEQUENCE DESCRIPTION: SEQ ID NO: 22:

GATTTCAAAC GTCGTNYTAC TWTTTCTAGA GACAACTCCA AAAACACABY           50

TTACCTGCAG ATGAAC                                                66

(2) INFORMATION FOR SEQ ID NO: 23:

(i) SEQUENCE CHARACTERISTICS:
        (A) LENGTH: 66 base pairs
        (B) TYPE: Nucleic Acid
        (C) STRANDEDNESS: Single
        (D) TOPOLOGY: Linear (xi) SEQUENCE DESCRIPTION: SEQ ID NO: 23:

GATTTCAAAC GTCGTNYTAC TWTTTCTTTA GACACCTCCG CAAGCACABY           50

TTACCTGCAG ATGAAC                                                66

(2) INFORMATION FOR SEQ ID NO: 24:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO: 24:

AGCCTGCGCG CTGAGGACAC TGCCGTCTAT TACTGTDYAA RGTACCCCCA           50

CTATTATGGG                                                       60

(2) INFORMATION FOR SEQ ID NO: 25:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 25:

CTCAGCGCGC AGGCTGTTCA TCTGCAGGTA                                 30

(2) INFORMATION FOR SEQ ID NO: 26:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO: 26:

GCTGATATCC AGTTGACCCA GTCCCCG                                    27

(2) INFORMATION FOR SEQ ID NO: 27:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO: 27:

```
TCTGGGACGG ATTACACTCT GACCATC                                              27
```

(2) INFORMATION FOR SEQ ID NO: 28:

(i) SEQUENCE CHARACTERISTICS:
        (A) LENGTH: 75 base pairs
        (B) TYPE: Nucleic Acid
        (C) STRANDEDNESS: Single
        (D) TOPOLOGY: Linear (xi) SEQUENCE DESCRIPTION: SEQ ID NO: 28:

```
CGTTTGTCCT GTGCARYTTC TGGCTATACC TTCACCAACT ATGGTATGAA                     50

CTGGRTCCGT CAGGCCCCGG GTAAG                                                75
```

(2) INFORMATION FOR SEQ ID NO: 29:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO: 29:

```
GATATCCAGT TGACCCAGTC CCCG                                                 24
```

(2) INFORMATION FOR SEQ ID NO: 30:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 30:

```
GCTCCGAAAG TACTGATTTA C                                                    21
```

(2) INFORMATION FOR SEQ ID NO: 31:

(i) SEQUENCE CHARACTERISTICS:
        (A) LENGTH: 54 base pairs
        (B) TYPE: Nucleic Acid
        (C) STRANDEDNESS: Single
        (D) TOPOLOGY: Linear (xi) SEQUENCE DESCRIPTION: SEQ ID NO: 31:

```
CGTCGTTTCA CTTTTTCTGC AGACACCTCC AGCAACACAG TATACCTGCA                     50

GATG                                                                       54
```

(2) INFORMATION FOR SEQ ID NO: 32:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO: 32:

```
CTATTACTGT GCAAAGTACC CCCAC                                         25

(2) INFORMATION FOR SEQ ID NO: 33:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO: 33:

GGGACGGATT TCACTCTGAC CATC                                          24

(2) INFORMATION FOR SEQ ID NO: 34:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (xi) SEQUENCE DESCRIPTION: SEQ ID NO: 34:

GGTATGAACT GGGTCCGTCA GGCCCC                                        26

(2) INFORMATION FOR SEQ ID NO: 35:

(i) SEQUENCE CHARACTERISTICS:
        (A) LENGTH: 57 base pairs
        (B) TYPE: Nucleic Acid
        (C) STRANDEDNESS: Single
        (D) TOPOLOGY: Linear (xi) SEQUENCE DESCRIPTION: SEQ ID NO: 35:

CGTCGTTTCA CTTTTTCTTT AGACACCTCC AAAAGCACAG CATACCTGCA              50

GATGAAC                                                             57

(2) INFORMATION FOR SEQ ID NO: 36:

(i) SEQUENCE CHARACTERISTICS:
        (A) LENGTH: 53 base pairs
        (B) TYPE: Nucleic Acid
        (C) STRANDEDNESS: Single
        (D) TOPOLOGY: Linear (xi) SEQUENCE DESCRIPTION: SEQ ID NO: 36:

GGGTCACCAT CACCTGCTAA GCATAATAAT AATAAAGCAA CTATTTAAAC              50

TGG                                                                 53

(2) INFORMATION FOR SEQ ID NO: 37:

(i) SEQUENCE CHARACTERISTICS:
        (A) LENGTH: 52 base pairs
        (B) TYPE: Nucleic Acid
        (C) STRANDEDNESS: Single
        (D) TOPOLOGY: Linear (xi) SEQUENCE DESCRIPTION: SEQ ID NO: 37:

GCGCAAGTCA GGATATTTAA TAATAATAAT AATGGTATCA ACAGAAACCA              50

GG                                                                  52

(2) INFORMATION FOR SEQ ID NO: 38:

(i) SEQUENCE CHARACTERISTICS:
        (A) LENGTH: 48 base pairs
```

```
            (B) TYPE: Nucleic Acid
            (C) STRANDEDNESS: Single
            (D) TOPOLOGY: Linear (xi) SEQUENCE DESCRIPTION: SEQ ID NO: 38:

GTCTATTACT GTGCAAAGTA ATAACACTAA TAAGGGAGCA GCCACTGG                48

(2) INFORMATION FOR SEQ ID NO: 39:

(i) SEQUENCE CHARACTERISTICS:
            (A) LENGTH: 49 base pairs
            (B) TYPE: Nucleic Acid
            (C) STRANDEDNESS: Single
            (D) TOPOLOGY: Linear (xi) SEQUENCE DESCRIPTION: SEQ ID NO: 39:

GGTACCCCCA CTATTATTAA TAATAATAAT GGTATTTCGA CGTCTGGGG              49

(2) INFORMATION FOR SEQ ID NO: 40:

(i) SEQUENCE CHARACTERISTICS:
            (A) LENGTH: 53 base pairs
            (B) TYPE: Nucleic Acid
            (C) STRANDEDNESS: Single
            (D) TOPOLOGY: Linear (xi) SEQUENCE DESCRIPTION: SEQ ID NO: 40:

CACTATTATG GGAGCAGCCA CTAATAATAA TAAGTCTGGG TCAAGGAACC             50

CTG                                                                53

(2) INFORMATION FOR SEQ ID NO: 41:

(i) SEQUENCE CHARACTERISTICS:
            (A) LENGTH: 53 base pairs
            (B) TYPE: Nucleic Acid
            (C) STRANDEDNESS: Single
            (D) TOPOLOGY: Linear (xi) SEQUENCE DESCRIPTION: SEQ ID NO: 41:

TCCTGTGCAG CTTCTGGCTA ATAATTCTAA TAATAAGGTA TGAACTGGGT             50

CCG                                                                53

(2) INFORMATION FOR SEQ ID NO: 42:

(i) SEQUENCE CHARACTERISTICS:
            (A) LENGTH: 52 base pairs
            (B) TYPE: Nucleic Acid
            (C) STRANDEDNESS: Single
            (D) TOPOLOGY: Linear (xi) SEQUENCE DESCRIPTION: SEQ ID NO: 42:

GAATGGGTTG GATGGATTAA CTAATAATAA GGTTAACCGA CCTATGCTGC             50

GG                                                                 52

(2) INFORMATION FOR SEQ ID NO: 43:

(i) SEQUENCE CHARACTERISTICS:
            (A) LENGTH: 49 base pairs
            (B) TYPE: Nucleic Acid
            (C) STRANDEDNESS: Single
            (D) TOPOLOGY: Linear (xi) SEQUENCE DESCRIPTION: SEQ ID NO: 43:

CTGTGCAAAG TACCCGTAAT ATTAATAATA ATAACACTGG TATTTCGAC              49
```

(2) INFORMATION FOR SEQ ID NO: 44:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 44:

CGTTTCACTT TTTCTTAAGA CTAATCCAAA TAAACAGCAT ACCTGCAG                48

(2) INFORMATION FOR SEQ ID NO: 45:

(i) SEQUENCE CHARACTERISTICS:
        (A) LENGTH: 46 base pairs
        (B) TYPE: Nucleic Acid
        (C) STRANDEDNESS: Single
        (D) TOPOLOGY: Linear (xi) SEQUENCE DESCRIPTION: SEQ ID NO: 45:

GAATGGGTTG GATGGATTTA ATAATAATAA GGTGAACCGA CCTATG                 46

(2) INFORMATION FOR SEQ ID NO: 46:

(i) SEQUENCE CHARACTERISTICS:
        (A) LENGTH: 53 base pairs
        (B) TYPE: Nucleic Acid
        (C) STRANDEDNESS: Single
        (D) TOPOLOGY: Linear (xi) SEQUENCE DESCRIPTION: SEQ ID NO: 46:

GGGTCACCAT CACCTGCNNS GCANNSNNSN NSNNSAGCAA CTATTTAAAC              50
TGG                                                                53

(2) INFORMATION FOR SEQ ID NO: 47:

(i) SEQUENCE CHARACTERISTICS:
        (A) LENGTH: 52 base pairs
        (B) TYPE: Nucleic Acid
        (C) STRANDEDNESS: Single
        (D) TOPOLOGY: Linear (xi) SEQUENCE DESCRIPTION: SEQ ID NO: 47:

GCGCAAGTCA GGATATTNNS NNSNNSNNSN NSTGGTATCA ACAGAAACCA              50
GG                                                                 52

(2) INFORMATION FOR SEQ ID NO: 48:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 48:

GTCTATTACT GTGCAAAGNN SNNSCACNNS NNSGGGAGCA GCCACTGG                48

(2) INFORMATION FOR SEQ ID NO: 49:

(i) SEQUENCE CHARACTERISTICS:
        (A) LENGTH: 49 base pairs
        (B) TYPE: Nucleic Acid
        (C) STRANDEDNESS: Single
        (D) TOPOLOGY: Linear (xi) SEQUENCE DESCRIPTION: SEQ ID NO: 49:

```
GGTACCCCCA CTATTATNNS NNSNNSNNST GGTATTTCGA CGTCTGGGG                    49

(2) INFORMATION FOR SEQ ID NO: 50:

(i) SEQUENCE CHARACTERISTICS:
        (A) LENGTH: 54 base pairs
        (B) TYPE: Nucleic Acid
        (C) STRANDEDNESS: Single
        (D) TOPOLOGY: Linear (xi) SEQUENCE DESCRIPTION: SEQ ID NO: 50:

CACTATTATG GGAGCAGCCA CNNSNNSNNS NNSGTCTGGG GTCAAGGAAC                   50

CCTG                                                                    54

(2) INFORMATION FOR SEQ ID NO: 51:

(i) SEQUENCE CHARACTERISTICS:
        (A) LENGTH: 53 base pairs
        (B) TYPE: Nucleic Acid
        (C) STRANDEDNESS: Single
        (D) TOPOLOGY: Linear (xi) SEQUENCE DESCRIPTION: SEQ ID NO: 51:

TCCTGTGCAG CTTCTGGCNN SNNSTTCNNS NNSNNSGGTA TGAACTGGGT                   50

CCG                                                                     53

(2) INFORMATION FOR SEQ ID NO: 52:

(i) SEQUENCE CHARACTERISTICS:
        (A) LENGTH: 52 base pairs
        (B) TYPE: Nucleic Acid
        (C) STRANDEDNESS: Single
        (D) TOPOLOGY: Linear (xi) SEQUENCE DESCRIPTION: SEQ ID NO: 52:

GAATGGGTTG GATGGATTAA CNNSNNSNNS GGTNNSCCGA CCTATGCTGC                   50

GG                                                                      52

(2) INFORMATION FOR SEQ ID NO: 53:

(i) SEQUENCE CHARACTERISTICS:
        (A) LENGTH: 49 base pairs
        (B) TYPE: Nucleic Acid
        (C) STRANDEDNESS: Single
        (D) TOPOLOGY: Linear (xi) SEQUENCE DESCRIPTION: SEQ ID NO: 53:

CTGTGCAAAG TACCCGNNST ATNNSNNSNN SNNSCACTGG TATTTCGAC                    49

(2) INFORMATION FOR SEQ ID NO: 54:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 54:

CGTTTCACTT TTTCTNNSGA CNNSTCCAAA NNSACAGCAT ACCTGCAG                     48

(2) INFORMATION FOR SEQ ID NO: 55:

(i) SEQUENCE CHARACTERISTICS:
        (A) LENGTH: 46 base pairs
```

(B) TYPE: Nucleic Acid
        (C) STRANDEDNESS: Single
        (D) TOPOLOGY: Linear (xi) SEQUENCE DESCRIPTION: SEQ ID NO: 55:

GAATGGGTTG GATGGATTNN SNNSNNSNNS GGTGAACCGA CCTATG                46

(2) INFORMATION FOR SEQ ID NO: 56:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 56:

Tyr Pro Tyr Tyr Arg Gly Thr Ser His Trp Tyr Phe Asp
 1               5                  10

(2) INFORMATION FOR SEQ ID NO: 57:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 57:

Tyr Pro Tyr Tyr Ile Asn Lys Ser His Trp Tyr Phe Asp
 1               5                  10

(2) INFORMATION FOR SEQ ID NO: 58:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 58:

Tyr Pro Tyr Tyr Tyr Gly Thr Ser His Trp Tyr Phe Asp
 1               5                  10

(2) INFORMATION FOR SEQ ID NO: 59:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 59:

Tyr Pro Tyr Tyr Tyr Asn Gln Ser His Trp Tyr Phe Asp
 1               5                  10

(2) INFORMATION FOR SEQ ID NO: 60:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 60:

Tyr Pro Tyr Tyr Ile Ala Lys Ser His Trp Tyr Phe Asp
 1               5                  10

(2) INFORMATION FOR SEQ ID NO: 61:

(i) SEQUENCE CHARACTERISTICS:
        (A) LENGTH: 13 amino acids
        (B) TYPE: Amino Acid (D) TOPOLOGY: Linear (xi) SEQUENCE DESCRIPTION: SEQ ID NO: 61:

Tyr Pro Tyr Tyr Arg Asp Asn Ser His Trp Tyr Phe Asp
 1               5                  10

(2) INFORMATION FOR SEQ ID NO: 62:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 62:

Tyr Pro Tyr Tyr Trp Gly Thr Ser His Trp Tyr Phe Asp
 1               5                  10

(2) INFORMATION FOR SEQ ID NO: 63:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 63:

Tyr Pro Tyr Tyr Arg Gln Asn Ser His Trp Tyr Phe Asp
 1               5                  10

(2) INFORMATION FOR SEQ ID NO: 64:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 64:

Tyr Pro Tyr Tyr Arg Gln Ser Ser His Trp Tyr Phe Asp
 1               5                  10

(2) INFORMATION FOR SEQ ID NO: 65:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 65:

Tyr Pro Tyr Tyr Arg Asn Thr Ser His Trp Tyr Phe Asp
 1               5                  10

(2) INFORMATION FOR SEQ ID NO: 66:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 66:

Tyr Pro Tyr Tyr Lys Asn Thr Ser His Trp Tyr Phe Asp
 1               5                  10

(2) INFORMATION FOR SEQ ID NO: 67:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 67:

Tyr Pro Tyr Tyr Ile Glu Arg Ser His Trp Tyr Phe Asp
  1               5                  10

(2) INFORMATION FOR SEQ ID NO: 68:

(i) SEQUENCE CHARACTERISTICS:
            (A) LENGTH: 13 amino acids
            (B) TYPE: Amino Acid
            (D) TOPOLOGY: Linear (xi) SEQUENCE DESCRIPTION: SEQ ID NO: 68:

Tyr Pro Tyr Tyr Arg Asn Ala Ser His Trp Tyr Phe Asp
  1               5                  10

(2) INFORMATION FOR SEQ ID NO: 69:

(i) SEQUENCE CHARACTERISTICS:
            (A) LENGTH: 13 amino acids
            (B) TYPE: Amino Acid
            (D) TOPOLOGY: Linear (xi) SEQUENCE DESCRIPTION: SEQ ID NO: 69:

Tyr Pro Tyr Tyr Thr Thr Arg Ser His Trp Tyr Phe Asp
  1               5                  10

(2) INFORMATION FOR SEQ ID NO: 70:

(i) SEQUENCE CHARACTERISTICS:
            (A) LENGTH: 13 amino acids
            (B) TYPE: Amino Acid
            (D) TOPOLOGY: Linear (xi) SEQUENCE DESCRIPTION: SEQ ID NO: 70:

Tyr Pro Tyr Tyr Glu Gly Ser Ser His Trp Tyr Phe Asp
  1               5                  10

(2) INFORMATION FOR SEQ ID NO: 71:

(i) SEQUENCE CHARACTERISTICS:
            (A) LENGTH: 13 amino acids
            (B) TYPE: Amino Acid
            (D) TOPOLOGY: Linear (xi) SEQUENCE DESCRIPTION: SEQ ID NO: 71:

Tyr Pro Tyr Tyr Arg Gln Arg Gly His Trp Tyr Phe Asp
  1               5                  10

(2) INFORMATION FOR SEQ ID NO: 72:

(i) SEQUENCE CHARACTERISTICS:
            (A) LENGTH: 13 amino acids
            (B) TYPE: Amino Acid
            (D) TOPOLOGY: Linear (xi) SEQUENCE DESCRIPTION: SEQ ID NO: 72:

Tyr Pro Tyr Tyr Thr Gly Arg Ser His Trp Tyr Phe Asp
  1               5                  10

(2) INFORMATION FOR SEQ ID NO: 73:

(i) SEQUENCE CHARACTERISTICS:
            (A) LENGTH: 13 amino acids
            (B) TYPE: Amino Acid
            (D) TOPOLOGY: Linear (xi) SEQUENCE DESCRIPTION: SEQ ID NO: 73:

Tyr Pro Tyr Tyr Thr Asn Thr Ser His Trp Tyr Phe Asp
 1               5                  10

(2) INFORMATION FOR SEQ ID NO: 74:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 74:

Tyr Pro Tyr Tyr Arg Lys Gly Ser His Trp Tyr Phe Asp
 1               5                  10

(2) INFORMATION FOR SEQ ID NO: 75:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 75:

Tyr Pro Tyr Tyr Thr Gly Ser Ser His Trp Tyr Phe Asp
 1               5                  10

(2) INFORMATION FOR SEQ ID NO: 76:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 76:

Tyr Pro Tyr Tyr Arg Ser Gly Ser His Trp Tyr Phe Asp
 1               5                  10

(2) INFORMATION FOR SEQ ID NO: 77:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 77:

Tyr Pro Tyr Tyr Thr Asn Arg Ser His Trp Tyr Phe Asp
 1               5                  10

(2) INFORMATION FOR SEQ ID NO: 78:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 78:

Tyr Pro Tyr Tyr Arg Asn Ser Ser His Trp Tyr Phe Asp
 1               5                  10

(2) INFORMATION FOR SEQ ID NO: 79:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 79:

```
Tyr Pro Tyr Tyr Lys Glu Ser Ser His Trp Tyr Phe Asp
 1               5                   10
```

(2) INFORMATION FOR SEQ ID NO: 80:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 80:

```
Tyr Pro Tyr Tyr Arg Asp Ala Ser His Trp Tyr Phe Asp
 1               5                   10
```

(2) INFORMATION FOR SEQ ID NO: 81:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 81:

```
Tyr Pro Tyr Tyr Arg Gln Lys Gly His Trp Tyr Phe Asp
 1               5                   10
```

(2) INFORMATION FOR SEQ ID NO: 82:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 82:

```
Tyr Pro Tyr Tyr Lys Gly Gly Ser His Trp Tyr Phe Asp
 1               5                   10
```

(2) INFORMATION FOR SEQ ID NO: 83:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 83:

```
Tyr Pro Tyr Tyr Tyr Gly Ala Ser His Trp Tyr Phe Asp
 1               5                   10
```

(2) INFORMATION FOR SEQ ID NO: 84:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 84:

```
Tyr Pro Tyr Tyr Arg Gly Glu Ser His Trp Tyr Phe Asp
 1               5                   10
```

(2) INFORMATION FOR SEQ ID NO: 85:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 85:

```
Tyr Pro Tyr Tyr Arg Ser Thr Ser His Trp Tyr Phe Asp
  1               5                  10
```

(2) INFORMATION FOR SEQ ID NO: 86:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 86:

```
Gly Tyr Asp Phe Thr His Tyr Gly Met Asn
  1               5                  10
```

(2) INFORMATION FOR SEQ ID NO: 87:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 87:

```
Gly Tyr Glu Phe Gln His Tyr Gly Met Asn
  1               5                  10
```

(2) INFORMATION FOR SEQ ID NO: 88:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 88:

```
Gly Tyr Glu Phe Thr His Tyr Gly Met Asn
  1               5                  10
```

(2) INFORMATION FOR SEQ ID NO: 89:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 89:

```
Gly Tyr Asp Phe Gly His Tyr Gly Met Asn
  1               5                  10
```

(2) INFORMATION FOR SEQ ID NO: 90:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 90:

```
Gly Tyr Asp Phe Ser His Tyr Gly Met Asn
  1               5                  10
```

(2) INFORMATION FOR SEQ ID NO: 91:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 91:

```
Gly Tyr Glu Phe Ser His Tyr Gly Met Asn
```

(2) INFORMATION FOR SEQ ID NO: 92:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 92:

Phe Ser Val Asp Val Ser Lys Ser Thr Ala
 1               5                  10

(2) INFORMATION FOR SEQ ID NO: 93:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 93:

Phe Ser Leu Asp Lys Ser Lys Ser Thr Ala
 1               5                  10

(2) INFORMATION FOR SEQ ID NO: 94:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 94:

Phe Ser Leu Asp Val Trp Lys Ser Thr Ala
 1               5                  10

(2) INFORMATION FOR SEQ ID NO: 95:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 95:

Phe Ser Ile Asp Lys Ser Lys Ser Thr Ala
 1               5                  10

(2) INFORMATION FOR SEQ ID NO: 96:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO: 96:

GCAAAGTACC CGTACTATTA TGGGACGAGC CACTGGTATT TC                          42

(2) INFORMATION FOR SEQ ID NO: 97:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 97:

GTCACCATCA CCTGCAGCGC AAGTCAGGAT ATTAGCAACT ATTTAAAC                     48

(2) INFORMATION FOR SEQ ID NO: 98:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 98:

| | |
|---|---:|
| CCGTACTATT ATGGGAGCAG CCACTGGTAT TTC | 33 |

(2) INFORMATION FOR SEQ ID NO: 99:

(i) SEQUENCE CHARACTERISTICS:
        (A) LENGTH: 6072 base pairs
        (B) TYPE: Nucleic Acid
        (C) STRANDEDNESS: Single
        (D) TOPOLOGY: Linear (xi) SEQUENCE DESCRIPTION: SEQ ID NO: 99:

| | |
|---|---:|
| GAATTCAACT TCTCCATACT TTGGATAAGG AAATACAGAC ATGAAAAATC | 50 |
| TCATTGCTGA GTTGTTATTT AAGCTTTGGA GATTATCGTC ACTGCAATGC | 100 |
| TTCGCAATAT GGCGCAAAAT GACCAACAGC GGTTGATTGA TCAGGTAGAG | 150 |
| GGGGCGCTGT ACGAGGTAAA GCCCGATGCC AGCATTCCTG ACGACGATAC | 200 |
| GGAGCTGCTG CGCGATTACG TAAAGAAGTT ATTGAAGCAT CCTCGTCAGT | 250 |
| AAAAAGTTAA TCTTTTCAAC AGCTGTCATA AAGTTGTCAC GGCCGAGACT | 300 |
| TATAGTCGCT TTGTTTTTAT TTTTTAATGT ATTTGTAACT AGAATTCGAG | 350 |
| CTCGGTACCC GGGGATCCTC TAGAGGTTGA GGTGATTTTA TGAAAAGAA | 400 |
| TATCGCATTT CTTCTTGCAT CTATGTTCGT TTTTTCTATT GCTACAAACG | 450 |
| CGTACGCTGA TATCCAGTTG ACCCAGTCCC CGAGCTCCCT GTCCGCCTCT | 500 |
| GTGGGCGATA GGGTCACCAT CACCTGCAGC GCAAGTCAGG ATATTAGCAA | 550 |
| CTATTTAAAC TGGTATCAAC AGAAACCAGG AAAAGCTCCG AAACTACTGA | 600 |
| TTTACTTCAC CTCCTCTCTC CACTCTGGAG TCCCTTCTCG CTTCTCTGGA | 650 |
| TCCGGTTCTG GGACGGATTA CACTCTGACC ATCAGCAGTC TGCAGCCAGA | 700 |
| AGACTTCGCA ACTTATTACT GTCAACAGTA TAGCACCGTG CCGTGGACGT | 750 |
| TTGGACAGGG TACCAAGGTG GAGATCAAAC GAACTGTGGC TGCACCATCT | 800 |
| GTCTTCATCT TCCCGCCATC TGATGAGCAG TTGAAATCTG GAACTGCTTC | 850 |
| TGTTGTGTGC CTGCTGAATA ACTTCTATCC CAGAGAGGCC AAAGTACAGT | 900 |
| GGAAGGTGGA TAACGCCCTC CAATCGGGTA ACTCCCAGGA GAGTGTCACA | 950 |
| GAGCAGGACA GCAAGGACAG CACCTACAGC CTCAGCAGCA CCCTGACGCT | 1000 |
| GAGCAAAGCA GACTACGAGA AACACAAAGT CTACGCCTGC GAAGTCACCC | 1050 |
| ATCAGGGCCT GAGCTCGCCC GTCACAAAGA GCTTCAACAG GGGAGAGTGT | 1100 |
| TAAGCTGATC CTCTACGCCG GACGCATCGT GGCCCTAGTA CGCAACTAGT | 1150 |
| CGTAAAAAGG GTATCTAGAG GTTGAGGTGA TTTTATGAAA AAGAATATCG | 1200 |
| CATTTCTTCT TGCATCTATG TTCGTTTTTT CTATTGCTAC AAACGCGTAC | 1250 |
| GCTGAGGTTC AGCTGGTGGA GTCTGGCGGT GGCCTGGTGC AGCCAGGGGG | 1300 |
| CTCACTCCGT TTGTCCTGTG CAGCTTCTGG CTATACCTTC ACCAACTATG | 1350 |

| | |
|---|---|
| GTATGAACTG GATCCGTCAG GCCCCGGGTA AGGGCCTGGA ATGGGTTGGA | 1400 |
| TGGATTAACA CCTATACCGG TGAACCGACC TATGCTGCGG ATTTCAAACG | 1450 |
| TCGTTTTACT ATATCTGCAG ACACCTCCAG CAACACAGTT TACCTGCAGA | 1500 |
| TGAACAGCCT GCGCGCTGAG GACACTGCCG TCTATTACTG TGCAAAGTAC | 1550 |
| CCGCACTATT ATGGGAGCAG CCACTGGTAT TTCGACGTCT GGGGTCAAGG | 1600 |
| AACCCTGGTC ACCGTCTCCT CGGCCTCCAC CAAGGGCCCA TCGGTCTTCC | 1650 |
| CCCTGGCACC CTCCTCCAAG AGCACCTCTG GGGGCACAGC GGCCCTGGGC | 1700 |
| TGCCTGGTCA AGGACTACTT CCCCGAACCG GTGACGGTGT CGTGGAACTC | 1750 |
| AGGCGCCCTG ACCAGCGGCG TGCACACCTT CCCGGCTGTC CTACAGTCCT | 1800 |
| CAGGACTCTA CTCCCTCAGC AGCGTGGTGA CCGTGCCCTC CAGCAGCTTG | 1850 |
| GGCACCCAGA CCTACATCTG CAACGTGAAT CACAAGCCCA GCAACACCAA | 1900 |
| GGTCGACAAG AAAGTTGAGC CCAAATCTTG TGACAAAACT CACCTCTAGA | 1950 |
| GTGGCGGTGG CTCTGGTTCC GGTGATTTTG ATTATGAAAA GATGGCAAAC | 2000 |
| GCTAATAAGG GGGCTATGAC CGAAAATGCC GATGAAAACG CGCTACAGTC | 2050 |
| TGACGCTAAA GGCAAACTTG ATTCTGTCGC TACTGATTAC GGTGCTGCTA | 2100 |
| TCGATGGTTT CATTGGTGAC GTTTCCGGCC TTGCTAATGG TAATGGTGCT | 2150 |
| ACTGGTGATT TTGCTGGCTC TAATTCCCAA ATGGCTCAAG TCGGTGACGG | 2200 |
| TGATAATTCA CCTTTAATGA ATAATTTCCG TCAATATTTA CCTTCCCTCC | 2250 |
| CTCAATCGGT TGAATGTCGC CCTTTTGTCT TTAGCGCTGG TAAACCATAT | 2300 |
| GAATTTTCTA TTGATTGTGA CAAAATAAAC TTATTCCGTG GTGTCTTTGC | 2350 |
| GTTTCTTTTA TATGTTGCCA CCTTTATGTA TGTATTTTCT ACGTTTGCTA | 2400 |
| ACATACTGCG TAATAAGGAG TCTTAATCAT GCCAGTTCTT TTGGCTAGCG | 2450 |
| CCGCCCTATA CCTTGTCTGC CTCCCCGCGT TGCGTCGCGG TGCATGGAGC | 2500 |
| CGGGCCACCT CGACCTGAAT GGAAGCCGGC GGCACCTCGC TAACGGATTC | 2550 |
| ACCACTCCAA GAATTGGAGC CAATCAATTC TTGCGGAGAA CTGTGAATGC | 2600 |
| GCAAACCAAC CCTTGGCAGA ACATATCCAT CGCGTCCGCC ATCTCCAGCA | 2650 |
| GCCGCACGCG GCGCATCTCG GCAGCGTTG GGTCCTGGCC ACGGGTGCGC | 2700 |
| ATGATCGTGC TCCTGTCGTT GAGGACCCGG CTAGGCTGGC GGGGTTGCCT | 2750 |
| TACTGGTTAG CAGAATGAAT CACCGATACG CGAGCGAACG TGAAGCGACT | 2800 |
| GCTGCTGCAA AACGTCTGCG ACCTGAGCAA CAACATGAAT GGTCTTCGGT | 2850 |
| TTCCGTGTTT CGTAAAGTCT GGAAACGCGG AAGTCAGCGC CCTGCACCAT | 2900 |
| TATGTTCCGG ATCTGCATCG CAGGATGCTG CTGGCTACCC TGTGGAACAC | 2950 |
| CTACATCTGT ATTAACGAAG CGCTGGCATT GACCCTGAGT GATTTTTCTC | 3000 |
| TGGTCCCGCC GCATCCATAC CGCCAGTTGT TTACCCTCAC AACGTTCCAG | 3050 |
| TAACCGGGCA TGTTCATCAT CAGTAACCCG TATCGTGAGC ATCCTCTCTC | 3100 |
| GTTTCATCGG TATCATTACC CCCATGAACA GAAATTCCCC CTTACACGGA | 3150 |
| GGCATCAAGT GACCAAACAG GAAAAAACCG CCCTTAACAT GGCCCGCTTT | 3200 |
| ATCAGAAGCC AGACATTAAC GCTTCTGGAG AAACTCAACG AGCTGGACGC | 3250 |
| GGATGAACAG GCAGACATCT GTGAATCGCT TCACGACCAC GCTGATGAGC | 3300 |
| TTTACCGCAG GATCCGGAAA TTGTAAACGT TAATATTTTG TTAAAATTCG | 3350 |

```
CGTTAAATTT TTGTTAAATC AGCTCATTTT TTAACCAATA GGCCGAAATC      3400

GGCAAAATCC CTTATAAATC AAAAGAATAG ACCGAGATAG GGTTGAGTGT      3450

TGTTCCAGTT TGGAACAAGA GTCCACTATT AAAGAACGTG GACTCCAACG      3500

TCAAAGGGCG AAAAACCGTC TATCAGGGCT ATGGCCCACT ACGTGAACCA      3550

TCACCCTAAT CAAGTTTTTT GGGGTCGAGG TGCCGTAAAG CACTAAATCG      3600

GAACCCTAAA GGGAGCCCCC GATTTAGAGC TTGACGGGGA AAGCCGGCGA      3650

ACGTGGCGAG AAAGGAAGGG AAGAAAGCGA AAGGAGCGGG CGCTAGGGCG      3700

CTGGCAAGTG TAGCGGTCAC GCTGCGCGTA ACCACCACAC CCGCCGCGCT      3750

TAATGCGCCG CTACAGGGCG CGTCCGGATC CTGCCTCGCG CGTTTCGGTG      3800

ATGACGGTGA AAACCTCTGA CACATGCAGC TCCCGGAGAC GGTCACAGCT      3850

TGTCTGTAAG CGGATGCCGG GAGCAGACAA GCCCGTCAGG GCGCGTCAGC      3900

GGGTGTTGGC GGGTGTCGGG GCGCAGCCAT GACCCAGTCA CGTAGCGATA      3950

GCGGAGTGTA TACTGGCTTA ACTATGCGGC ATCAGAGCAG ATTGTACTGA      4000

GAGTGCACCA TATGCGGTGT GAAATACCGC ACAGATGCGT AAGGAGAAAA      4050

TACCGCATCA GGCGCTCTTC CGCTTCCTCG CTCACTGACT CGCTGCGCTC      4100

GGTCGTTCGG CTGCGGCGAG CGGTATCAGC TCACTCAAAG GCGGTAATAC      4150

GGTTATCCAC AGAATCAGGG GATAACGCAG GAAAGAACAT GTGAGCAAAA      4200

GGCCAGCAAA AGGCCAGGAA CCGTAAAAAG GCCGCGTTGC TGGCGTTTTT      4250

CCATAGGCTC CGCCCCCCTG ACGAGCATCA CAAAAATCGA CGCTCAAGTC      4300

AGAGGTGGCG AAACCCGACA GGACTATAAA GATACCAGGC GTTTCCCCCT      4350

GGAAGCTCCC TCGTGCGCTC TCCTGTTCCG ACCCTGCCGC TTACCGGATA      4400

CCTGTCCGCC TTTCTCCCTT CGGGAAGCGT GGCGCTTTCT CATAGCTCAC      4450

GCTGTAGGTA TCTCAGTTCG GTGTAGGTCG TTCGCTCCAA GCTGGGCTGT      4500

GTGCACGAAC CCCCCGTTCA GCCCGACCGC TGCGCCTTAT CCGGTAACTA      4550

TCGTCTTGAG TCCAACCCGG TAAGACACGA CTTATCGCCA CTGGCAGCAG      4600

CCACTGGTAA CAGGATTAGC AGAGCGAGGT ATGTAGGCGG TGCTACAGAG      4650

TTCTTGAAGT GGTGGCCTAA CTACGGCTAC ACTAGAAGGA CAGTATTTGG      4700

TATCTGCGCT CTGCTGAAGC CAGTTACCTT CGGAAAAAGA GTTGGTAGCT      4750

CTTGATCCGG CAAACAAACC ACCGCTGGTA GCGGTGGTTT TTTTGTTTGC      4800

AAGCAGCAGA TTACGCGCAG AAAAAAAGGA TCTCAAGAAG ATCCTTTGAT      4850

CTTTTCTACG GGGTCTGACG CTCAGTGGAA CGAAAACTCA CGTTAAGGGA      4900

TTTTGGTCAT GAGATTATCA AAAAGGATCT TCACCTAGAT CCTTTTAAAT      4950

TAAAAATGAA GTTTTAAATC AATCTAAAGT ATATATGAGT AAACTTGGTC      5000

TGACAGTTAC CAATGCTTAA TCAGTGAGGC ACCTATCTCA GCGATCTGTC      5050

TATTTCGTTC ATCCATAGTT GCCTGACTCC CCGTCGTGTA GATAACTACG      5100

ATACGGGAGG GCTTACCATC TGGCCCCAGT GCTGCAATGA TACCGCGAGA      5150

CCCACGCTCA CCGGCTCCAG ATTTATCAGC AATAAACCAG CCAGCCGGAA      5200

GGGCCGAGCG CAGAAGTGGT CCTGCAACTT TATCCGCCTC CATCCAGTCT      5250

ATTAATTGTT GCCGGGAAGC TAGAGTAAGT AGTTCGCCAG TTAATAGTTT      5300
```

```
GCGCAACGTT GTTGCCATTG CTGCAGGCAT CGTGGTGTCA CGCTCGTCGT       5350

TTGGTATGGC TTCATTCAGC TCCGGTTCCC AACGATCAAG GCGAGTTACA       5400

TGATCCCCCA TGTTGTGCAA AAAAGCGGTT AGCTCCTTCG GTCCTCCGAT       5450

CGTTGTCAGA AGTAAGTTGG CCGCAGTGTT ATCACTCATG GTTATGGCAG       5500

CACTGCATAA TTCTCTTACT GTCATGCCAT CCGTAAGATG CTTTTCTGTG       5550

ACTGGTGAGT ACTCAACCAA GTCATTCTGA GAATAGTGTA TGCGGCGACC       5600

GAGTTGCTCT TGCCCGGCGT CAACACGGGA TAATACCGCG CCACATAGCA       5650

GAACTTTAAA AGTGCTCATC ATTGGAAAAC GTTCTTCGGG GCGAAAACTC       5700

TCAAGGATCT TACCGCTGTT GAGATCCAGT TCGATGTAAC CCACTCGTGC       5750

ACCCAACTGA TCTTCAGCAT CTTTTACTTT CACCAGCGTT TCTGGGTGAG       5800

CAAAAACAGG AAGGCAAAAT GCCGCAAAAA AGGGAATAAG GGCGACACGG       5850

AAATGTTGAA TACTCATACT CTTCCTTTTT CAATATTATT GAAGCATTTA       5900

TCAGGGTTAT TGTCTCATGA GCGGATACAT ATTTGAATGT ATTTAGAAAA       5950

ATAAACAAAT AGGGGTTCCG CGCACATTTC CCCGAAAAGT GCCACCTGAC       6000

GTCTAAGAAA CCATTATTAT CATGACATTA ACCTATAAAA ATAGGCGTAT       6050

CACGAGGCCC TTTCGTCTTC AA                                     6072
```

(2) INFORMATION FOR SEQ ID NO: 100:

(i) SEQUENCE CHARACTERISTICS:
        (A) LENGTH: 237 amino acids
        (B) TYPE: Amino Acid
        (D) TOPOLOGY: Linear (xi) SEQUENCE DESCRIPTION: SEQ ID NO: 100:

```
Met Lys Lys Asn Ile Ala Phe Leu Leu Ala Ser Met Phe Val Phe
-23         -20             -15                 -10

Ser Ile Ala Thr Asn Ala Tyr Ala Asp Ile Gln Leu Thr Gln Ser
            -5                1               5

Pro Ser Ser Leu Ser Ala Ser Val Gly Asp Arg Val Thr Ile Thr
        10                  15                  20

Cys Ser Ala Ser Gln Asp Ile Ser Asn Tyr Leu Asn Trp Tyr Gln
        25                  30                  35

Gln Lys Pro Gly Lys Ala Pro Lys Leu Leu Ile Tyr Phe Thr Ser
        40                  45                  50

Ser Leu His Ser Gly Val Pro Ser Arg Phe Ser Gly Ser Gly Ser
        55                  60                  65

Gly Thr Asp Tyr Thr Leu Thr Ile Ser Ser Leu Gln Pro Glu Asp
        70                  75                  80

Phe Ala Thr Tyr Tyr Cys Gln Gln Tyr Ser Thr Val Pro Trp Thr
        85                  90                  95

Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly
        145                 150                 155

Asn Ser Gln Glu Ser Val Thr Glu Gln Asp Ser Lys Asp Ser Thr
```

```
                160              165              170
Tyr Ser Leu Ser Ser Thr Leu Thr Leu Ser Lys Ala Asp Tyr Glu
            175              180              185

Lys His Lys Val Tyr Ala Cys Glu Val Thr His Gln Gly Leu Ser
            190              195              200

Ser Pro Val Thr Lys Ser Phe Asn Arg Gly Glu Cys
            205              210

(2) INFORMATION FOR SEQ ID NO: 101:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 101:

Asp Ile Gln Leu Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Leu Leu Ile Tyr Phe Thr Ser Ser Leu His Ser Gly Val Pro Ser
                50                  55                  60

Arg Phe Ser Gly Ser Gly Ser Gly Thr Asp Tyr Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
                110

(2) INFORMATION FOR SEQ ID NO: 102:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 102:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Met Asn Trp Ile Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Ile Ser Ala Asp Thr Ser
                65                  70                  75

Ser Asn Thr Val Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu
                110                 115
```

(2) INFORMATION FOR SEQ ID NO: 103:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 103:

```
Asp Ile Gln Leu Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Tyr Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
               110
```

(2) INFORMATION FOR SEQ ID NO: 104:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 104:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Met Asn Trp Ile Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Ala Asp Thr Ser
                65                  70                  75

Ser Asn Thr Val Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu
               110                 115
```

(2) INFORMATION FOR SEQ ID NO: 105:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 105:

Asp Ile Gln Leu Thr Gln Ser Pro Ser Ser Leu Ser Ala Ser Val

```
                    1               5                  10                 15
Gly Asp Arg Val Thr Ile Thr Cys Ser Ala Ser Gln Asp Ile Ser
                    20                     25                     30

Asn Tyr Leu Asn Trp Tyr Gln Gln Lys Pro Gly Lys Ala Pro Lys
                    35                     40                     45

Val Leu Ile Tyr Phe Thr Ser Ser Leu His Ser Gly Val Pro Ser
                    50                     55                     60

Arg Phe Ser Gly Ser Gly Ser Gly Thr Asp Phe Thr Leu Thr Ile
                    65                     70                     75

Ser Ser Leu Gln Pro Glu Asp Phe Ala Thr Tyr Tyr Cys Gln Gln
                    80                     85                     90

Tyr Ser Thr Val Pro Trp Thr Phe Gly Gln Gly Thr Lys Val Glu
                    95                     100                    105

Ile Lys Arg Thr Val
                    110

(2) INFORMATION FOR SEQ ID NO: 106:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 106:

Glu Val Gln Leu Val Glu Ser Gly Gly Gly Leu Val Gln Pro Gly
  1               5                  10                 15

Gly Ser Leu Arg Leu Ser Cys Ala Ala Ser Gly Tyr Thr Phe Thr
                    20                     25                     30

Asn Tyr Gly Met Asn Trp Val Arg Gln Ala Pro Gly Lys Gly Leu
                    35                     40                     45

Glu Trp Val Gly Trp Ile Asn Thr Tyr Thr Gly Glu Pro Thr Tyr
                    50                     55                     60

Ala Ala Asp Phe Lys Arg Arg Phe Thr Phe Ser Leu Asp Thr Ser
                    65                     70                     75

Lys Ser Thr Ala Tyr Leu Gln Met Asn Ser Leu Arg Ala Glu Asp
                    80                     85                     90

Thr Ala Val Tyr Tyr Cys Ala Lys Tyr Pro His Tyr Tyr Gly Ser
                    95                     100                    105

Ser His Trp Tyr Phe Asp Val Trp Gly Gln Gly Thr Leu
                    110                    115

(2) INFORMATION FOR SEQ ID NO: 107:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 107:

Asp Ile Gln Leu Thr Gln Ser Pro Ser Ser Leu Ser Ala Ser Val
  1               5                  10                 15

Gly Asp Arg Val Thr Ile Thr Cys Arg Ala Asn Glu Gln Leu Ser
                    20                     25                     30

Asn Tyr Leu Asn Trp Tyr Gln Gln Lys Pro Gly Lys Ala Pro Lys
                    35                     40                     45

Val Leu Ile Tyr Phe Thr Ser Ser Leu His Ser Gly Val Pro Ser
                    50                     55                     60
```

```
Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
               110

(2) INFORMATION FOR SEQ ID NO: 108:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 108:

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Asn Tyr Gly Ile Asn Trp Val Arg Gln Ala Pro Gly Lys Gly Leu
                 35                  40                  45

Glu Trp Val Gly Trp Ile Asn Thr Tyr Thr Gly Glu Pro Thr Tyr
                 50                  55                  60

Ala Ala Asp Phe Lys Arg Arg Phe Thr Phe Ser Leu Asp Thr Ser
                 65                  70                  75

Lys Ser Thr Ala Tyr Leu Gln Met Asn Ser Leu Arg Ala Glu Asp
                 80                  85                  90

Thr Ala Val Tyr Tyr Cys Ala Lys Tyr Pro His Tyr Tyr Gly Ser
                 95                 100                 105

Ser His Trp Tyr Phe Asp Val Trp Gly Gln Gly Thr Leu
                110                 115

(2) INFORMATION FOR SEQ ID NO: 109:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 109:

Asp Ile Gln Leu Thr Gln Ser Pro Ser Ser Leu Ser Ala Ser Val
  1               5                  10                  15

Gly Asp Arg Val Thr Ile Thr Cys Arg Ala Asn Glu Gln Leu Ser
                 20                  25                  30

Asn Tyr Leu Asn Trp Tyr Gln Gln Lys Pro Gly Lys Ala Pro Lys
                 35                  40                  45

Val Leu Ile Tyr Phe Thr Ser Ser Leu His Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Tyr Ser Thr Val Pro Trp Thr Phe Gly Gln Gly Thr Lys Val Glu
                 95                 100                 105

Ile Lys Arg Thr Val
                110
```

(2) INFORMATION FOR SEQ ID NO: 110:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 110:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Asp Phe Thr
                20                  25                  30

His Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu
               110                 115

(2) INFORMATION FOR SEQ ID NO: 111:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 111:

Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
               110

(2) INFORMATION FOR SEQ ID NO: 112:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 112:

-continued

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Ile Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro Tyr Tyr Tyr Gly Thr
                95                 100                 105

Ser His Trp Tyr Phe Asp Val Trp Gly Gln Gly Thr Leu
                110                 115
```

(2) INFORMATION FOR SEQ ID NO: 113:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 113:

```
Asp Ile Gln Leu Thr Gln Ser Pro Ser Ser Leu Ser Ala Ser Val
 1               5                  10                  15

Gly Asp Arg Val Thr Ile Thr Cys Arg Ala Asn Glu Gln Leu Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg Thr Val
                110
```

(2) INFORMATION FOR SEQ ID NO: 114:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 114:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Asp Phe Thr
                20                  25                  30

His Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60
```

Ala Ala Asp Phe Lys Arg Arg Phe Thr Phe Ser Leu Asp Thr Ser
            65                  70                  75

Lys Ser Thr Ala Tyr Leu Gln Met Asn Ser Leu Arg Ala Glu Asp
        80                  85                  90

Thr Ala Val Tyr Tyr Cys Ala Lys Tyr Pro Tyr Tyr Tyr Gly Thr
            95                  100                 105

Ser His Trp Tyr Phe Asp Val Trp Gly Gln Gly Thr Leu
            110                 115

(2) INFORMATION FOR SEQ ID NO: 115:

(i) SEQUENCE CHARACTERISTICS:
        (A) LENGTH: 110 amino acids
        (B) TYPE: Amino Acid
        (D) TOPOLOGY: Linear (xi) SEQUENCE DESCRIPTION: SEQ ID NO: 115:

Asp Ile Gln Leu Thr Gln Ser Pro Ser Ser Leu Ser Ala Ser Val
 1               5                  10                  15

Gly Asp Arg Val Thr Ile Thr Cys Ser Ala Ser Gln Asp Ile Ser
            20                  25                  30

Asn Tyr Leu Asn Trp Tyr Gln Gln Lys Pro Gly Lys Ala Pro Lys
            35                  40                  45

Val Leu Ile Tyr Phe Thr Ser Ser Leu His Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Ser Thr Val Pro Trp Thr Phe Gly Gln Gly Thr Lys Val Glu
            95                  100                 105

Ile Lys Arg Thr Val
            110

(2) INFORMATION FOR SEQ ID NO: 116:

(i) SEQUENCE CHARACTERISTICS:
        (A) LENGTH: 118 amino acids
        (B) TYPE: Amino Acid
        (D) TOPOLOGY: Linear (xi) SEQUENCE DESCRIPTION: SEQ ID NO: 116:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Asp Phe Thr
            20                  25                  30

His Tyr Gly Met Asn Trp Val Arg Gln Ala Pro Gly Lys Gly Leu
            35                  40                  45

Glu Trp Val Gly Trp Ile Asn Thr Tyr Thr Gly Glu Pro Thr Tyr
            50                  55                  60

Ala Ala Asp Phe Lys Arg Arg Phe Thr Phe Ser Leu Asp Thr Ser
            65                  70                  75

Lys Ser Thr Ala Tyr Leu Gln Met Asn Ser Leu Arg Ala Glu Asp
        80                  85                  90

Thr Ala Val Tyr Tyr Cys Ala Lys Tyr Pro Tyr Tyr Tyr Gly Thr
            95                  100                 105

Ser His Trp Tyr Phe Asp Val Trp Gly Gln Gly Thr Leu 110                 115

(2) INFORMATION FOR SEQ ID NO: 117:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 117:

Gly Tyr Xaa Xaa Xaa Xaa Tyr Gly Xaa Asn
 1               5                  10

(2) INFORMATION FOR SEQ ID NO: 118:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 118:

Trp Ile Asn Thr Xaa Thr Gly Glu Pro Thr Tyr Ala Ala Asp Phe
 1               5                  10                  15

Lys Arg (2) INFORMATION FOR SEQ ID NO: 119:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 119:

Tyr Pro Xaa Tyr Xaa Xaa Xaa Xaa His Trp Tyr Phe Asp Val
 1               5                  10

(2) INFORMATION FOR SEQ ID NO: 120:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 120:

Xaa Ser Xaa Asp Xaa Xaa Xaa Xaa Thr Xaa
 1               5                  10

(2) INFORMATION FOR SEQ ID NO: 121:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 121:

Xaa Ala Xaa Xaa Xaa Xaa Ser Asn Tyr Leu Asn
 1               5                  10

(2) INFORMATION FOR SEQ ID NO: 122:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 122:

```
Phe Thr Ser Ser Leu His Ser
 1               5
```

(2) INFORMATION FOR SEQ ID NO: 123:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO: 123:

```
Gln Gln Tyr Ser Xaa Xaa Pro Trp Thr
 1               5
```

(2) INFORMATION FOR SEQ ID NO: 124:

(i) SEQUENCE CHARACTERISTICS:
        (A) LENGTH: 108 amino acids
        (B) TYPE: Amino Acid
        (D) TOPOLOGY: Linear (xi) SEQUENCE DESCRIPTION: SEQ ID NO: 124:

```
Asp Ile Gln Xaa Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                  100                 105

Ile Lys Arg
```

(2) INFORMATION FOR SEQ ID NO: 125:

(i) SEQUENCE CHARACTERISTICS:
        (A) LENGTH: 123 amino acids
        (B) TYPE: Amino Acid
        (D) TOPOLOGY: Linear (xi) SEQUENCE DESCRIPTION: SEQ ID NO: 125:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Xaa Phe Thr
                20                  25                  30

Xaa Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro Xaa Tyr Tyr Gly Xaa
                95                  100                 105
```

```
Ser His Trp Tyr Phe Asp Val Trp Gly Gln Gly Thr Leu Val Thr
            110                 115                 120

Val Ser Ser
```

(2) INFORMATION FOR SEQ ID NO: 126:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 126:

```
Gly Tyr Asp Phe Thr His Tyr Gly Met Asn
 1               5                  10
```

(2) INFORMATION FOR SEQ ID NO: 127:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 127:

```
Tyr Pro Tyr Tyr Tyr Gly Thr Ser His Trp Tyr Phe Asp Val
 1               5                  10
```

(2) INFORMATION FOR SEQ ID NO: 128:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 128:

```
Gly Tyr Xaa Phe Thr Xaa Tyr Gly Met Asn
 1               5                  10
```

(2) INFORMATION FOR SEQ ID NO: 129:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 129:

```
Tyr Pro Xaa Tyr Tyr Gly Xaa Ser His Trp Tyr Phe Asp Val
 1               5                  10
```

(2) INFORMATION FOR SEQ ID NO: 130:

(i) SEQUENCE CHARACTERISTICS:
        (A) LENGTH: 254 amino acids
        (B) TYPE: Amino Acid
        (D) TOPOLOGY: Linear (xi) SEQUENCE DESCRIPTION: SEQ ID NO: 130:

```
Met Lys Lys Asn Ile Ala Phe Leu Leu Ala Ser Met Phe Val Phe
-23             -20                 -15                 -10

Ser Ile Ala Thr Asn Ala Tyr Ala Glu Val Gln Leu Val Glu Ser
                -5                   1                   5

Gly Gly Gly Leu Val Gln Pro Gly Gly Ser Leu Arg Leu Ser Cys
                10                  15                  20

Ala Ala Ser Gly Tyr Thr Phe Thr Asn Tyr Gly Met Asn Trp Ile
                25                  30                  35
```

-continued

```
Arg Gln Ala Pro Gly Lys Gly Leu Glu Trp Val Gly Trp Ile Asn
             40                  45                  50

Thr Tyr Thr Gly Glu Pro Thr Tyr Ala Ala Asp Phe Lys Arg Arg
             55                  60                  65

Phe Thr Ile Ser Ala Asp Thr Ser Asn Thr Val Tyr Leu Gln
             70                  75                  80

Met Asn Ser Leu Arg Ala Glu Asp Thr Ala Val Tyr Tyr Cys Ala
             85                  90                  95

Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro
            145                 150                 155

Glu Pro Val Thr Val Ser Trp Asn Ser Gly Ala Leu Thr Ser Gly
            160                 165                 170

Val His Thr Phe Pro Ala Val Leu Gln Ser Ser Gly Leu Tyr Ser
            175                 180                 185

Leu Ser Ser Val Val Thr Val Pro Ser Ser Ser Leu Gly Thr Gln
            190                 195                 200

Thr Tyr Ile Cys Asn Val Asn His Lys Pro Ser Asn Thr Lys Val
            205                 210                 215

Asp Lys Lys Val Glu Pro Lys Ser Cys Asp Lys Thr His Leu
            220                 225                 230

(2) INFORMATION FOR SEQ ID NO: 131:

(i) SEQUENCE CHARACTERISTICS:
        (A) LENGTH: 158 amino acids
        (B) TYPE: Amino Acid
        (D) TOPOLOGY: Linear (xi) SEQUENCE DESCRIPTION: SEQ ID NO: 131:

Ser Gly Gly Gly Ser Gly Ser Gly Asp Phe Asp Tyr Glu Lys Met
 1                   5                  10                  15

Ala Asn Ala Asn Lys Gly Ala Met Thr Glu Asn Ala Asp Glu Asn
             20                  25                  30

Ala Leu Gln Ser Asp Ala Lys Gly Lys Leu Asp Ser Val Ala Thr
             35                  40                  45

Asp Tyr Gly Ala Ala Ile Asp Gly Phe Ile Gly Asp Val Ser Gly
             50                  55                  60

Leu Ala Asn Gly Asn Gly Ala Thr Gly Asp Phe Ala Gly Ser Asn
             65                  70                  75

Ser Gln Met Ala Gln Val Gly Asp Gly Asp Asn Ser Pro Leu Met
             80                  85                  90

Asn Asn Phe Arg Gln Tyr Leu Pro Ser Leu Pro Gln Ser Val Glu
             95                 100                 105

Cys Arg Pro Phe Val Phe Ser Ala Gly Lys Pro Tyr Glu Phe Ser
            110                 115                 120

Ile Asp Cys Asp Lys Ile Asn Leu Phe Arg Gly Val Phe Ala Phe
            125                 130                 135
```

```
-continued

Leu Leu Tyr Val Ala Thr Phe Met Tyr Val Phe Ser Thr Phe Ala
            140                 145                 150

Asn Ile Leu Arg Asn Lys Glu Ser
                155
```

ANTI-VEGF ANTIBODIES

CROSS REFERENCES

This application is a continuation of U.S. application Ser. No. 10/974,591, filed Oct. 26, 2004, allowed Jul. 3, 2007, which is a continuation of U.S. application Ser. No. 09/723,752, filed Nov. 27, 2000, now U.S. Pat. No. 7,060,269, which is a divisional of U.S. application Ser. No. 08/908,469, filed Aug. 6, 1997, now U.S. Pat. No. 6,884,879, which claims the benefit of U.S. Provisional Application No. 60/126,446, filed Apr. 7, 1997, now abandoned the contents of which applications are incorporated herein by reference.

BACKGROUND OF THE INVENTION

1. Field of the Invention

This invention relates generally to anti-VEGF antibodies and, in particular, to humanized anti-VEGF antibodies and variant anti-VEGF antibodies.

2. Description of Related Art

It is now well established that angiogenesis is implicated in the pathogenesis of a variety of disorders. These include solid tumors, intraocular neovascular syndromes such as proliferative retinopathies or age-related macular degeneration (AMD), rheumatoid arthritis, and psoriasis (Folkman et al. *J. Biol. Chem.* 267:10931-10934 (1992); Klagsbrun et al. *Annu. Rev. Physiol.* 53:217-239 (1991); and Garner A, *Vascular diseases. In: Pathobiology of ocular disease. A dynamic approach.* Garner A, Klintworth G K, Eds. 2nd Edition Marcel Dekker, NY, pp 1625-1710 (1994)). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner et al. *N Engl J Med* 324:1-6 (1991); Horak et al. *Lancet* 340:1120-1124 (1992); and Macchiarini et al. *Lancet* 340:145-146 (1992)).

The search for positive regulators of angiogenesis has yielded many candidates, including aFGF, bFGF, TGF-α, TGF-β, HGF, TNF-α, angiogenin, IL-8, etc. (Folkman et al. and Klagsbrun et al). The negative regulators so far identified include thrombospondin (Good et al. *Proc. Natl. Acad. Sci. USA.* 87:6624-6628 (1990)), the 16-kilodalton N-terminal fragment of prolactin (Clapp et al. *Endocrinology*, 133: 1292-1299 (1993)), angiostatin (O'Reilly et al. *Cell,* 79:315-328 (1994)) and endostatin (O'Reilly et al. *Cell,* 88:277-285 (1996)).

Work done over the last several years has established the key role of vascular endothelial growth factor (VEGF) in the regulation of normal and abnormal angiogenesis (Ferrara et al. *Endocr. Rev.* 18:4-25 (1997)). The finding that the loss of even a single VEGF allele results in embryonic lethality points to an irreplaceable role played by this factor in the development and differentiation of the vascular system (Ferrara et al.). Furthermore, VEGF has been shown to be a key mediator of neovascularization associated with tumors and intraocular disorders (Ferrara et al.). The VEGF mRNA is overexpressed by the majority of human tumors examined (Berkman et al. *J Clin Invest* 91:153-159 (1993); Brown et al. *Human Pathol.* 26:86-91 (1995); Brown et al. *Cancer Res.* 53:4727-4735 (1993); Mattern et al. *Brit. J. Cancer.* 73:931-934 (1996); and Dvorak et al. *Am J. Pathol.* 146: 1029-1039 (1995)). Also, the concentration of VEGF in eye fluids are highly correlated to the presence of active proliferation of blood vessels in patients with diabetic and other ischemia-related retinopathies (Aiello et al. *N. Engl. J. Med.* 331:1480-1487 (1994)). Furthermore, recent studies have demonstrated the localization of VEGF in choroidal neovascular membranes in patients affected by AMD (Lopez et al. *Invest. Ophtalmo. Vis. Sci.* 37:855-868 (1996)). Anti-VEGF neutralizing antibodies suppress the growth of a variety of human tumor cell lines in nude mice (Kim et al. *Nature* 362:841-844 (1993); Warren et al. *J. Clin. Invest.* 95:1789-1797 (1995); Borgström et al. *Cancer Res.* 56:4032-4039 (1996); and Melnyk et al. *Cancer Res.* 56:921-924 (1996)) and also inhibit intraocular angiogenesis in models of ischemic retinal disorders (Adamis et al. *Arch. Ophthalmol.* 114:66-71 (1996)). Therefore, anti-VEGF monoclonal antibodies or other inhibitors of VEGF action are promising candidates for the treatment of solid tumors and various intraocular neovascular disorders.

SUMMARY OF THE INVENTION

This application describes humanized anti-VEGF antibodies and anti-VEGF antibody variants with desirable properties from a therapeutic perspective, including strong binding affinity for VEGF; the ability to inhibit VEGF-induced proliferation of endothelial cells in vitro; and the ability to inhibit VEGF-induced angiogenesis in vivo.

The preferred humanized anti-VEGF antibody or variant anti-VEGF antibody herein binds human VEGF with a $K_d$ value of no more than about $1\times10^{-8}$ M and preferably no more than about $5\times10^{-9}$ M. In addition, the humanized or variant anti-VEGF antibody may have an ED50 value of no more than about 5 nM for inhibiting VEGF-induced proliferation of endothelial cells in vitro. The humanized or variant anti-VEGF antibodies of particular interest herein are those which inhibit at least about 50% of tumor growth in an A673 in vivo tumor model, at an antibody dose of 5 mg/kg.

In one embodiment, the anti-VEGF antibody has a heavy and light chain variable domain, wherein the heavy chain variable domain comprises hypervariable regions with the following amino acid sequences: CDRH1 (GYX$_1$FTX$_2$YGMN, wherein X$_1$ is T or D and X$_2$ is N or H; SEQ ID NO:128), CDRH2 (WINTYTGEPTYAADFKR; SEQ ID NO:2) and CDRH3 (YPX$_1$YYGX$_2$SHWYFDV, wherein X$_1$ is Y or H and X$_2$ is S or T; SEQ ID NO:129). For example, the heavy chain variable domain may comprise the amino acid sequences of CDRH1 (GYTFTNYGMN; SEQ ID NO:1), CDRH2 (WINTYTGEPTYAADFKR; SEQ ID NO:2) and CDRH3 (YPHYYGSSHWYFDV; SEQ ID NO:3). Preferably, the three heavy chain hypervariable regions are provided in a human framework region, e.g., as a contiguous sequence represented by the following formula: FR1-CDRH1-FR2-CDRH2-FR3-CDRH3-FR4.

The invention further provides an anti-VEGF antibody heavy chain variable domain comprising the amino acid sequence:

EVQLVESGGGLVQPGGSLRLSCAASGYX$_1$FTX$_2$YGM NWVRQAPGKGLEWVGWINTYTGEPT YAADFKRRFT FSLDTSKSTAYLQMNSLRAEDTAVYYCAKYPX$_3$YYG X$_4$SHWYFDVWGQGTLVTVSS (SEQ ID NO:125), wherein X$_1$ is T or D; X$_2$ is N or H; X$_3$ is Y or H and X$_4$ is S or T. One particularly useful heavy chain variable domain sequence is that of the F(ab)-12 humanized antibody of Example 1 and comprises the heavy chain variable domain sequence of SEQ ID NO:7. Such preferred heavy chain variable domain sequences may be combined with the following preferred light chain variable domain sequences or with other light chain variable domain sequences, provided that the antibody so produced binds human VEGF.

The invention also provides preferred light chain variable domain sequences which may be combined with the above-identified heavy chain variable domain sequences or with other heavy chain variable domain sequences, provided that the antibody so produced retains the ability to bind to human VEGF. For example, the light chain variable domain may comprise hypervariable regions with the following amino acid sequences: CDRL1 (SASQDISNYLN; SEQ ID NO:4), CDRL2 (FTSSLHS; SEQ ID NO:5) and CDRL3 (QQYSTVPWT; SEQ ID NO:6). Preferably, the three light chain hypervariable regions are provided in a human framework region, e.g., as a contiguous sequence represented by the following formula: FR1-CDRL1-FR2-CDRL2-FR3-CDRL3-FR4.

In one embodiment, the invention provides a humanized anti-VEGF antibody light chain variable domain comprising the amino acid sequence:

DIQX$_1$TQSPSSLSASVGDRVTITCSASQDISNYLNWYQ QKPGKAPKVLIYFTSSLHSGVPSRFSGSGSGTDFTLTI SSLQPEDFATYYCQQYSTVPWTFGQGTKVEIKR (SEQ ID NO:124), wherein X$_1$ is M or L. One particularly useful light chain variable domain sequence is that of the F(ab)-12 humanized antibody of Example 1 and comprises the light chain variable domain sequence of SEQ ID NO:8.

The invention also provides a variant of a parent anti-VEGF antibody (which parent antibody is preferably a humanized or human anti-VEGF antibody), wherein the variant binds human VEGF and comprises an amino acid substitution in a hypervariable region of the heavy or light chain variable domain of the parent anti-VEGF antibody. The variant preferably has one or more substitution(s) in one or more hypervariable region(s) of the anti-VEGF antibody. Preferably, the substitution(s) are in the heavy chain variable domain of the parent antibody. For example, the amino acid substitution (s) may be in the CDRH1 and/or CDRH3 of the heavy chain variable domain. Preferably, there are substitutions in both these hypervariable regions. Such "affinity matured" variants are demonstrated herein to bind human VEGF more strongly than the parent anti-VEGF antibody from which they are generated, i.e., they have a K$_d$ value which is significantly less than that of the parent anti-VEGF antibody. Preferably, the variant has an ED50 value for inhibiting VEGF-induced proliferation of endothelial cells in vitro which is at least about 10 fold lower, preferably at least about 20 fold lower, and most preferably at least about 50 fold lower, than that of the parent anti-VEGF antibody. One particularly preferred variant is the Y0317 variant of Example 3, which has a CDRH1 comprising the amino acid sequence:GYDFTHYGMN (SEQ ID NO:126) and a CDRH3 comprising the amino acid sequence:YPYYYGT-SHWYFDV (SEQ ID NO:127). These hypervariable regions and CDRH2 are generally provided in a human framework region, e.g., resulting in a heavy chain variable domain comprising the amino acid sequence of SEQ ID NO:116. Such heavy chain variable domain sequences are optionally combined with a light chain variable domain comprising the amino acid sequence of SEQ ID NO:124, and preferably the light chain variable domain amino acid sequence of SEQ ID NO:115.

Various forms of the antibody are contemplated herein. For example, the anti-VEGF antibody may be a full length antibody (e.g. having an intact human Fc region) or an antibody fragment (e.g. a Fab, Fab' or F(ab')$_2$). Furthermore, the antibody may be labeled with a detectable label, immobilized on a solid phase and/or conjugated with a heterologous compound (such as a cytotoxic agent).

Diagnostic and therapeutic uses for the antibody are contemplated. In one diagnostic application, the invention provides a method for determining the presence of VEGF protein comprising exposing a sample suspected of containing the VEGF protein to the anti-VEGF antibody and determining binding of the antibody to the sample. For this use, the invention provides a kit comprising the antibody and instructions for using the antibody to detect the VEGF protein.

The invention further provides: isolated nucleic acid encoding the antibody; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising the anti-VEGF antibody and a pharmaceutically acceptable carrier or diluent. The composition for therapeutic use is sterile and may be lyophilized. The invention further provides a method for treating a mammal suffering from a tumor or retinal disorder, comprising administering a therapeutically effective amount of the anti-VEGF antibody to the mammal.

BRIEF DESCRIPTION OF THE DRAWINGS

FIGS. 1A and 1B depict the amino acid sequences of variable heavy domain (SEQ ID NO:9) and light domain (SEQ ID NO:10) of muMAbVEGF A.4.6.1, variable heavy domain (SEQ ID NO:7) and light domain (SEQ ID NO:8) of humanized F(ab) (F(ab)-12) and human consensus frameworks (hum III for heavy subgroup III (SEQ ID NO:11); humκ1 for light κ subgroup I (SEQ ID NO:12)). FIG. 1A aligns variable heavy domain sequences and FIG. 1B aligns variable light domain sequences. Asterisks indicate differences between humanized F(ab)-12 and the murine MAb or between F(ab)-12 and the human framework. Complementarity Determining Regions (CDRs) are underlined.

FIG. 2 is a ribbon diagram of the model of humanized F(ab)-12 VL and VH domains. VL domain is shown in brown with CDRs in tan. The sidechain of residue L46 is shown in yellow. VH domain is shown in purple with CDRs in pink. Sidechains of VH residues changed from human to murine are shown in yellow.

FIG. 3 depicts inhibition of VEGF-induced mitogenesis by humanized anti-VEGF F(ab)-12 from Example 1. Bovine adrenal cortex-derived capillary endothelial cells were seeded at the density of 6×10$^3$ cells/well in six well plates, as described in Example 1. Either muMAb VEGF A.4.6.1 or rhuMAb VEGF (IgG1; F(ab)-12) was added at the indicated concentrations. After 2-3 hours, rhVEGF165 was added at the final concentration of 3 ng/ml. After five or six days, cells were trypsinized and counted. Values shown are means of duplicate determinations. The variation from the mean did not exceed 10%.

FIG. 4 shows inhibition of tumor growth in vivo by humanized anti-VEGF F(ab)-12 from Example 1. A673 rhabdomyosarcoma cells were injected in BALB/c nude mice at the density of 2×10$^6$ per mouse. Starting 24 hours after tumor cell inoculation, animals were injected with a control MAb, muMAb VEGF A4.6.1 or rhuVEGF MAb (IgG1; F(ab)-12) twice weekly, intra peritoneally. The dose of the control Mab was 5 mg/kg; the anti-VEGF MAbs were given at 0.5 or 5 mg/kg, as indicated (n=10). Four weeks after tumor cell injection, animals were euthanized and tumors were removed and weighed. *: significant difference when compared to the control group by ANOVA (p<0.05).

FIGS. 5A and 5B show the acid sequences of the light and heavy variable domains respectively of murine antibody A4.6.1 (SEQ ID NO:10 for the VL and SEQ ID NO:9 for the VH) and humanized A4.6.1 variants hu2.0 (SEQ ID NO:13 for the VL and SEQ ID NO:14 for the VH) and hu2.10 (SEQ ID NO:15 for the VL and SEQ ID NO:16 for the VH) from Example 2. Sequence numbering is according to Kabat et al., *Sequences of Proteins of Immunological Interest,* 5th Ed. Public Health Service, National Institutes of Health, Bethesda, Md. (1991) and mismatches are indicated by asterisks (murine A4.6.1 vs hu2.0) or bullets (hu2.0 vs hu2.10). Variant hu2.0 contains only the CDR sequences (bold) from the murine antibody grafted onto a human light chain κ subgroup I consensus framework (SEQ ID NO:12) and heavy chain subgroup III consensus framework (SEQ ID NO:11). hu2.10 was the consensus humanized clone obtained from phage sorting experiments described herein.

FIG. 6 depicts framework residues targeted for randomization in Example 2.

FIG. 7 depicts the phagemid construct for surface display of Fab-pIII fusions on phage. The phagemid encodes a humanized version of the Fab fragment for antibody A4.6.1 fused to a portion of the M13 gene III coat protein. The fusion protein consists of the Fab joined at the carboxyl terminus of the heavy chain to a single glutamine residue (from suppression of an amber codon in supE *E. coli*), then the C-terminal region of the gene III protein (residues 249-406). Transformation into F+ *E. coli*, followed by superinfection with M13K07 helper phage, produces phagemid particles in which a small proportion of these display a single copy of the fusion protein.

FIGS. 8A-F depict the double stranded nucleotide sequence (SEQ ID NO:99) for phage-display antibody vector phMB4-19-1.6 in Example 3 and the amino acid sequence encoded thereby (SEQ ID NO:100).

FIGS. 9A and 9B depict an alignment of the amino acid sequences for the light and heavy variable domains respectively of affinity matured anti-VEGF variants in Example 3, compared to F(ab)-12 of Example 1 (SEQ ID NO's 8 and 7 for light and heavy variable domains, respectively). CDRs are underlined and designated by L, light, or H, heavy chain, and numbers 1-3. Residues are numbered sequentially in the VL and VH domains, as opposed to the Kabat numbering scheme. The template molecule, MB1.6 (SEQ ID NO's 101 and 102 for light and heavy variable domains, respectively) is shown, along with variants: H2305.6 (SEQ ID NO's 103 and 104 for light and heavy variable domains, respectively), Y0101 (SEQ ID NO's 105 and 106 for light and heavy variable domains, respectively), and Y0192 (SEQ ID NO's 107 and 108 for light and heavy variable domains, respectively). Differences from F(ab)-12 are shown in shaded boxes.

FIGS. 10A and 10B depict an alignment of the amino acid sequences for the light and heavy variable domains respectively of affinity matured anti-VEGF variants from Example 3 compared to F(ab)-12 of Example 1 (SEQ ID NO's 8 and 7 for light and heavy variable domains, respectively). CDRs are underlined and designated by L, light, or H, heavy chain, and numbers 1-3. The variants are designated Y0243-1 (SEQ ID NO's 109 and 110 for light and heavy variable domains, respectively), Y0238-3 (SEQ ID NO's 111 and 112 for light and heavy variable domains, respectively), Y0313-1 (SEQ ID NO's 113 and 114 for light and heavy variable domains, respectively), and Y0317 (SEQ ID NO's 115 and 116 for light and heavy variable domains, respectively). Differences from F(ab)-12 are shown in shaded boxes.

FIG. 11 depicts the results of the HuVEC activity assay in Example 3 for variants Y0238-3, Y0192 and Y0313-1 as well as full length F(ab)-12 from Example 1.

FIG. 12 depicts inhibition of VEGF-induced mitogenesis by full length F(ab)-12 from Example 1 (rhuMAb VEGF), a Fab fragment of F(ab)-12 from Example 1 (rhuFab VEGF), and a Fab fragment of affinity matured variant Y0317 from Example 3 (rhuFab VEGF (affinity matured)).

DETAILED DESCRIPTION OF THE PREFERRED EMBODIMENTS

I. Definitions

The term "human VEGF" as used herein refers to the 165-amino acid human vascular endothelial cell growth factor, and related 121-, 189-, and 206-amino acid vascular endothelial cell growth factors, as described by Leung et al., *Science* 246:1306 (1989), and Houck et al., *Mol. Endocrin.* 5:1806 (1991) together with the naturally occurring allelic and processed forms of those growth factors.

The present invention provides anti-VEGF antagonistic antibodies which are capable of inhibiting one or more of the biological activities of VEGF, for example, its mitogenic or angiogenic activity. Antagonists of VEGF act by interfering with the binding of VEGF to a cellular receptor, by incapacitating or killing cells which have been activated by VEGF, or by interfering with vascular endothelial cell activation after VEGF binding to a cellular receptor. All such points of intervention by a VEGF antagonist shall be considered equivalent for purposes of this invention.

The term "VEGF receptor" or "VEGFr" as used herein refers to a cellular receptor for VEGF, ordinarily a cell-surface receptor found on vascular endothelial cells, as well as variants thereof which retain the ability to bind hVEGF. One example of a VEGF receptor is the fms-like tyrosine kinase (flt), a transmembrane receptor in the tyrosine kinase family. DeVries et al., *Science* 255:989 (1992); Shibuya et al., *Oncogene* 5:519 (1990). The flt receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the flk-1 receptor (also referred to as KDR). Matthews et al., *Proc. Nat. Acad. Sci.* 88:9026 (1991); Terman et al., *Oncogene* 6:1677 (1991); Terman et al., *Biochem. Biophys. Res. Commun.* 187:1579 (1992). Binding of VEGF to the flt receptor results in the formation of at least two high molecular weight complexes, having apparent molecular weight of 205,000 and 300,000 Daltons. The 300,000 Dalton complex is believed to be a dimer comprising two receptor molecules bound to a single molecule of VEGF.

The term "epitope A4.6.1" when used herein, unless indicated otherwise, refers to the region of human VEGF to which the A4.6.1 antibody disclosed in Kim et al., *Growth Factors* 7:53 (1992) and Kim et al. *Nature* 362:841 (1993), binds.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments" comprise a portion of a full length antibody, generally the antigen binding or variable domain thereof. Examples of antibody fragments include Fab, Fab', $F(ab')_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Struct. Biol. 2:593-596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

The expression "linear antibodies" when used throughout this application refers to the antibodies described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

A "variant" anti-VEGF antibody, refers herein to a molecule which differs in amino acid sequence from a "parent" anti-VEGF antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences (e.g. as in SEQ ID NO:7 or 8), more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human VEGF and preferably has properties which are superior to those of the parent antibody. For example, the variant may have a stronger binding affinity, enhanced ability to inhibit VEGF-induced proliferation of endothelial cells and/or increased ability to inhibit VEGF-induced angiogenesis in vivo. To analyze such properties, one should compare a Fab form of the variant to a Fab form of the parent antibody or a full length form of the variant to a full length form of the parent antibody, for example, since it has been found that the format of the anti-VEGF antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The "parent" antibody herein is one which is encoded by an amino acid sequence used for the preparation of the variant. Preferably, the parent antibody has a human framework region and, if present, has human antibody constant region(s). For example, the parent antibody may be a humanized or human antibody.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to the anti-VEGF antibody fused to an "epitope tag". The epitope tag polypeptide has enough residues to provide an epitope against which an antibody thereagainst can be made, yet is short enough such that it does not interfere with activity of the VEGF antibody. The epitope tag preferably is sufficiently unique so that the antibody thereagainst does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al. *Mol. Cell. Biol.* 8:2159-2165 (1988)); the c-myc tag and the 8F9, 3C7, 6E10, G4, B7 and 9E10 antibodies thereto (Evan et al., *Mol. Cell. Biol.* 5(12):3610-3616 (1985)); and the Herpes Simplex virus glycoprotein D (gD) tag and its antibody (Paborsky et al., *Protein Engineering* 3(6):547-553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose) polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-VEGF antibodies disclosed herein and, optionally, a chemotherapeutic agent) to a mammal. The components of the liposome are commonly arranged in a bilayer formation, similar to the lipid arrangement of biological membranes. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Modes for Carrying out the Invention

The examples hereinbelow describe the production of humanized and variant anti-VEGF antibodies with desirable properties from a therapeutic perspective including: (a) strong binding affinity for the VEGF antigen; (b) an ability to inhibit VEGF-induced proliferation of endothelial cells in vitro; and (c) the ability to inhibit VEGF-induced angiogenesis in vivo.

Antibody affinities may be determined as described in the examples hereinbelow. Preferred humanized or variant antibodies are those which bind human VEGF with a $K_d$ value of no more than about $1 \times 10^{-7}$ M; preferably no more than about $1 \times 10^{-8}$ M; and most preferably no more than about $5 \times 10^{-9}$ M.

Aside from antibodies with strong binding affinity for human VEGF, it is also desirable to select humanized or variant antibodies which have other beneficial properties from a therapeutic perspective. For example, the antibody may be one which inhibits endothelial cell growth in response to VEGF. In one embodiment, the antibody may be able to inhibit bovine capillary endothelial cell proliferation in response to a near maximally effective concentration of VEGF (3 ng/ml). Preferably, the antibody has an effective dose 50 (ED50) value of no more than about 5 nM, preferably no more than about 1 nM, and most preferably no more than about 0.5 nM, for inhibiting VEGF-induced proliferation of endothelial cells in this "endothelial cell growth assay", i.e., at these concentrations the antibody is able to inhibit VEGF-induced endothelial cell growth in vitro by 50%. A preferred "endothelial cell growth assay" involves culturing bovine adrenal cortex-derived capillary endothelial cells in the presence of low glucose Dulbecco's modified Eagle's medium (DMEM) (GIBCO) supplemented with 10% calf serum, 2 mM glutamine, and antibiotics (growth medium), essentially as described in Example 1 below. These endothelial cells are seeded at a density of $6 \times 10^3$ cells per well, in 6-well plates in growth medium. Either parent anti-VEGF antibody (control), humanized or variant anti-VEGF antibody is then added at concentrations ranging between 1 and 5000 ng/ml. After 2-3 hr, purified VEGF was added to a final concentration of 3 ng/ml. For specificity control, each antibody may be added to endothelial cells at the concentration of 5000 ng/ml, either alone or in the presence of 2 ng/ml bFGF. After five or six days, cells are dissociated by exposure to trypsin and counted in a Coulter counter (Coulter Electronics, Hialeah, Fla.). Data may be analyzed by a four-parameter curve fitting program (KaleidaGraph).

The preferred humanized or variant anti-VEGF antibody may also be one which has in vivo tumor suppression activity. For example, the antibody may suppress the growth of human A673 rhabdomyosarcoma cells or breast carcinoma MDA-MB-435 cells in nude mice. For in vivo tumor studies, human A673 rhabdomyosarcoma cells (ATCC; CRL 1598) or MDA-MB-435 cells (available from the ATCC) are cultured in DMEM/F12 supplemented with 10% fetal bovine serum, 2 mM glutamine and antibiotics as described in Example 1 below. Female BALB/c nude mice, 6-10 weeks old, are injected subcutaneously with $2 \times 10^6$ tumor cells in the dorsal area in a volume of 200 µl. Animals are then treated with the humanized or variant antibody and a control antibody with no activity in this assay. The humanized or variant anti-VEGF MAb is administered at a dose of 0.5 and/or 5 mg/kg. Each MAb is administered twice weekly intra peritoneally in a volume of 100 µl, starting 24 hr after tumor cell inoculation. Tumor size is determined at weekly intervals. Four weeks after tumor cell inoculation, animals are euthanized and the tumors are removed and weighed. Statistical analysis may be performed by ANOVA. Preferably, the antibody in this "in vivo tumor assay" inhibits about 50-100%, preferably about 70-100% and most preferably about 80-100% human A673 tumor cell growth at a dose of 5 mg/kg.

In the preferred embodiment, the humanized or variant antibody fails to elicit an immunogenic response upon administration of a therapeutically effective amount of the antibody to a human patient. If an immunogenic response is elicited, preferably the response will be such that the antibody still provides a therapeutic benefit to the patient treated therewith.

The humanized or variant antibody is also preferably one which is able to inhibit VEGF-induced angiogenesis in a human, e.g. to inhibit human tumor growth and/or inhibit intraocular angiogenesis in retinal disorders.

Preferred antibodies bind the "epitope A4.6.1" as herein defined. To screen for antibodies which bind to the epitope on human VEGF bound by an antibody of interest (e.g., those which block binding of the A4.6.1 antibody to human VEGF), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

The antibodies of the preferred embodiment herein have a heavy chain variable domain comprising an amino acid sequence represented by the formula: FR1-CDRH1-FR2-CDRH2-FR3-CDRH3-FR4, wherein "FR1-4" represent the four framework regions and "CDRH1-3" represent the three hypervariable regions of an anti-VEGF antibody variable heavy domain. FR1-4 may be derived from a "consensus sequence" (i.e. the most common amino acids of a class, subclass or subgroup of heavy or light chains of human immunoglobulins) as in the examples below or may be derived from an individual human antibody framework region or from a combination of different framework region sequences. Many human antibody framework region sequences are compiled in Kabat et al., supra, for example. In one preferred embodiment, the variable heavy FR is provided by a consensus sequence of a human immunoglobulin subgroup as compiled by Kabat et al., supra. Preferably, the human immunoglobulin subgroup is human heavy chains subgroup III (e.g. as in SEQ ID NO:11).

The human variable heavy FR sequence preferably has substitutions therein, e.g. wherein the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue may be selected by phage display (see Example 2 below). Exemplary variable heavy FR residues which may be substituted include any one or more of FR residue numbers: 37H, 49H, 67H, 69H, 71H, 73H, 75H, 76H, 78H, 94H (Kabat residue numbering employed here). Preferably at least two, or at least three, or at least four of these residues are substituted. A particularly preferred combination of FR substitutions is: 49H, 69H, 71H, 73H, 76H, 78H, and 94H.

With respect to the heavy chain hypervariable regions, these preferably have amino acid sequences as follows:

CDRH1

GYX$_1$X$_2$X$_3$X$_4$YGX$_5$N (SEQ ID NO:117), wherein X$_1$ is D, T or E, but preferably is D or T; X$_2$ is F, W, or Y, but preferably is F; X$_3$ is T, Q, G or S, but preferably is T; X$_4$ is H or N; and X$_5$ is M or I, but preferably is M.

CDRH2

WINTX$_1$TGEPTYAADFKR (SEQ ID NO:118), wherein X$_1$ is Y or W, but preferably is Y.

CDRH3

YPX$_1$YX$_2$X$_3$X$_4$X$_5$HWYFDV (SEQ ID NO:119), wherein X$_1$ is H or Y; X$_2$ is Y, R, K, I, T, E, or W, but preferably is Y; X$_3$ is G, N, A, D, Q, E, T, K, or S, but preferably is G; X$_4$ is S, T, K, Q, N, R, A, E, or G, but preferably is S or T; and X$_5$ is S or G, but preferably is S.

The heavy chain variable domain optionally comprises what has been designated "CDR7" herein within (i.e. forming part of) FR3 (see FIGS. 9B and 10B), wherein CDR7 may have the following amino acid sequence:

CDR7

X$_1$SX$_2$DX$_3$X$_4$X$_5$X$_6$TX$_7$ (SEQ ID NO:120), wherein X$_1$ is F, I, V, L, or A, but preferably is F; X$_2$ is A, L, V, or I, but preferably is L; X$_3$ is T, V or K, but preferably is T; X$_4$ is S or W, but preferably is S; X$_5$ is S, or K, but preferably is K; X$_6$ is N, or S, but preferably is S; and X$_7$ is V, A, L or I, but preferably is A.

The antibodies of the preferred embodiment herein have a light chain variable domain comprising an amino acid sequence represented by the formula: FR1-CDRL1-FR2-CDRL2-FR3—CDRL3-FR4, wherein "FR1-4" represent the four framework regions and "CDRL1-3" represent the three hypervariable regions of an anti-VEGF antibody variable heavy domain. FR1-4 may be derived from a "consensus sequence" (i.e. the most common amino acids of a class, subclass or subgroup of heavy or light chains of human immunoglobulins) as in the examples below or may be derived from an individual human antibody framework region or from a combination of different framework region sequences. In one preferred embodiment, the variable light FR is provided by a consensus sequence of a human immunoglobulin subgroup as compiled by Kabat et al., supra. Preferably, the human immunoglobulin subgroup is human kappa light chains subgroup I (e.g. as in SEQ ID NO:12).

The human variable light FR sequence preferably has substitutions therein, e.g. wherein the human FR residue is replaced by a corresponding mouse residue, but replacement with the nonhuman residue is not necessary. For example, a replacement residue other than the corresponding nonhuman residue may be selected by phage display (see Example 2 below). Exemplary variable light FR residues which may be substituted include any one or more of FR residue numbers: 4L, 46L and 71L (Kabat residue numbering employed here). Preferably only 46L is substituted. In another embodiment, both 4L and 46L are substituted.

With respect to the CDRs, these preferably have amino acid sequences as follows:

CDRL1

X$_1$AX$_2$X$_3$X$_4$X$_5$SNYLN (SEQ ID NO:121), wherein X$_1$ is R or S, but preferably is S; X$_2$ is S or N, but preferably is S; X$_3$ is Q or E, but preferably is Q; X$_4$ is Q or D, but preferably is D; and X$_5$ is I or L, but preferably is I.

```
CDRL2
FTSSLHS.           (SEQ ID NO:122)
```

CDRL3

QQYSX$_1$X$_2$PWT (SEQ ID NO:123), wherein X$_1$ is T, A or N, but preferably is T; and X$_2$ is V or T, but preferably is V.

Preferred humanized anti-VEGF antibodies are those having the heavy and/or light variable domain sequences of F(ab)-12 in Example 1 and variants thereof such as affinity matured forms including variants Y0317, Y0313-1 and Y0238-3 in Example 3, with Y0317 being the preferred variant. Methods for generating humanized anti-VEGF antibodies of interest herein are elaborated in more detail below.

A. Antibody Preparation

Methods for humanizing nonhuman VEGF antibodies and generating variants of anti-VEGF antibodies are described in the examples below. In order to humanize an anti-VEGF antibody, the nonhuman antibody starting material is prepared. Where a variant is to be generated, the parent antibody is prepared. Exemplary techniques for generating such nonhuman antibody starting material and parent antibodies will be described in the following sections.

(i) Antigen Preparation

The VEGF antigen to be used for production of antibodies may be, e.g., intact VEGF or a fragment of VEGF (e.g. a VEGF fragment comprising "epitope A4.6.1"). Other forms of VEGF useful for generating antibodies will be apparent to those skilled in the art. The VEGF antigen used to generate the antibody, is preferably human VEGF, e.g. as described in Leung et al., *Science* 246:1306 (1989), and Houck et al., *Mol. Endocrin.* 5:1806 (1991).

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iv) Humanization and Amino Acid Sequence Variants

Examples 1-2 below describe procedures for humanization of an anti-VEGF antibody. In certain embodiments, it may be desirable to generate amino acid sequence variants of these humanized antibodies, particularly where these improve the binding affinity or other biological properties of the humanized antibody. Example 3 describes methodologies for generating amino acid sequence variants of an anti-VEGF antibody with enhanced affinity relative to the parent antibody.

Amino acid sequence variants of the anti-VEGF antibody are prepared by introducing appropriate nucleotide changes into the anti-VEGF antibody DNA, or by peptide synthesis. Such variants include, for example, deletions from, and/or insertions into and/or substitutions of, residues within the amino acid sequences of the anti-VEGF antibodies of the examples herein. Any combination of deletion, insertion, and substitution is made to arrive at the final construct, provided that the final construct possesses the desired characteristics. The amino acid changes also may alter post-translational processes of the humanized or variant anti-VEGF antibody, such as changing the number or position of glycosylation sites.

A useful method for identification of certain residues or regions of the anti-VEGF antibody that are preferred locations for mutagenesis is called "alanine scanning mutagenesis," as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with VEGF antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-VEGF antibody variants are screened for the desired activity. Alanine scanning mutagenesis is described in Example 3.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-VEGF antibody with an N-terminal methionyl residue or the antibody fused to an epitope tag. Other insertional variants of the anti-VEGF antibody molecule include the fusion to the N- or C-terminus of the anti-VEGF antibody of an enzyme or a polypeptide which increases the serum half-life of the antibody (see below).

Another type of variant is an amino acid substitution variant. These variants have at least one amino acid residue in the anti-VEGF antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the humanized or variant anti-VEGF antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display (see Example 3 herein). Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis (see Example 3) can be performed to identified hypervariable region residues contributing significantly to antigen binding. Alternatively, or in addition, it may be beneficial to analyze a crystal structure of the antigen-antibody complex to identify contact points between the antibody and human VEGF. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-VEGF antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-VEGF antibody.

(v) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807. Human antibodies can also be derived from phage-display libraries (Hoogenboom et al., *J. Mol. Biol.*, 227:381 (1991); Marks et al., *J. Mol. Biol.*, 222:581-597 (1991); and U.S. Pat. Nos. 5,565,332 and 5,573,905). As discussed above, human antibodies may also be generated by in vitro activated B cells (see U.S. Pat. Nos. 5,567,610 and 5,229,275)

(vi) Antibody Fragments

In certain embodiments, the humanized or variant anti-VEGF antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form F(ab')$_2$ fragments (Carter et al., *Bio/Technology* 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

(vii) Multispecific Antibodies

In some embodiments, it may be desirable to generate multispecific (e.g. bispecific) humanized or variant anti-VEGF antibodies having binding specificities for at least two different epitopes. Exemplary bispecific antibodies may bind to two different epitopes of the VEGF protein. Alternatively, an anti-VEGF arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the VEGF-expressing cell. Bispecific antibodies may also be used to localize cytotoxic agents to cells which express VEGF. These antibodies possess an VEGF-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. Shalaby et al., *J. Exp. Med.* 175:217-225 (1992).

Various techniques for making and isolating bispecific antibody fragments directly from recombinant cell culture have also been described. For example, bispecific antibodies have been produced using leucine zippers. Kostelny et al., *J. Immunol* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994). Alternatively, the bispecific antibody may be a "linear antibody" produced as described in Zapata et al. *Protein Eng.* 8(10):1057-1062 (1995).

Antibodies with more than two valencies are contemplated. For example, trispecific antibodies can be prepared. Tutt et al., *J. Immunol.* 147:60 (1991).

(viii) Other Modifications

Other modifications of the humanized or variant anti-VEGF antibody are contemplated. For example, it may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

The invention also pertains to immunoconjugates comprising the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. A variety of radionuclides are available for the production of radioconjugated anti-VEGF antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionuclide).

The anti-VEGF antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide interchange reaction. A chemotherapeutic agent (such as Doxorubicin) is optionally contained within the liposome. See Gabizon et al., *J. National Cancer Inst.* 81(19):1484 (1989)

The antibody of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-VEGF antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984)).

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence: PKNSSMISNTP (SEQ ID NO:17), and optionally further comprises a sequence selected from the group consisting of HQSLGTQ (SEQ ID NO:18), HQNLSDGK (SEQ ID NO:19), HQNISDGK (SEQ ID NO:20), or VISSHLGQ (SEQ ID NO:21), particularly where the antibody fragment is a Fab or F(ab')$_2$. In another most preferred embodiment, the salvage receptor binding epitope is a polypeptide containing the sequence(s): HQNLSDGK (SEQ ID NO:19), HQNISDGK (SEQ ID NO:20), or VISSHLGQ (SEQ ID NO:21) and the sequence: PKNSSMISNTP (SEQ ID NO:17).

Covalent modifications of the humanized or variant anti-VEGF antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

B. Vectors, Host Cells and Recombinant Methods

The invention also provides isolated nucleic acid encoding the humanized or variant anti-VEGF antibody, vectors and host cells comprising the nucleic acid, and recombinant techniques for the production of the antibody.

For recombinant production of the antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-VEGF antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-VEGF antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus*(mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-VEGF antibody production and cultured in conventional nutrient media modified as appropriate for inducing promoters, selecting transformants, or amplifying the genes encoding the desired sequences The host cells used to produce the anti-VEGF antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 1 02:255 (1980), U.S. Pat. Nos. 4,767,704; 4,657,866; 4,927,762; 4,560,655; or 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al, *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., *J. Immunol. Meth.* 62:1-13 (1983)). Protein G is recommended for all mouse isotypes and for human $\gamma 3$ (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

C. Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other (see Section F below). Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules)

or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibody

The antibodies of the invention may be used as affinity purification agents. In this process, the antibodies are immobilized on a solid phase such a Sephadex resin or filter paper, using methods well known in the art. The immobilized antibody is contacted with a sample containing the VEGF protein (or fragment thereof) to be purified, and thereafter the support is washed with a suitable solvent that will remove substantially all the material in the sample except the VEGF protein, which is bound to the immobilized antibody. Finally, the support is washed with another suitable solvent, such as glycine buffer, pH 5.0, that will release the VEGF protein from the antibody.

Anti-VEGF antibodies may also be useful in diagnostic assays for VEGF protein, e.g., detecting its expression in specific cells, tissues, or serum. Such diagnostic methods may be useful in cancer diagnosis.

For diagnostic applications, the antibody typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-VEGF antibody need not be labeled, and the presence thereof can be detected using a labeled antibody which binds to the VEGF antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyte for binding with a limited amount of antibody. The amount of VEGF protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

E. Diagnostic Kits

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

For therapeutic applications, the anti-VEGF antibodies of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The antibodies also are suitably administered by intra tumoral, peritumoral, intralesional, or perilesional routes, to exert local as well as systemic therapeutic effects. The intraperitoneal route is expected to be particularly useful, for example, in the treatment of ovarian tumors.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

The anti-VEGF antibodies are useful in the treatment of various neoplastic and non-neoplastic diseases and disorders. Neoplasms and related conditions that are amenable to treatment include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Non-neoplastic conditions that are amenable to treatment include rheumatoid arthritis, psoriasis, atherosclerosis, diabetic and other proliferative retinopathies including retinopathy of prematurity, retrolental fibroplasia, neovascular glaucoma, age-related macular degeneration, thyroid hyperplasias (including Grave's disease), corneal and other tissue transplantation, chronic inflammation, lung inflammation, nephrotic syndrome, preeclampsia, ascites, pericardial effusion (such as that associated with pericarditis), and pleural effusion.

Age-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VEGF antibodies of the present invention are expected to be especially useful in reducing the severity of AMD.

Depending on the type and severity of the disease, about 1 μg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging.

According to another embodiment of the invention, the effectiveness of the antibody in preventing or treating disease may be improved by administering the antibody serially or in combination with another agent that is effective for those purposes, such as tumor necrosis factor (TNF), an antibody capable of inhibiting or neutralizing the angiogenic activity of acidic or basic fibroblast growth factor (FGF) or hepatocyte growth factor (HGF), an antibody capable of inhibiting or neutralizing the coagulant activities of tissue factor, protein C, or protein S (see Esmon et al., PCT Patent Publication No. WO 91/01753, published 21 Feb. 1991), an antibody capable of binding to HER2 receptor (see Hudziak et al., PCT Patent Publication No. WO 89/06692, published 27 Jul. 1989), or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. Such other agents may be present in the composition being administered or may be administered separately. Also, the antibody is suitably administered serially or in combination with radiological treatments, whether involving irradiation or administration of radioactive substances.

In one embodiment, vascularization of tumors is attacked in combination therapy. The antibody and one or more other anti-VEGF antagonists are administered to tumor-bearing patients at therapeutically effective doses as determined for example by observing necrosis of the tumor or its metastatic foci, if any. This therapy is continued until such time as no further beneficial effect is observed or clinical examination shows no trace of the tumor or any metastatic foci. Then TNF is administered, alone or in combination with an auxiliary agent such as alpha-, beta-, or gamma-interferon, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see Esmon et al., PCT Patent Publication No. WO 91/01753, published 21 Feb. 1991), or heat or radiation.

Since the auxiliary agents will vary in their effectiveness it is desirable to compare their impact on the tumor by matrix screening in conventional fashion. The administration of anti-VEGF antibody and TNF is repeated until the desired clinical effect is achieved. Alternatively, the anti-VEGF antibody is administered together with TNF and, optionally, auxiliary agent(s). In instances where solid tumors are found in the limbs or in other locations susceptible to isolation from the general circulation, the therapeutic agents described herein are administered to the isolated tumor or organ. In other embodiments, a FGF or platelet-derived growth factor (PDGF) antagonist, such as an anti-FGF or an anti-PDGF neutralizing antibody, is administered to the patient in conjunction with the anti-VEGF antibody. Treatment with anti-VEGF antibodies optimally may be suspended during periods of wound healing or desirable neovascularization.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-VEGF antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLE 1

This example describes the production of humanized anti-VEGF antibodies with desirable properties from a therapeutic standpoint.

Materials and Methods

Cloning of Murine A4.6.1 MAb and Construction of Mouse-Human Chimeric Fab: The murine anti-VEGF mAb A4.6.1 has been previously described by Kim et al., *Growth Factors* 7:53 (1992) and Kim et al. *Nature* 362:841 (1993). Total RNA was isolated from hybridoma cells producing the anti-VEGF Mab A.4.6.1 using RNAsol (TEL-TEST) and reverse-transcribed to cDNA using Oligo-dT primer and the SuperScript II system (GIBCO BRL, Gaithersburg, Md.). Degenerate oligonucleotide primer pools, based of the N-terminal amino acid sequences of the light and heavy chains of the antibody, were synthesized and used as forward primers. Reverse primers were based on framework 4 sequences obtained from murine light chain subgroup kV and heavy chain subgroup II (Kabat et al. *Sequences of Proteins of Immunological Interest* 5th ed. Public Health Service, National Institutes of Health, Bethesda, Md. (1991)). After polymerase chain reaction (PCR) amplification, DNA fragments were ligated to a TA cloning vector (Invitrogen, San Diego, Calif.). Eight clones each of the light and heavy chains were sequenced. One clone with a consensus sequence for the light chain VL domain and one with a consensus sequence for the heavy chain VH domain were subcloned respectively into the pEMX1 vector containing the human CL and CH1 domains (Werther et al. *J. Immunol.* 157:4986-4995 (1996)), thus generating a mouse-human chimera. This chimeric F(ab) consisted of the entire murine A4.6.1 VH domain fused to a human CH1 domain at amino acid SerH113 and the entire murine A4.6.1 VL domain fused to a human CL domain at amino acid LysL107. Expression and purification of the chimeric F(ab) were identical to that of the humanized F(ab)s. The chimeric F(ab) was used as the standard in the binding assays.

Computer Graphics Models of Murine and Humanized F(ab): Sequences of the VL and VH domains (FIGS. 1A and 1B) were used to construct a computer graphics model of the murine A4.6.1 VL-VH domains. This model was used to determine which framework residues should be incorporated into the humanized antibody. A model of the humanized F(ab) was also constructed to verify correct selection of murine framework residues. Construction of models was performed as described previously (Carter et al. *Proc. Natl. Acad. Sci. USA* 89:4285-4289 (1992) and Eigenbrot et al. *J. Mol. Biol.* 229:969-995 (1993)).

Construction of Humanized F(ab)s: The plasmid pEMX1 used for mutagenesis and expression of F(ab)s in *E. coli* has been described previously (Werther et al., supra). Briefly, the plasmid contains a DNA fragment encoding a consensus human κ subgroup I light chain (VLκI-CL) and a consensus human subgroup III heavy chain (VHIII-CH1) and an alkaline phosphatase promoter. The use of the consensus sequences for VL and VH has been described previously (Carter et al., supra).

To construct the first F(ab) variant of humanized A4.6.1, F(ab)-1, site-directed mutagenesis (Kunkel et al., *Proc. Natl. Acad. Sci. USA* 82:488-492 (1985)) was performed on a deoxyuridine-containing template of pEMX1. The six CDRs according to Kabat et al., supra, were changed to the murine A4.6.1 sequence. F(ab)-1 therefore consisted of a complete human framework (VL κ subgroup I and VH subgroup III) with the six complete murine CDR sequences. Plasmids for all other F(ab) variants were constructed from the plasmid template of F(ab)-1. Plasmids were transformed into *E. coli* strain XL-1 Blue (Stratagene, San Diego, Calif.) for preparation of double- and single-stranded DNA. For each variant, DNA coding for light and heavy chains was completely sequenced using the dideoxynucleotide method (Sequenase, U.S. Biochemical Corp., Cleveland, Ohio). Plasmids were transformed into *E coli* strain 16C9, a derivative of MM294, plated onto Luria broth plates containing 50 µg/ml carbenicillin, and a single colony selected for protein expression. The single colony was grown in 5 ml Luria broth-100 mg/ml carbenicillin for 5-8 h at 37° C. The 5 ml culture was added to 500 ml AP5-50 µg/ml carbenicillin and allowed to grow for 20 h in a 4 L baffled shake flask at 30° C. AP5 media consists of: 1.5 g glucose, 11.0 g Hycase SF, 0.6 g yeast extract (certified), 0.19 g MgSO4 (anhydrous), 1.07 g NH4Cl, 3.73 g KCl, 1.2 g NaCl, 120 ml 1 M triethanolamine, pH 7.4, to 1 L water and then sterile filtered through 0.1 mm Sealkeen filter. Cells were harvested by centrifugation in a 1 L centrifuge bottle at 3000×g and the supernatant removed. After freezing for 1 h, the pellet was resuspended in 25 ml cold 10 mM Tris-1 mM EDTA-20% sucrose, pH 8.0. 250 ml of 0.1 M benzamidine (Sigma, St. Louis, Mo.) was added to inhibit proteolysis. After gentle stirring on ice for 3 h, the sample was centrifuged at 40,000×g for 15 min. The supernatant was then applied to a protein G-Sepharose CL-4B (Pharmacia, Uppsala, Sweden) column (0.5 ml bed volume) equilibrated with 10 mM Tris-1 mM EDTA, pH 7.5. The column was washed with 10 ml of 10 mM Tris-1 mM EDTA, pH 7.5, and eluted with 3 ml 0.3 M glycine, pH 3.0, into 1.25 ml 1 M Tris, pH 8.0. The F(ab) was then buffer exchanged into PBS using a Centricon-30 (Amicon, Beverly, Mass.) and concentrated to a final volume of 0.5 ml. SDS-PAGE gels of all F(ab)s were run to ascertain purity and the molecular weight of each variant was verified by electrospray mass spectrometry.

Construction and Expression of Chimeric and Humanized IgG: For generation of human IgG1 variants of chimeric (chIgG1) and humanized (huIgG1) A4.6.1, the appropriate murine or humanized VL and VH (F(ab)-12, Table 2) domains were subcloned into separate, previously described, pRK vectors (Eaton et al., *Biochemistry* 25:8343-8347 (1986)). The DNA coding for the entire light and the entire heavy chain of each variant was verified by dideoxynucleotide sequencing.

For transient expression of variants, heavy and light chain plasmids were co-transfected into human 293 cells (Graham et al., *J. Gen. Virol.* 36:59-74 (1977)), using a high efficiency procedure (Gorman et al., *DNA Prot. Eng. Tech.* 2:3-10 (1990)). Media was changed to serum-free and harvested daily for up to five days. Antibodies were purified from the pooled supernatants using protein A-Sepharose CL-4B (Pharmacia). The eluted antibody was buffer exchanged into PBS using a Centricon-30 (Amicon), concentrated to 0.5 ml, sterile filtered using a Millex-GV (Millipore, Bedford, Mass.) and stored at 4° C.

For stable expression of the final humanized IgG1 variant (rhuMAb VEGF), Chinese hamster ovary (CHO) cells were transfected with dicistronic vectors designed to coexpress both heavy and light chains (Lucas et al., *Nucleic Acid Res.* 24:1774-79 (1996)). Plasmids were introduced into DP12 cells, a proprietary derivative of the CHO-K1 DUX B11 cell line developed by L. Chasin (Columbia University), via lipofection and selected for growth in GHT-free medium (Chisholm, V. High efficiency gene transfer in mammalian cells. In: Glover, D M, Hames, B D. *DNA Cloning* 4. *Mammalian systems*. Oxford Univ. Press, Oxford pp 1-41 (1996)). Approximately 20 unamplified clones were randomly chosen and reseeded into 96 well plates. Relative specific productivity of each colony was monitored using an ELISA to quantitate the full length human IgG accumulated in each well after 3 days and a fluorescent dye, Calcien AM, as a surrogate marker of viable cell number per well. Based on these data, several unamplified clones were chosen for further amplification in the presence of increasing concentrations of methotrexate. Individual clones surviving at 10, 50, and 100 nM methotrexate were chosen and transferred to 96 well plates for productivity screening. One clone, which reproducibly exhibited high specific productivity, was expanded in T-flasks and used to inoculate a spinner culture. After several passages, the suspension-adapted cells were used to inoculate production cultures in GHT-containing, serum-free media supplemented with various hormones and protein hydrolysates. Harvested cell culture fluid containing rhuMAb VEGF was purified using protein A-Sepharose CL-4B. The purity after this step was ~99%. Subsequent purification to homogeneity was carried out using an ion exchange chromatography step. The endotoxin content of the final purified antibody was <0.10 eu/mg.

F(ab) and IgG Quantitation: For quantitating F(ab) molecules, ELISA plates were coated with 2 μg/ml goat anti-human IgG Fab (Organon Teknika, Durham, N.C.) in 50 mM carbonate buffer, pH 9.6, at 4° C. overnight and blocked with PBS-0.5% bovine serum albumin (blocking buffer) at room temperature for 1 h. Standards (0.78-50 ng/ml human F(ab)) were purchased from Chemicon (Temecula, Calif.). Serial dilutions of samples in PBS-0.5% bovine serum albumin-0.05% polysorbate 20 (assay buffer) were incubated on the plates for 2 h. Bound F(ab) was detected using horseradish peroxidase-labeled goat anti-human IgG F(ab) (Organon Teknika), followed by 3,3',5,5'-tetramethylbenzidine (Kirkegaard & Perry Laboratories, Gaithersburg, Md.) as the substrate. Plates were washed between steps. Absorbance was read at 450 nm on a Vmax plate reader (Molecular Devices, Menlo Park, Calif.). The standard curve was fit using a four-parameter nonlinear regression curve-fitting program. Data points which fell in the range of the standard curve were used for calculating the F(ab) concentrations of samples. The concentration of full-length antibody was determined using goat anti-human IgG Fc (Cappel, Westchester, Pa.) for capture and horseradish peroxidase-labeled goat anti-human Fc (Cappel) for detection. Human IgG1 (Chemicon) was used as standard.

VEGF Binding Assay: For measuring the VEGF binding activity of F(ab)s, ELISA plates were coated with 2 μg/ml rabbit F(ab')$_2$ to human IgG Fc (Jackson ImmunoResearch, West Grove, Pa.) and blocked with blocking buffer (described above). Diluted conditioned medium containing 3 ng/ml of KDR-IgG (Park et al., *J. Biol. Chem.* 269:25646-25645 (1994)) in blocking buffer were incubated on the plate for 1 h. Standards (6.9-440 ng/ml chimeric F(ab)) and two-fold serial of samples were incubated with 2 nM biotinylated VEGF for 1 h in tubes. The solutions from the tubes were then transferred to the ELISA plates and incubated for 1 h. After washing, biotinylated VEGF bound to KDR was detected using horseradish peroxidase-labeled streptavidin (Zymed, South San Francisco, Calif. or Sigma, St. Louis, Mo.) followed by 3,3',5,5'-tetramethylbenzidine as the substrate. Titration curves were fit with a four-parameter non-linear regression curve-fitting program (KaleidaGraph, Synergy Software, Reading Pa.). Concentrations of F(ab) variants corresponding to the midpoint absorbance of the titration curve of the standard were calculated and then divided by the concentration of the standard corresponding to the midpoint absorbance of the standard titration curve. Assays for full-length IgG were the same as for the F(ab)s except that the assay buffer contained 10% human serum.

BIAcore™ Biosensor Assay: VEGF binding of the humanized and chimeric F(ab)s were compared using a BIAcore™ biosensor (Karlsson et al. *Methods: A Comparison to Methods in Enzymology* 6:97-108 (1994)). Concentrations of F(ab)s were determined by quantitative amino acid analysis. VEGF was coupled to a CM-5 biosensor chip through primary amine groups according to manufacturer's instructions (Pharmacia). Off-rate kinetics were measured by saturating the chip with F(ab) (35 μl of 2 μM F(ab) at a flow rate of 20 μl/min) and then switching to buffer (PBS-0.05% polysorbate 20). Data points from 0-4500 sec were used for off-rate kinetic analysis. The dissociation rate constant ($k_{off}$) was obtained from the slope of the plot of ln(R0/R) versus time, where R0 is the signal at t=0 and R is the signal at each time point.

On-rate kinetics were measured using two-fold serial dilutions of F(ab) (0.0625-2 mM). The slope, $K_s$, was obtained from the plot of ln(−dR/dt) versus time for each F(ab) concentration using the BIAcore™ kinetics evaluation software as described in the Pharmacia Biosensor manual. R is the signal at time t. Data between 80 and 168, 148, 128, 114, 102, and 92 sec were used for 0.0625, 0.125, 0.25, 0.5, 1, and 2 mM F(ab), respectively. The association rate constant ($k_{on}$) was obtained from the slope of the plot of $K_s$ versus F(ab) concentration. At the end of each cycle, bound F(ab) was removed by injecting 5 µl of 50 mM HCl at a flow rate of 20 µl/min to regenerate the chip.

Endothelial Cell Growth Assay: Bovine adrenal cortex-derived capillary endothelial cells were cultured in the presence of low glucose Dulbecco's modified Eagle's medium (DMEM) (GIBCO) supplemented with 10% calf serum, 2 mM glutamine, and antibiotics (growth medium), essentially as previously described (Leung et al. *Science* 246:1306-1309 (1989)). For mitogenic assays, endothelial cells were seeded at a density of $6 \times 10^3$ cells per well, in 6-well plates in growth medium. Either muMAb VEGF A.4.6.1 or rhuMAb VEGF was then added at concentrations ranging between 1 and 5000 ng/ml. After 2-3 hr, purified *E. coli*-expressed rhVEGF165 was added to a final concentration of 3 ng/ml. For specificity control, each antibody was added to endothelial cells at the concentration of 5000 ng/ml, either alone or in the presence of 2 ng/ml bFGF. After five or six days, cells were dissociated by exposure to trypsin and counted in a Coulter counter (Coulter Electronics, Hialeah, Fla.). The variation from the mean did not exceed 10%. Data were analyzed by a four-parameter curve fitting program (KaleidaGraph).

In Vivo Tumor Studies: Human A673 rhabdomyosarcoma cells (ATCC; CRL 1598) were cultured as previously described in DMEM/F12 supplemented with 10% fetal bovine serum, 2 mM glutamine and antibiotics (Kim et al. *Nature* 362:841-844 (1993) and Borgström et al. *Cancer Res.* 56:4032-4039 (1996)). Female BALB/c nude mice, 6-10 weeks old, were injected subcutaneously with $2 \times 10^6$ tumor cells in the dorsal area in a volume of 200 µl. Animals were then treated with muMAb VEGF A.4.6.1, rhuMAb VEGF or a control MAb directed against the gp120 protein (Kim et al. *Nature* 362:841-844 (1993)). Both anti-VEGF MAbs were administered at the doses of 0.5 and 5 mg/kg; the control MAb was given at the dose of 5 mg/kg. Each MAb was administered twice weekly intra peritoneally in a volume of 100 µl, starting 24 hr after tumor cell inoculation. Each group consisted of 10 mice. Tumor size was determined at weekly intervals. Four weeks after tumor cell inoculation, animals were euthanized and the tumors were removed and weighed. Statistical analysis was performed by ANOVA.

Results

Humanization: The consensus sequence for the human heavy chain subgroup III and the light chain subgroup κ I were used as the framework for the humanization (Kabat et al., supra) (FIGS. 1A and 1B). This framework has been successfully used in the humanization of other murine antibodies (Werther et al, supra; Carter et al, supra; Presta et al *J. Immunol.* 151:2623-2632 (1993); and Eigenbrot et al *Proteins* 18:49-62 (1994)). CDR-H1 included residues H26-H35. The other CDRs were according to Kabat et al, supra. All humanized variants were initially made and screened for binding as F(ab)s expressed in *E. coli*. Typical yields from 500 ml shake flasks were 0.1-0.4 mg F(ab).

The chimeric F(ab) was used as the standard in the binding assays. In the initial variant, F(ab)-1, the CDR residues were transferred from the murine antibody to the human framework and, based on the models of the murine and humanized F(ab)s, the residue at position H49 (Ala in human) was changed to the murine Gly. In addition, F(ab)s which consisted of the chimeric heavy chain/F(ab)-1 light chain (F(ab)-2) and F(ab)-1 heavy chain/chimeric light chain (F(ab)-3) were generated and tested for binding. F(ab)-1 exhibited a binding affinity greater than 1000-fold reduced from the chimeric F(ab) (Table 2). Comparing the binding affinities of F(ab)-2 and F(ab)-3 suggested that framework residues in the F(ab)-1 VH domain needed to be altered in order to increase binding.

TABLE 2

Binding of Humanized Anti-VEGF F(ab) Variants to VEGF[a]

| Variant | Template | Changes[b] | Purpose | EC50 F(ab)-X / EC50 chimeric F(ab)c Mean | S.D. | N |
|---|---|---|---|---|---|---|
| chim-F(ab) | Chimeric F(ab) | | | 1.0 | | |
| F(ab)-1 | Human FR | | Straight CDR swap AlaH49Gly | >1350 | | 2 |
| F(ab)-2 | | | Chimera Light Chain F(ab)-1 Heavy Chain | >145 | | 3 |
| F(ab)-3 | | | F(ab)-1 Light Chain Chimera Heavy Chain | 2.6 | 0.1 | 2 |
| F(ab)-4 | F(ab)-1 | ArgH71Leu AsnH73Thr | CDR-H2 conformation Framework | >295 | | 3 |
| F(ab)-5 | F(ab)-4 | LeuL46Val | VL-VH interface | 80.9 | 6.5 | 2 |
| F(ab)-6 | F(ab)-5 | LeuH78Ala | CDR-H1 conformation | 36.4 | 4.2 | 2 |
| F(ab)-7 | F(ab)-5 | IleH69Phe | CDR-H2 conformation | 45.2 | 2.3 | 2 |
| F(ab)-8 | F(ab)-5 | IleH69Phe LeuH78Ala | CDR-H2 conformation CDR-H1 conformation | 9.6 | 0.9 | 4 |
| F(ab)-9 | F(ab)-8 | GlyH49Ala | CDR-H2 conformation | >150 | | 2 |
| F(ab)-10 | F(ab)-8 | AsnH76Ser | Framework | 6.4 | 1.2 | 4 |
| F(ab)-11 | F(ab)-10 | LysH75Ala | Framework | 3.3 | 0.4 | 2 |
| F(ab)-12 | F(ab)-10 | ArgH94Lys | CDR-H3 conformation | 1.6 | 0.6 | 4 |

[a]Anti-VEGF F(ab) variants were incubated with biotinylated VEGF and then transferred to ELISA plates coated with KDR-IgG (Park et al., supra).
[b]Murine residues are underlined; residue numbers are according to Kabat et al., supra.
[c]Mean and standard deviation are the average of the ratios calculated for each of the independent assays; the EC50 for chimeric F(ab) was 0.049 ± 0.013 mg/ml (1.0 nM).

Changing human residues H71 and H73 to their murine counterparts in F(ab)-4 improved binding by 4-fold (Table 2). Inspection of the models of the murine and humanized F(ab)s suggested that residue L46, buried at the VL-VH interface and interacting with CDR-H3 (FIG. 2), might also play a role either in determining the conformation of CDR-H3 and/or affecting the relationship of the VL and VH domains. When the murine Val was exchanged for the human Leu at L46 (F(ab)-5), the binding affinity increased by almost 4-fold (Table 2). Three other buried framework residues were evaluated based on the molecular models: H49, H69 and H78. Position H69 may affect the conformation of CDR-H2 while position H78 may affect the conformation of CDR-H1 (FIG. 2). When each was individually changed from the human to murine counterpart, the binding improved by 2-fold in each case (F(ab)-6 and F(ab)-7, Table 2). When both were simultaneously changed, the improvement in binding was 8-fold (F(ab)-8, Table 2). Residue H49 was originally included as the murine Gly; when changed to the human consensus counterpart Ala the binding was reduced by 15-fold (F(ab)-9, Table 2).

In F(ab)-10 and F(ab)-11 two residues in framework loop 3, FR-3, were changed to their murine counterparts: AsnH76 to murine Ser (F(ab)-10) and LysH75 to murine Ala (F(ab)-11). Both effected a relatively small improvement in binding (Table 2). Finally, at position H94 human and murine sequences most often have an Arg (Kabat et al., supra). In F(ab)-12, this Arg was replaced by the rare Lys found in the murine antibody (FIG. 1A) and this resulted in binding which was less than 2-fold from the chimeric F(ab) (Table 2). F(ab)-12 was also compared to the chimeric F(ab) using the BIAcore™ system (Pharmacia). Using this technique the $K_d$ of the humanized F(ab)-12 was 2-fold weaker than that of the chimeric F(ab) due to both a slower $k_{on}$ and faster $k_{off}$ (Table 3).

TABLE 3

Binding of Anti-VEGF F(ab) Variants to VEGF Using the BIAcore ™ System[a]

| Variant | Amount of (Fab) bound (RU) | $k_{off}$ $(s^{-1})$ | kon $(M^{-1}s^{-1})$ | Kd (nM) |
|---|---|---|---|---|
| chim-F(ab)[b] | 4250 | 5.9 × 10−5 | 6.5 × 104 | 0.91 |
| F(ab)-12 | 3740 | 6.3 × 10−5 | 3.5 × 104 | 1.8 |

[a]The amount of F(ab) bound, in resonance units (RU), was measured using a BIAcore ™ system when 2 μg F(ab) was injected onto a chip containing 2480 RU immobilized VEGF. Off-rate kinetics (koff) were measured by saturating the chip with F(ab) and then monitoring dissociation after switching to buffer. On-rate kinetics ($k_{on}$) were measured using two-fold serial dilutions of F(ab). $K_d$, the equilibrium dissociation constant, was calculated as $k_{off}/k_{on}$.
[b]chim-F(ab) is a chimeric F(ab) with murine VL and VH domains fused to human CL and CH1 heavy domains.

Full length mAbs were constructed by fusing the VL and VH domains of the chimeric F(ab) and variant F(ab)-12 to the constant domains of human k light chain and human IgG1 heavy chain. The full length 12-IgG1 (F(ab)-12 fused to human IgG1) exhibited binding which was 1.7-fold weaker than the chimeric IgG1 (Table 4). Both 12-IgG1 and the chimeric IgG1 bound slightly less well than the original murine mAb A4.6.1 (Table 4).

TABLE 4

Binding of Anti-VEGF IgG Variants to VEGF[a] IgG1/chIgG1[b]

| Variant | Mean | S.D. | N |
|---|---|---|---|
| chIgG1 | 1.0 | | 2 |
| murIgG1[c] | 0.759 | 0.001 | 2 |
| 12-IgG1[d] | 1.71 | 0.03 | 2 |

[a]Anti-VEGF IgG variants were incubated with biotinylated VEGF and then transferred to ELISA plates coated with KDR-IgG (Park et al., (1994), supra).
[b]chIgG1 is chimeric IgG1 with murine VL and VH domains fused to human CL and IgG1 heavy chains; the EC50 for chIgG1 was 0.113 ± 0.013 μg/ml (0.75 nM).
[c]murIgG1 is muMAbVEGF A461 purified from ascites.
[d]12-IgG1 is F(ab)-12 VL and VH domains fused to human CL and IgG1 heavy chains.

Biological Studies: rhuMAb VEGF and muMAb VEGF A.4.6.1. were compared for their ability to inhibit bovine capillary endothelial cell proliferation in response to a near maximally effective concentration of VEGF (3 ng/ml). As illustrated in FIG. 3, the two MAbs were essentially equivalent, both in potency and efficacy. The ED50 values were respectively 50±5 ng/ml and 48±8 ng/ml (~0.3 nM). In both cases 90% inhibition was achieved at the concentration of 500 ng/ml (~3 nM). Neither muMAb VEGF A.4.6.1 nor rhuMAb VEGF had any effect on basal or bFGF-stimulated proliferation of capillary endothelial cells, confirming that the inhibition is specific for VEGF.

To determine whether such equivalency applies also to an in vivo system, the two antibodies were compared for their ability to suppress the growth of human A673 rhabdomyosarcoma cells in nude mice. Previous studies have shown that muMAb VEGF A.4.6.1 has a dramatic inhibitory effect in this tumor model (Kim et al. Nature 362:841-844 (1993) and Borgström et al. Cancer Res 56:4032-4039 (1996)). As shown in FIG. 4, at both doses tested (0.5 and 5 mg/kg), the two antibodies markedly suppressed tumor growth as assessed by tumor weight measurements four weeks after cell inoculation. The decreases in tumor weight compared to the control group were respectively 85% and 93% at each dose in the animals treated with muMAb VEGF A.4.6.1. versus 90% and 95% in those treated with rhuMAb VEGF. Similar results were obtained with the breast carcinoma cell line MDA-MB 435.

EXAMPLE 2

In this example, the murine anti-VEGF antibody A4.6.1 discussed above was humanized by randomizing a small set of framework residues and by monovalent display of the resultant library of antibody molecules on the surface of filamentous phage in order to identify high affinity framework sequences via affinity-based selection.

Materials and Methods

Construction of Anti-VEGF Phagemid Vector, pMB4-19: The murine anti-VEGF mAb A4.6.1 is discussed above in Example 1. The first Fab variant of humanized A4.6.1, hu2.0, was constructed by site-directed mutagenesis using a deoxyuridine-containing template of plasmid pAK2 (Carter et al. Proc. Natl. Acad. Sci. U.S.A. 89:4285-4289 (1992)) which codes for a human $V_L\kappa I$-$C\kappa_1$ light chain and human $V_H III$-$C_H 1\gamma_1$ heavy chain Fd fragment The transplanted A4.6.1 CDR sequences were chosen according to the sequence definition of Kabat et al., supra, except for CDR-H1 which included residues 26-35. The Fab encoding sequence was subcloned into the phagemid vector phGHamg3 (Bass et al. *Proteins* 8:309-314 (1990) and Lowman et al. *Biochemistry* 30:10832-10838 (1991)). This construct, pMB4-19, encodes the initial humanized A4.6.1 Fab, hu2.0, with the C-terminus of the heavy chain fused precisely to the carboxyl portion of the M13 gene III coat protein. pMB4-19 is similar in construction to pDH188, a previously described plasmid for monovalent display of Fab fragments (Garrard et al. *Biotechnology* 9:1373-1377 (1991)). Notable differences between pMB4-19 and pDH188 include a shorter M13 gene III segment (codons 249-406) and use of an amber stop codon immediately following the antibody heavy chain Fd fragment. This permits expression of both secreted heavy chain or heavy chain-gene III fusions in supE suppressor strains of *E. coli*.

Expression and Purification of Humanized A4.6.1 Fab Fragment: *E. coli* strain 34B8, a nonsuppressor, was transformed with phagemid pMB4-19, or variants thereof. Single colonies were grown overnight at 37° C. in 5 mL 2YT containing 50 μg/mL carbenicillin. These cultures were diluted into 200 mL AP5 medium (Chang et al. *Gene* 55:189-196 (1987)) containing 20 μg/mL carbenicillin and incubated for 26 hr at 30° C. The cells were pelleted at 4000×g and frozen at −20° C. for at least 2 h. Cell pellets were then resuspended in 5 mL of 10 mM Tris-HCl (pH 7.6) containing 1 mM EDTA, shaken at 4° C. for 90 min and centrifuged at 10,000×g for 15 min. The supernatant was applied to a 1 mL streptococcal protein G-sepharose column (Pharmacia) and washed with 10 mL of 10 mM MES (pH 5.5). The bound Fab fragment was eluted with 2.5 mL 100 mM acetic acid and immediately neutralized with 0.75 mL 1 M Tris-HCl, pH 8.0. Fab preparations were buffer-exchanged into PBS and concentrated using Centricon-30 concentrators (Amicon). Typical yields of Fab were ~1 mg/L culture, post-protein G purification. Purified Fab samples were characterized by electrospray mass spectrometry, and concentrations were determined by amino acid analysis.

Construction of the Anti-VEGF Fab Phagemid Library: The humanized A4.6.1 phagemid library was constructed by site-directed mutagenesis according to the method of Kunkel et al. *Methods Enzymol.* 204:125-139 (1991)). A derivative of pMB4-19 containing TAA stop triplets at $V_H$ codons 24, 37, 67 and 93 was prepared for use as the mutagenesis template (all sequence numbering according to Kabat et al., supra). This modification was to prevent subsequent background contamination by wild type sequences. The codons targeted for randomization were 4 and 71 (light chain) and 24, 37, 67, 69, 71, 73, 75, 76, 78, 93 and 94 (heavy chain).

In order to randomize heavy chain codons 67, 69, 71, 73, 75, 76, 78, 93 and 94 with a single mutagenic oligonucleotide, two 126-mer oligonucleotides were first preassembled from 60 and 66-mer fragments by template-assisted enzymatic ligation. Specifically, 1.5 nmol of 5' phosphorylated oligonucleotide 503-1 (5'-GAT TTC AAA CGT CGT NYT ACT WTT TCT AGA GAC AAC TCC AAA AAC ACA BYT TAC CTG CAG ATG AAC-3' (SEQ ID NO:22)) or 503-2 (5'-GAT TTC AAA CGT CGT NYT ACT WTT TCT TTA GAC ACC TCC GCA AGC ACA BYT TAC CTG CAG ATG AAC-3' (SEQ ID NO:23)) were combined with 1.5 nmol of 503-3 (5'-AGC CTG CGC GCT GAG GAC ACT GCC GTC TAT TAC TGT DYA ARG TAC CCC CAC TAT TAT GGG-3' (SEQ ID NO:24)) (randomized codons underlined; N=A/G/T/C; W=A/T; B=G/T/C; D=G/A/T; R=A/G; Y=C/T). Then, 1.5 nmol of template oligonucleotide (5'-CTC AGC GCG CAG GCT GTT CAT CTG CAG GTA-3' (SEQ ID NO:25)), with complementary sequence to the 5' ends of 503-½ and the 3' end of 503-3, was added to hybridize to each end of the ligation junction. Taq ligase (thermostable ligase from New England Biolabs) and buffer were added, and the reaction mixture was subjected to 40 rounds of thermal cycling, (95° C. 1.25 min; 50° C. for 5 min) so as to cycle the template oligonucleotide between ligated and unligated junctions. The product 126-mer oligonucleotides were purified on a 6% urea/TBE polyacrylamide gel and extracted from the polyacrylamide in buffer. The two 126-mer products were combined in equal ratio, ethanol precipitated and finally solubilized in 10 mM Tris-HCl, 1 mM EDTA. The mixed 126-mer oligonucleotide product was labeled 504-01.

Randomization of select framework codons ($V_L$ 4, 71; $V_H$ 24, 37, 67, 69, 71, 73, 75, 76, 93, 94) was effected in two steps. Firstly, $V_L$ randomization was achieved by preparing three additional derivatives of the modified pMB4-19 template. Framework codons 4 and 71 in the light chain were replaced individually or pairwise using the two mutagenic oligonucleotides 5'-GCT GAT ATC CAG TTG ACC CAG TCC CCG-3' (SEQ ID NO:26) 5'-and TCT GGG ACG GAT TAC ACT CTG ACC ATC-3' (SEQ ID NO:27). Deoxyuridine-containing template was prepared from each of these new derivatives. Together with the original template, these four constructs coded for each of the four possible light chain framework sequence combinations (Table 5).

Oligonucleotides 504-1, a mixture of two 126-mer oligonucleotides (see above), and 5'-CGT TTG TCC TGT GCA RYT TCT GGC TAT ACC TTC ACC AAC TAT GGT ATG AAC TGG RTC CGT CAG GCC CCG GGT AAG-3' (SEQ ID NO:28) were used to randomize heavy chain framework codons using each of the four templates just described. The four libraries were electroporated into *E. coli* XL-1 Blue cells (Stratagene) and combined. The total number of independent transformants was estimated at $>1.2 \times 10^8$, approximately 1,500-fold greater than the maximum number of DNA sequences in the library.

A variety of systems have been developed for the functional display of antibody fragments on the surface of filamentous phage. Winter et al., *Ann. Rev. Immunol* 12,433 (1994). These include the display of Fab or single chain Fv (scFv) fragments as fusions to either the gene III or gene VIII coat proteins of M13 bacteriophage. The system selected herein is similar to that described by Garrard et al., *Biotechn*, 9,1373 (1991) in which a Fab fragment is monovalently displayed as a gene III fusion (FIG. 7). This system has two notable features. In particular, unlike scFvs, Fab fragments have no tendency to form dimeric species, the presence of which can prevent selection of the tightest binders due to avidity effects. Additionally the monovalency of the displayed protein eliminates a second potential source of avidity effects that would otherwise result from the presence of multiple copies of a protein on each phagemid particle. Bass and Wells, *Proteins* 8:309 (1990) and Lowman et al., *Biochemistry* 30:10832 (1991).

Phagemid particles displaying the humanized A4.6.1 Fab fragments were propagated in *E. coli* XL-1 Blue cells. Briefly, cells harboring the randomized pMB4-19 construct were grown overnight at 37° C. in 25 mL 2YT medium containing 50 μg/mL carbenicillin and approximately $10^{10}$ M13KO7 helper phage (Vieira & Messing *Methods Enzymol.* 153:3-11 (1987)). Phagemid stocks were purified from culture supernatants by precipitation with a saline polyethylene glycol solution, and resuspended in 100 μL PBS (~$10^{14}$ phagemid/mL)

Selection of Humanized A4.6.1 Fab Variants: Purified VEGF$_{121}$ (100 µL at 10 µg/mL in PBS) was coated onto a microtiter plate well overnight at 4° C. The coating solution was discarded and this well, in addition to an uncoated well, were blocked with 6% skim milk for 1 h and washed with PBS containing 0.05% TWEEN 20™ (detergent). Then, 10 µL of phagemid stock, diluted to 100 µL with 20 mM Tris (pH 7.5) containing 0.1% BSA and 0.05% TWEEN 20™, was added to each well. After 2 hours the wells were washed and the bound phage eluted with 100 µL of 0.1M glycine (pH 2.0), and neutralized with 25 µL of 1 M Tris pH 8.0. An aliquot of this was used to titer the number of phage eluted. The remaining phage eluted from the VEGF-coated well were propagated for use in the next selection cycle. A total of 8 rounds of selection was performed after which time 20 individual clones were selected and sequenced (Sanger et al. Proc. Natl. Acad. Sci. U.S.A. 74:5463-5467 (1977)).

Determination of VEGF Binding Affinities: Association ($k_{on}$) and dissociation ($k_{off}$) rate constants for binding of humanized A4.6.1 Fab variants to VEGF$_{121}$ were measured by surface plasmon resonance (Karlsson et al. J. Immun. Methods 145:229-240 (1991)) on a Pharmacia BIAcore instrument. VEGF$_{121}$ was covalently immobilized on the biosensor chip via primary amino groups. Binding of humanized A4.6.1 Fab variants was measured by flowing solutions of Fab in PBS/0.05% TWEEN 20™ over the chip at a flow rate of 20 µL/min. Following each binding measurement, residual Fab was stripped from the immobilized ligand by washing with 5 µL of 50 mM aqueous HCl at 3 µL/min. Binding profiles were analyzed by nonlinear regression using a simple monovalent binding model (BIAevaluation software v2.0; Pharmacia).

Results

Construction of Humanized A4.6.1: An initial humanized A4.6.1 Fab fragment was constructed (hu2.0, FIGS. 5A and 5B), in which the CDRs from A4.6.1 were grafted onto a human, V$_L$κI-V$_H$III framework. All other residues in hu2.0 were maintained as the human sequence. Binding of this variant to VEGF was so weak as to be undetectable. Based on the relative affinity of other weakly-binding humanized A4.6.1 variants, the K$_D$ for binding of hu2.0 was estimated at >7 µM. This contrasts with an affinity of 1.6 nM for a chimeric Fab construct consisting of the intact V$_L$ and V$_H$ domains from murine A4.6.1 and human constant domains. Thus binding of hu2.0 to VEGF was at least 4000-fold reduced relative to the chimera.

Design of Antibody Library: The group of framework changes to the human framework sequence herein is shown in Table 5 and FIG. 6.

TABLE 5

Key Framework Residues Important for Antigen Binding and Targeted for Randomization

| Framework residue | | Human VK$_L$I, V$_H$III consensus residue | Murine A4.6.1 residue | Randomization[a] |
|---|---|---|---|---|
| V$_L$: | 4 | Met | Met | Met, Leu |
| | 71 | Phe | Tyr | Phe, Tyr |
| V$_H$: | 24 | Ala | Ala | Ala, Val, Thr |
| | 37 | Val | Val | Val, Ile |

TABLE 5-continued

Key Framework Residues Important for Antigen Binding and Targeted for Randomization

| Framework residue | Human VK$_L$I, V$_H$III consensus residue | Murine A4.6.1 residue | Randomization[a] |
|---|---|---|---|
| 67 | Phe | Phe | Phe, Val, Thr, Leu, Ile, Ala |
| 69 | Ile | Phe | Ile, Phe |
| 71 | Arg | Leu | Arg[b], Leu[b] |
| 73 | Asp | Thr | Asp[b], Thr[b] |
| 75 | Lys | Ala | Lys[b], Ala[b] |
| 76 | Asn | Ser | Asn[b], Ser[b] |
| 78 | Leu | Ala | Leu, Ala, Val, Phe |
| 93 | Ala | Ala | Ala, Val, Leu, Ser, Thr |
| 94 | Arg | Lys | Arg, Lys |

[a]Amino acid diversity in phagemid library
[b]V$_H$71, 73, 75, 76 randomized to yield the all-murine (L71/T73/A75/S76) or all-human (R71/D73/K75/N76) V$_H$III tetrad A concern in designing the humanized A4.6.1 phagemid library was that residues targeted for randomization were widely distributed across the V$_L$ and V$_H$ sequences. Limitations in the length of synthetic oligonucleotides requires that simultaneous randomization of each of these framework positions can only be achieved through the use of multiple oligonucleotides. However, as the total number of oligonucleotides increases, the efficiency of mutagenesis decreases (i.e. the proportion of mutants obtained which incorporate sequence derived from all of the mutagenic oligonucleotides). To circumvent this problem, two features were incorporated into the library construction. The first was to prepare four different mutagenesis templates coding for each of the possible V$_L$ framework combinations. This was simple to do given the limited diversity of the light chain framework (only 4 different sequences), but was beneficial in that it eliminated the need for two oligonucleotides from the mutagenesis strategy. Secondly, two 126-base oligonucleotides were preassembled from smaller synthetic fragments. This made possible randomization of V$_H$ codons 67, 69, 71, 73, 75, 76, 93 and 94 with a single long oligonucleotide, rather than two smaller ones. The final randomization mutagenesis strategy therefore employed only two oligonucleotides simultaneously onto four different templates.

Selection of Tight Binding Humanized A4.6.1 Fab's: Variants from the humanized A4.6.1 Fab phagemid library were selected based on binding to VEGF. Enrichment of functional phagemid, as measured by comparing titers for phage eluted from a VEGF-coated versus uncoated microtiter plate well, increased up to the seventh round of affinity panning. After one additional round of sorting, 20 clones were sequenced to identify preferred framework residues selected at each position randomized. These results, summarized in Table 6, revealed strong consensus amongst the clones selected. Ten out of the twenty clones had the identical DNA sequence, designated hu2.10. Of the thirteen framework positions randomized, eight substitutions were selected in hu2.10 (V$_L$ 71; V$_H$ 37, 71, 73, 75, 76, 78 and 94). Interestingly, residues V$_H$ 37 (Ile) and 78 (Val) were selected neither as the human V$_H$III or murine A4.6.1 sequence. This result suggests that some framework positions may benefit from extending the diversity beyond the target human and parent murine framework sequences.

TABLE 6

Sequences Selected from the Humanized A4.6.1 Phagemid Fab Library

Residue substitutions

| Variant | $V_L$ | | $V_H$ | | | | | | | | | | |
|---|---|---|---|---|---|---|---|---|---|---|---|---|---|
| | 4 | 71 | 24 | 37 | 67 | 69 | 71 | 73 | 75 | 76 | 78 | 93 | 94 |
| murine A4.6.1 | M | Y | A | V | F | F | L | T | A | S | A | A | K |
| hu2.0 (CDR-graft) | M | E | A | V | F | I | R | N | K | N | L | A | R |
| *Phage-selected clones:* | | | | | | | | | | | | | |
| hu2.1(2) | — | Y | — | I | — | — | — | — | — | — | V | — | K |
| hu2.2(2) | L | Y | — | I | — | — | — | — | — | — | V | — | K |
| hu2.6(1) | L | — | — | I | T | — | L | T | A | S | V | — | K |
| hu2.7(1) | L | — | — | I | — | — | — | — | — | — | V | — | K |
| hu2.10(10) | — | Y | — | I | — | — | L | T | A | S | V | — | K |

Differences between hu2.0 and murine A4.6.1 antibodies are underlined.
The number of identical clones identifies for each phage-selected sequence is indicated in parentheses.
Dashes in the sequences of phage-selected clones indicate selection of the human $V_L$KI-$V_H$III framework sequence (i.e. as in hu2.0).

There were four other unique amino acid sequences among the remaining ten clones analyzed: hu2.1, hu2.2, hu2.6 and hu2.7. All of these clones, in addition to hu2.10, contained identical framework substitutions at positions $V_H$ 37 (Ile), 78 (Val) and 94 (Lys), but retained the human $V_H$III consensus sequence at positions 24 and 93. Four clones had lost the light chain coding sequence and did not bind VEGF when tested in a phage ELISA assay (Cunningham et al. *EMBO J.* 13:2508-251 (1994)). Such artifacts can often be minimized by reducing the number of sorting cycles or by propagating libraries on solid media.

Expression and Binding Affinity of Humanized A4.6.1 Variants: Phage-selected variants hu2.1, hu2.2, hu2.6, hu2.7 and hu2.10 were expressed in *E. coli* using shake flasks and Fab fragments were purified from periplasmic extracts by protein G affinity chromatography. Recovered yields of Fab for these five clones ranged from 0.2 (hu2.6) to 1.7 mg/L (hu2.1). The affinity of each of these variants for antigen (VEGF) was measured by surface plasmon resonance on a BIAcore instrument (Table 7). Analysis of this binding data revealed that the consensus clone hu2.10 possessed the highest affinity for VEGF out of the five variants tested. Thus the Fab phagemid library was selectively enriched for the tightest binding clone. The calculated $K_D$ for hu2.10 was 55 nM, at least 125-fold tighter than for hu2.0 which contains no framework changes ($K_D$>7 µM). The other four selected variants all exhibited weaker binding to VEGF, ranging down to a $K_D$ of 360 nM for the weakest (hu2.7). Interestingly, the $K_D$ for hu2.6, 67 nM, was only marginally weaker than that of hu2.10 and yet only one copy of this clone was found among 20 clones sequenced. This may have due to a lower level of expression and display, as was the case when expressing the soluble Fab of this variant. However, despite the lower expression rate, this variant is useful as a humanized antibody.

TABLE 7

VEGF Binding Affinity of Humanized A4.6.1 Fab Variants

| Variant | $k_{on}$ $M^{-1}s^{-1}/10^4$ | $k_{off}$ $10^4 s^{-1}$ | $K_D$ nM | $K_D(A4.6.1)$ $K_D(mut)$ |
|---|---|---|---|---|
| A4.6.1 chimera | 5.4 | 0.85 | 1.6 | >4000 |
| hu2.0 | ND | ND | >7000** | |
| *Phage selected clones:* | | | | |
| hu2.1 | 0.70 | 18 | 260 | 170 |
| hu2.2 | 0.47 | 16 | 340 | 210 |
| hu2.6 | 0.67 | 4.5 | 67 | 40 |
| hu2.7 | 0.67 | 24 | 360 | 230 |
| hu2.10 | 0.63 | 3.5 | 55 | 35 |
| *hu2.10V | 2.0 | 1.8 | 9.3 | 5.8 |

*hu2.10V = hu2.10 with mutation $V_L$ Leu–>Val
Estimated errors in the Biacore binding measurements are +/−25%.
**Too weak to measure; estimate of lower bound Additional Improvement of Humanized Variant hu2.1: Despite the large improvement in antigen affinity over the initial humanized variant, binding of hu2.10 to VEGF was still 35-fold weaker than a chimeric Fab fragment containing the murine A4.6.1 $V_L$ and $V_H$ domains. This considerable difference suggested that further optimization of the humanized framework might be possible through additional mutations. Of the Vernier residues identified by Foote & Winter *J. Mol. Biol.* 224:487-499 (1992), only residues $V_L$ 46, $V_H$ 2 and $V_H$ 48 differed in the A4.6.1 versus human $V_L$κI-$V_H$III framework (FIGS. 5A and 5B) but were not randomized in our phagemid library. A molecular model of the humanized A4.6.1 Fv fragment showed that $V_L$ 46 sits at the $V_L$-$V_H$ interface and could influence the conformation of CDR-H3. Furthermore, this amino acid is almost always leucine in most $V_L$κ frameworks (Kabat et al., supra), but is valine in A4.6.1. Accordingly, a Leu -> Val substitution was made at this position in the background of hu2.10. Analysis of binding kinetics for this new variant, hu2.10V, indicated a further 6-fold improvement in the $K_D$ for VEGF binding, demonstrating the importance of valine at position $V_L$ 46 in antibody A4.6.1. The $K_D$ for hu2.10V (9.3 nM) was thus within 6-fold that of the chimera. In contrast to $V_L$ 46, no improvement in the binding affinity of hu2.10 was observed for replacement of either $V_H$ 2 or $V_H$ 48 with the corresponding residue from murine A4.6.1.

EXAMPLE 3

In this example, CDR randomization, affinity maturation by monovalent Fab phage display, and cumulative combination of mutations were used to enhance the affinity of a humanized anti-VEGF antibody.

Construction of Humanized Antibody pY0101: Phage-displayed antibody vector phMB4-19-1.6 (see FIGS. 8A-E) was used as a parent. In this construct, anti-VEGF is expressed as a Fab fragment with its heavy chain fused to the N-terminus of the truncated g3p. Both the light and heavy chains are under the control of phoA promoter with an upstream stII signal-sequence for secretion into the periplasm. Point mutations outside the CDR regions were made by site-directed mutagenesis to improve affinity for VEGF with oligonucleotides HL-242, HL-243, HL-245, HL-246, HL-254, HL-256, and HL-257 as shown in Table 8 below:

TABLE 8

Oligos for Directed Mutations

| Oligo Number | Region | Substitution/ Comments | Sequence | |
|---|---|---|---|---|
| HL-242 | VL | M4L | 5'-GATATCCAGTTGACCCAGTCCCCG-3' | (SEQ ID NO:29) |
| HL-243 | VL | L46V | 5'-GCTCCGAAAGTACTGATTTAC-3' | (SEQ ID NO:30) |
| HL-245 | VH | CDR-7 | 5'-CGTCGTTTCACTTTTCTGCAGACACCT CCAGCAACACAGTATACCTGCAGATG-3' | (SEQ ID NO:31) |
| HL-246 | VH | R98K | 5'-CTATTACTGTGCAAAGTACCCCCAC-3' | (SEQ ID NO:32) |
| HL-254 | VL | Y71F | 5'-GGGACGGATTTCACTCTGACCATC-3' | (SEQ ID NO:33) |
| HL-256 | VH | I37V | 5'-GGTATGAACTGGGTCCGTCAGGCCCC-3' | (SEQ ID NO:34) |
| HL-257 | VH | CDR-7 A72L S76K N77S | 5'-CGTCGTTTCACTTTTCTTTAGACACCT CCAAAAGCACAGCATACCTGCAGATGAAC-3' | (SEQ ID NO:35) |

The resulting variant was termed Y0101 (FIGS. 9A and 9B).

Construction of the First Generation of Antibody-Phage Libraries: To prevent contamination by wild-type sequence, templates with the TAA stop codon at the targeted sites for randomization were prepared and used for constructing libraries by site-directed mutagenesis with oligonucleotides using the degenerate NNS codon (where N is an equal mixture of A, G, C, and T while S is an equal mixture of G and C) for saturation mutagenesis. VL1 and VH3 were chosen as potential candidates for affinity enhancement (FIGS. 9A and B). Within the CDRs, two libraries were constructed from the pY0101 template. VL1 was mutated using stop-template oligonucleotides HL-248 and HL-249 (Table 9) and library oligonucleotides HL-258 and HL-259 (Table 10). Similarly, three libraries were constructed for VH3 using stop template oligonucleotides HL-250, HL-251, and HL-252 (Table 9), and library oligonucleotides HL-260, HL-261, and HL-262 (Table 10). Library construction is summarized in Tables 9 and 10 below.

TABLE 9

Template Oligos for Mutagenesis

| Oligo Number | Region Comments | Sequence | |
|---|---|---|---|
| HL-248 | VL1 | 5'-GGGTCACCATCACCTGCTAAGCATAATAATAATAAAGCAACTA TTTAAACTGG-3' | (SEQ ID NO:36) |
| HL-249 | VL1 | 5'-GCGCAAGTCAGGATATTTAATAATAATAATAATGGTATCAACAG AAACCAGG-3' | (SEQ ID NO:37) |
| HL-250 | VH3 | 5'-GTCTATTACTGTGCAAAGTAATAACACTAATAAGGGAGCAGCC ACTGG-3' | (SEQ ID NO:38) |
| HL-251 | VH3 | 5'-GGTACCCCCACTATTATTAATAATAATAATGGTATTTCGACGTC TGGGG-3' | (SEQ ID NO:39) |
| HL-252 | VH3 | 5'-CACTATTATGGGAGCAGCCACTAATAATAATAAGTCTGGGTCA AGGAACCCTG-3' | (SEQ ID NO:40) |
| HL-263 | VH1 | 5'-TCCTGTGCAGCTTCTGGCTAATAATTCTAATAATAAGGTATGAA CTGGGTCCG-3' | (SEQ ID NO:41) |
| HL-264 | VH2 | 5'-GAATGGGTTGGATGGATTAACTAATAATAAGGTTAACCGACCT ATGCTGCGG-3' | (SEQ ID NO:42) |
| YC-80 | VH3 | 5'-CTGTGCAAAGTACCCGTAATATTAATAATAATAACACTGGTATT TCGAC-3' | (SEQ ID NO:43) |
| YC-100 | CDR7 | 5'-CGTTTCACTTTTCTTAAGACTAATCCAAATAAACAGCATACCT GCAG-3' | (SEQ ID NO:44) |
| YC-102 | VH2 | 5'-GAATGGGTTGGATGGATTTAATAATAATAAGGTGAACCGACCT ATG-3' | (SEQ ID NO:45) |

TABLE 10

Random Oligos for Library Construction

| Oligo Number | Region Comment | Sequence | |
|---|---|---|---|
| HL-258 | VL1 | 5'-GGGTCACCATCACCTGCNNSGCANNSNNSNNSNNSAGC AACTATTTAAACTGG-3' | (SEQ ID NO:46) |
| HL-259 | VL1 | 5'-GCGCAAGTCAGGATATTNNSNNSNNSNNSNNSTGGTATCAACA GAAACCAGG-3' | (SEQ ID NO:47) |
| HL-260 | VH3 | 5'-GTCTATTACTGTGCAAAGNNSNNSCACNNSNNSGGGAGCAGC CACTGG-3' | (SEQ ID NO:48) |
| HL-261 | VH3 | 5'-GGTACCCCCACTATTATNNSNNSNNSNNSTGGTATTTCGACGT CTGGGG-3' | (SEQ ID NO:49) |
| HL-262 | VH3 | 5'-CACTATTATGGGAGCAGCCACNNSNNSNNSNNSGTCTGGGGT CAAGGAACCCTG-3' | (SEQ ID NO:50) |
| HL-265 | VH1 | 5'-TCCTGTGCAGCTTCTGGCNNSNNSTTCNNSNNSNNSGGTATGA ACTGGGTCCG-3' | (SEQ ID NO:51) |
| HL-266 | VH2 | 5'-GAATGGGTTGGATGGATTAACNNSNNSNNSGGTNNSCCGACC TATGCTGCGG-3' | (SEQ ID NO:52) |
| YC-81 | VH3 | 5'-CTGTGCAAAGTACCCGNNSTATNNSNNSNNSNNSCACTGGTAT TTCGAC-3' | (SEQ ID NO:53) |
| YC-101 | CDR7 | 5'-CGTTTCACTTTTTCTNNSGACNNSTCCAAANNSACAGCATACCT GCAG-3' | (SEQ ID NO:54) |
| YC-103 | VH2 | 5'-GAATGGGTTGGATGGATTNNSNNSNNSNNSGGTGAACCGACC TATG-3' | (SEQ ID NO:55) |

The products of random mutagenesis reactions were electroporated into XL1-Blue E. coli cells (Stratagene) and amplified by growing 15-16 h with M13KO7 helper phage. The complexity of each library, ranging from $2 \times 10^7$ to $1.5 \times 10^8$, was estimated based upon plating of the initial transformation onto carbenicillin plates.

Initial Affinity Selections: For each round of selection, approximately $10^9$-$10^{10}$ phage were screened for binding to plates (Nunc Maxisorp 96-well) coated with 2 μg/mL VEGF (recombinant; residue 9-109 version) in 50 mM carbonate buffer, pH 9.6 and blocked with 5% instant milk in 50 mM carbonate buffer, pH 9.6. After 1-2 hour binding at room temperature, in the presence of 0.5% bovine serum albumin and 0.05% TWEEN 20™ in PBS, the phage solution was removed, and the plate was washed ten times with PBS/TWEEN™ (0.05% TWEEN 20™ in PBS buffer). Typically, to select for enhanced affinity variants with slower dissociation rates, the plates were incubated with PBS/TWEEN™ buffer for a period of time which lengthened progressively for each round of selection (from 0 minute for the first round, to 3 h for the ninth round of selection). After the PBS/TWEEN™ buffer was removed, the remained phages were eluted with 0.1 M HCl and immediately neutralized with ⅓ volume of 1 M Tris, pH 8.0. The eluted phages were propagated by infecting XL1-Blue E. coli cells (Stratagene) for the next selection cycle.

Sequencing data revealed that both VL1 libraries, even after the eighth/ninth round of sorting, remained diverse, tolerating various type of residues at the sites of randomization. In contrast, the VH3 libraries retained only wild type residues or had very conservative substitutions. This suggested that the VL1 was more exposed to solvent and lay outside the binding interface. In contrast, VH3 did not show dramatically different sidechain substitutions, and therefore might be more intimately involved in antigen binding.

Phage-ELISA Assay of Binding Affinities: From each of these libraries, representative clones (those represented by abundant sequences) were assayed for their affinities relative to that of parent clone pY0101 in a phage-ELISA assay. In such an assay, phages were first serially diluted to determine a fractional saturation titer which was then held constant and used to incubate with varying concentrations of VEGF (starting at 200 nM to 0 nM) in solution. The mixture was then transferred onto plate precoated with VEGF (2 μg/mL) and blocked with 5% instant milk, and allowed to equilibrate for 1 hour at room temperature. Thereafter, the phage solution was removed and the remaining bound phages were detected with a solution of rabbit anti-phage antibody mixed with goat anti-rabbit conjugate of horse radish peroxidase. After an hour incubation at room temperature, the plate was developed with a chromogenic substrate, o-phenylenediamine (Sigma). The reaction was stopped with addition of ½ volume of 2.5 M $H_2SO_4$. Optical density at 492 nm was measured on a spectrophotometric plate reader.

Although all of the selected clones from these five libraries showed either weaker or similar affinities than that of wild type pY0101 in phage-ELISA assay, one particular variant (pY0192) from library HL-258 displayed an apparent advantage (about 10 fold) in the level of expression or phage display relative to pY0101. This clone contained mutations S24R, S26N, Q27E, D28Q, and I29L in the VL region (FIG. 9A). In addition, this variant was found to have a spurious mutation, M34I, in VH. This variant showed no significant difference in binding affinity to VEGF as compared with the pY0101 variant. To improve the level of Fab-display on phage, and the signal-to-noise ratio for phage-ELISA assays, the corresponding substitutions in pY0192 at VL1 were incorporated into the template background for constructing both CDR Ala-mutants and the second generation of anti-VEGF libraries.

Ala-Scanning the CDRs of Anti-VEGF: To determine the energetics contributed by each of the amino acids in the CDR regions and thus better select target residues for randomization, the CDR regions were screened by substituting alanine for each residue. Each Ala mutant was constructed using site-directed mutagenesis with a synthetic oligonucleotide encoding for the specific alanine substitution. Where Ala was the wild-type residue, Ser was substituted to test the effect of a sidechain substitution. Phage clones having a single Ala mutation were purified and assayed in phage-ELISA as described above. Results of the Ala-scan demonstrated that Ala-substitution at various positions can have an effect, ranging from 2 to >150 fold reductions, on antigen binding affinity compared to pY0192. In addition, it confirmed a previous observation that VH3, but not VL1, was involved in antigen binding. Results of the CDR Ala-scan are summarized in Table 11 below.

TABLE 11

Relative VEGF Affinities of Ala-Scan Fab Variants

| Residue VL | IC50 (mut) IC50 (wt) | Residue VH | IC50 (mut) IC50 (wt) |
|---|---|---|---|
| R24A | 1 | G26A | 2 |
| A25S | 1 | Y27A | 34 |
| N26A | 1 | T28A | 1 |
| E27A | 1 | F29A | 16 |
| Q28A | 1 | T30A | 1 |
| L29A | 1 | N31A | >150 |
| S30A | 2 | Y32A | >150 |
| N31A | 2 | G33A | 6 |
| Y32A | 2 | I34A | 6 |
| L33A | 2 | N35A | 66 |
| N34A | 4 | | |
| | | W50A | >150 |
| F50A | 1 | I51A | 4 |
| T51A | 1 | N52A | >150 |
| S52A | 1 | T53A | 9 |
| S53A | 1 | Y54A | 9 |
| L54A | 1 | T55A | 4 |
| H55A | 1 | G56A | 1 |
| S56A | 1 | E57A | 2 |
| | | P58A | 1 |
| Q89A | 4 | T59A | 3 |
| Q90A | 3 | Y60A | 2 |
| Y91A | 14 | A61S | 1 |
| S92A | 1 | A62S | 1 |
| T93A | 1 | D63A | 1 |
| V94A | 2 | F64A | 1 |
| P95A | 3 | K65A | 1 |
| W96A | >150 | R66A | 1 |
| T97A | 1 | | |
| | | Y99A | >150 |
| | | P100A | 38 |
| | | H101A | 4 |
| | | Y102A | 4 |
| | | Y103A | 5 |
| | | G104A | 2 |
| | | S105A | 1 |
| | | S106A | >150 |
| | | H107A | 2 |
| | | W108A | >150 |
| | | Y109A | 19 |
| | | F110A | 25 |
| | | D111A | 2 |

All variants are in the background of pY0192 ("wt"; see FIGS. 9A-B). IC50's were determined in a competitive phage-ELISA assay.

The largest effects of Ala substitutions are seen in CDRs H1, H2, and H3, including Y27A (34-fold reduction in affinity), N31A, Y32A, W50A, N52A, Y99A, S106A and W108A (each >150-fold reduction); N35A (66-fold reduction), P100A (38-fold reduction) and F110A (25-fold reduction). In contrast, only one VL substitution had a large impact on binding affinity, W96A (>150-fold reduction). These results point to the three VH CDRs as the main energetic determinants of Fab binding to VEGF, with some contribution from VL3.

Design of Second-Generation CDR Mutation Libraries: Two additional libraries which randomized existing residues in anti-VEGF version Y0192 were designed based upon inspection of the crystal structure. In VH2, residues 52-55 were randomized because they lie within the binding interface with VEGF. An additional region of the Fab, termed "CDR7" (see FIG. 10B), was also targeted for randomization because several residues in this loop, while not contacting VEGF, do have contacts with the VH loops of the antibody. These represented potential sites for affinity improvement through secondary effects upon the interface residues. Residues L72, T74, and S77 were randomized in this CDR7 library.

Also based upon the crystal structure, one of the original CDR libraries was reconstructed to re-test the potential for affinity maturation in the VH1 CDR. Residues 27, 28, and 30-32 were randomized using the new Y0192 background.

Second-Generation Selections of Anti-VEGF Libraries: Based on Ala-scan results as well as the crystal structure of the antigen-antibody (F(ab)-12) complex, a total of seventeen libraries were constructed using the pY0192 template and stop-template oligonucleotides (which code for a stop codon at the sites targeted for randomization) YC-80, YC-100, YC-102, HL-263, and HL-264 (Table 9 above). The corresponding randomization oligonucleotides (which employ NNS at the sites targeted for randomization) were YC81, YC-101, YC-103, HL-265, and HL-266 (Table 10 above). The resulting transformants yielded libraries with complexities ranging from $6 \times 10^7$ to $5 \times 10^8$ which suggests that the libraries were comprehensive in covering all possible variants. Phage libraries were sorted for 7-8 rounds using conditions as described in Table 12 below.

TABLE 12

Conditions for Secondary Selections of Fab Variants

| Round of Selection | Incubation Time (hr) | Incubation Solution | Incubation Temp. (° C.) |
|---|---|---|---|
| 1 | 0 | 0 | room temp. |
| 2 | 1 | ELISA buffer | room temp. |
| 3 | 2 | 1 μM VEGF/ELISA | room temp. |
| 4 | 18 | 1 μM VEGF/ELISA | room temp. |
| 5 | 37 | 1 μM VEGF/ELISA | room temp. |
| 6 | 17 hr @ room temp./30 hr @ 37° C. | 1 μM VEGF/ELISA | room temp./37° C. |
| 7 | 63 | 1 μM VEGF/ELISA | 37° C. |
| 8 | 121 | 1 μM VEGF/ELISA | 37° C. |

ELISA buffer contained 0.5% bovine serum albumin and 0.05% TWEEN 20™ in PBS. VEGF was included in the incubation buffer to minimize rebinding of phages to VEGF coated on the surface of the plate. Sorting of these libraries yielded phage enrichments over 7 to 8 rounds of selection.

Phage-ELISA Assays of Second Generation Clones: After eight round of selections, ten to twenty clones from each library were isolated from carbenicillin containing plates harboring E. coli (XL1) colonies which had been infected with an eluted phage pool. Colonies were isolated and grown with helper phage to obtain single-stranded DNA for sequencing. CDR substitutions selected for more favorable binding to VEGF were deduced from the DNA sequences of phagemid clones. A sampling of selected clones is shown in Table 13 below.

TABLE 13

Protein Sequences of Anti-VEGF Variants from Second Generation Fab-Phage Libraries Variants from library YC-81

| Name | VH3 sequence (residues 99-111) | |
|---|---|---|
| Y0238-1 | YPYYRGTSHWYFD | (SEQ ID NO:56) |
| Y0238-2 | YPYYINKSHWYFD | (SEQ ID NO:57) |
| Y0238-3 | YPYYYGTSHWYFD | (SEQ ID NO:58) |
| Y0238-4 | YPYYYNQSHWYFD | (SEQ ID NO:59) |
| Y0238-5 | YPYYIAKSHWYFD | (SEQ ID NO:60) |
| Y0238-6 | YPYYRDNSHWYFD | (SEQ ID NO:61) |
| Y0238-7 | YPYYWGTSHWYFD | (SEQ ID NO:62) |
| Y0238-8 | YPYYRQNSHWYFD | (SEQ ID NO:63) |
| Y0238-9 | YPYYRQSSHWYFD | (SEQ ID NO:64) |
| Y0238-10 | YPYYRNTSHWYFD | (SEQ ID NO:65) |
| Y0238-11 | YPYYKNTSHWYFD | (SEQ ID NO:66) |
| Y0238-12 | YPYYIERSHWYFD | (SEQ ID NO:67) |
| Y0228-21 | YPYYRNASHWYFD | (SEQ ID NO:68) |
| Y0228-22 | YPYYTTRSHWYFD | (SEQ ID NO:69) |
| Y0228-23 | YPYYEGSSHWYFD | (SEQ ID NO:70) |
| Y0228-24 | YPYYRQRGHWYFD | (SEQ ID NO:71) |
| Y0228-26 | YPYYTGRSHWYFD | (SEQ ID NO:72) |
| Y0228-27 | YPYYTNTSHWYFD | (SEQ ID NO:73) |
| Y0228-28 | YPYYRKGSHWYFD | (SEQ ID NO:74) |
| Y0228-29 | YPYYTGSSHWYFD | (SEQ ID NO:75) |
| Y0228-30 | YPYYRSGSHWYFD | (SEQ ID NO:76) |
| Y0229-20 | YPYYTNRSHWYFD | (SEQ ID NO:77) |
| Y0229-21 | YPYYRNSSHWYFD | (SEQ ID NO:78) |
| Y0229-22 | YPYYKESSHWYFD | (SEQ ID NO:79) |
| Y0229-23 | YPYYRDASHWYFD | (SEQ ID NO:80) |
| Y0229-24 | YPYYRQKGHWYFD | (SEQ ID NO:81) |
| Y0229-25 | YPYYKGGSHWYFD | (SEQ ID NO:82) |
| Y0229-26 | YPYYYGASHWYFD | (SEQ ID NO:83) |
| Y0229-27 | YPYYRGESHWYFD | (SEQ ID NO:84) |
| Y0229-28 | YPYYRSTSHWYFD | (SEQ ID NO:85) |

TABLE 13-continued

Protein Sequences of Anti-VEGF Variants from Second Generation Fab-Phage Libraries Variants from library HL-265

| Name | VH1 sequence (residue 26-35) | |
|---|---|---|
| Y0243-1 | GYDFTHYGMN (5/10 clones) | (SEQ ID NO:86) |
| Y0243-2 | GYEFQHYGMN | (SEQ ID NO:87) |
| Y0243-3 | GYEFTHYGMN | (SEQ ID NO:88) |
| Y0243-4 | GYDFGHYGMN | (SEQ ID NO:89) |
| Y0243-5 | GYDFSHYGMN | (SEQ ID NO:90) |
| Y0243-6 | GYEFSHYGMN | (SEQ ID NO:91) |

Variants from library YC-101

| Name | VH "CDR7" sequence (residues 70-79) | |
|---|---|---|
| Y0244-1 | FSVDVSKSTA | (SEQ ID NO:92) |
| Y0244-2 | FSLDKSKSTA | (SEQ ID NO:93) |
| Y0244-3 | FSLDVWKSTA | (SEQ ID NO:94) |
| Y0244-4 | FSIDKSKSTA | (:95) |

The sequence of the randomized region only is shown as deduced from DNA sequencing.

When a number of clones were tested along with the parent clone pY0192 in phage-ELISA assay, none showed a distinctive improvement over the parental clone. This could be explained by the time-scale on which the assay was performed (<3 hours).

In order to quantify improvement in antigen binding over parent clone, several anti-VEGF variants' DNA were transformed into E. coli strain 34B8, expressed as Fab, and purified by passing the periplasmic shockate through a protein G column (Pharmacia) as described in Example 2 above.

CDR Combination Variants: To improve VEGF binding affinity further, mutations found by phage display were combined in different CDRs to create multiple-CDR mutants. In particular, the mutations identified in the most affinity-improved phage variants from VH1, VH2, and VH3 libraries were combined (Table 14) in order to test for additivity of their contributions to binding affinity.

TABLE 14

Combination CDR Anti-VEGF Variants

| Name | Parent clone | Mutagenesis oligo/ comments | Sequence |
|---|---|---|---|
| Y0313-1 | Y0243-1 | YC-115 (VH3: H101Y and S105T) | 5'-GCAAAGTACCCGTACTATTATGGGAC GAGCCACTGGTATTTC-3' (SEQ ID NO:96) |
| Y0317 | Y0313-1 | YC-108 (revert back to wild type) | 5'-GTCACCATCACCTGCAGCGCAAGTCA GGATATTAGCAACTATTTAAAC-3' (SEQ ID NO:97) |
| Y0313-3 | Y0238-3 | YC-116 (VH3; T105S) | 5'-CCGTACTATTATGGGAGCAGCCACTG GTATTTC-3' (SEQ ID NO:98) |

Mutations from the indicated parental vectors were combined with those from the indicated oligonucleotide by site-directed mutagenesis to yield the combination variants listed.

Version Y0317 is equivalent to Y0313-1 except that the background mutation in $V_L$ 1 was removed and its sequence reverted back to that in pY0101. The effects of mutating H101Y and S105T were tested by constructing a reversion mutant from Y0238-3.

BIAcore Analysis: The VEG F-binding affinities of Fab fragments were calculated from association and dissociation rate constants measured using a BIAcore-2000™ surface plasmon resonance system (BIAcore, Inc., Piscataway, N.J.). A biosensor chip was activated for covalent coupling of VEGF using N-ethyl-N'-(3-dimethylaminopropyl)-carbodiimide hydrochloride (EDC) and N-hydroxysuccinimide (NHS) according to the supplier's (BIAcore, Inc., Piscataway, N.J.) instructions. VEGF was buffered exchanged into 20 mM sodium acetate, pH 4.8 and diluted to approximately 50 µg/mL. An aliquot (35 µL) was injected at a flow rate of 2 µL/min to achieve approximately 700-1400 response units (RU) of coupled protein. Finally, 1 M ethanolamine was injected as a blocking agent.

For kinetics measurements, two-fold serial dilutions of Fab were injected in PBS/TWEEN™ buffer (0.05% TWEEN 20™ in phosphate buffered saline) at 25° C. at a flow rate of 10 µL/min. On rates and off rates were calculated using standard protocols (Karlsson et al. *J. Immun. Methods* 145:229-240 (1991)). Equilibrium dissociation constants, Kd's from surface plasmon resonance (SPR) measurements were calculated as koff/kon. Data are shown in Table 15 below.

TABLE 15

Kinetics of Fab-VEGF binding from BIAcore™ measurements

| Variant | Kon (10⁴/M/s) | koff (10⁻⁴/s) | Kd (nM) | Kd (wt)/Kd |
|---|---|---|---|---|
| Y0244-1 | 3.4 | 2.7 | 8 | 3.6 |
| Y0244-4 | 5.2 | 1.7 | 3.3 | 0.9 |
| Y0243-1 | 6.7 | 0.45 | 0.7 | 4.1 |
| Y0238-3 | 1.7 | ≦0.04* | ≦0.2* | ≧14* |
| Y0238-7 | 1.5 | ≦0.06* | ≦0.4* | ≧7.3* |
| Y0238-10 | 1.6 | 0.09 | 0.6 | 4.8 |
| Y0238-5 | 0.8 | 0.08 | 0.9 | 3.2 |
| Y0238-1 | 2.6 | 0.09 | 0.4 | 7.3 |
| Y0313-1 | 3.5 | ≦0.054* | ≦0.15* | ≧20* |
| Y0313-3 | 1.2 | 0.081 | 0.65 | 4.5 |

*The dissociation rate observed probably reflects an upper limit for the true dissociation rate in these experiments, since the off-rate is approaching the limit of detection by BIAcore.

The BIAcore™ data in Table 15 show that several variants had improved affinity over Y0192. For example, a CDRH1 variant, Y0243-1, showed 4.1 fold enhanced affinity, arising from mutations T28D and N31H. Variant Y0238-3 showed at least a 14 fold improvement in binding affinity over Y0192. Both CDRH3 mutations contribute to the improved affinity of Y0238-3 because reversion of T105 to S (variant Y0313-3) reduces the affinity of Y0238-3 from 0.15 nM to 0.65 nM (see Table 15). The greater affinity enhancement relative to Y0192 was seen for Y0313-1, which contained CDRH3 mutations combined with CDRH1 mutations.

Cell-Based Assay of VEGF Inhibition: Several versions of the A4.6.1 anti-VEGF antibody were tested for their ability to antagonize VEGF (recombinant; version 1-165) in induction of the growth of HuVECs (human umbilical vein endothelial cells). The 96-well plates were seeded with 1000 HuVECs per well and fasted in assay medium (F12:DMEM 50:50 supplemented with 1.5% diafiltered fetal bovine serum) for 24 h. The concentration of VEGF used for inducing the cells was determined by first titrating for the amount of VEGF that can stimulate 80% of maximal DNA synthesis. Fresh assay medium containing fixed amounts of VEGF (0.2 nM final concentration), and increasing concentrations of anti-VEGF Fab or Mab were then added. After 40 h of incubation, DNA synthesis was measured by incorporation of tritiated thymidine. Cells were pulsed with 0.5 µCi per well of [3H]-thymidine for 24 h and harvested for counting, using a TopCount gamma counter.

The results (FIG. 11) show that the full-length IgG form of F(ab)-12 was significantly more potent in inhibiting VEGF activity than the Fab form (here, Y0192 was used). However, both variants Y0238-3 and Y0313-1 showed even more potent inhibition of VEGF activity than either the Y0192 Fab or F(ab)-12 Mab. Comparing the Fab forms, variant Y0313-1 appeared >30-fold more potent than the wild-type Fab. It should be noted that the amount of VEGF (0.2 nM) used in this assay is potentially limiting for determination of an accurate IC50 for the mutant. For example, if the binding affinity ((Kd)) of the mutant is in fact <0.2 nM, the IC50 in this experiment will appear higher than under conditions of lower VEGF concentration. The result therefore supports the conclusion that the affinity-improved variant is at least 30-fold improved in affinity for VEGF, and that it effectively blocks VEGF activity in vitro. Since the variant Y0317 differs from Y0313-1 only in the reversion of the VL1 sequence to wild-type (FIG. 10A), it is predicted that Y0317 will have similar activity to Y0313-1.

Variant Y0317 (Fab) and humanized variant F(ab)-12 from Example 1 (full length and Fab) were compared for their ability to inhibit bovine capillary endothelial cell proliferation in response to a near maximally effective concentration of VEGF using the assay described in Example 1. As illustrated in FIG. 12, Y0317 was markedly more effective at inhibiting bovine capillary endothelial cell proliferation than the full length and Fab forms of F(ab)-12 in this assay. The Y0317 affinity matured Fab demonstrated an ED50 value in this assay which was at least about 20 fold lower than F(ab)-12 Fab.

The invention claimed is:

1. An isolated antibody that binds human VEGF comprising a heavy chain variable domain comprising SEQ ID NO: 126 as CDRH1, SEQ ID NO: 2 as CDRH2 and SEQ ID NO: 127 as CDRH3 and a light chain variable domain comprising SEQ ID NO: 4 as CDRL1, SEQ ID NO: 5 as CDRL2 and SEQ ID NO: 6 as CDRL3.

2. The isolated antibody of claim 1, wherein the heavy chain variable domain comprises SEQ ID NO: 116 and the light chain variable domain comprises SEQ ID NO: 115.

3. An aqueous solution comprising the isolated antibody of claim 2.

4. The aqueous solution of claim 3 comprising at least one of the following ingredients: an amino acid, a disaccharide and a non-ionic surfactant.

5. The aqueous solution of claim 4 comprising an amino acid, a disaccharide and a non-ionic surfactant.

6. The aqueous solution of claim 3 comprising at least one of the following ingredients: histidine, trehalose and a non-ionic surfactant.

7. The aqueous solution of claim 6 comprising histidine, trehalose and a non-ionic surfactant.

* * * * *